(12) United States Patent
Binner et al.

(10) Patent No.: US 9,968,335 B2
(45) Date of Patent: *May 15, 2018

(54) DEVICES AND METHODS FOR COLLECTING AND ANALYZING FLUID SAMPLES FROM THE ORAL CAVITY

(71) Applicants: Curt Binner, Furlong, NJ (US); Richard J. Fougere, Washington Crossing, PA (US); Robert W. Fusi, II, Flemington, NJ (US); Justin E. McDonough, Flemington, NJ (US); Karin Lynne Nicholson Tomishima, Chatham, NJ (US); Megha Reddy, Princeton, NJ (US)

(72) Inventors: Curt Binner, Furlong, NJ (US); Richard J. Fougere, Washington Crossing, PA (US); Robert W. Fusi, II, Flemington, NJ (US); Justin E. McDonough, Flemington, NJ (US); Karin Lynne Nicholson Tomishima, Chatham, NJ (US); Megha Reddy, Princeton, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/054,008

(22) Filed: Feb. 25, 2016

(65) Prior Publication Data

US 2016/0331356 A1  Nov. 17, 2016

Related U.S. Application Data

(62) Division of application No. 13/188,018, filed on Jul. 21, 2011, now Pat. No. 9,308,064.

(Continued)

(51) Int. Cl.
 *A61B 5/00* (2006.01)
 *B65D 81/00* (2006.01)
 (Continued)

(52) U.S. Cl.
 CPC .......... *A61B 10/0051* (2013.01); *A61B 5/097* (2013.01); *A61B 5/157* (2013.01);
 (Continued)

(58) Field of Classification Search
 CPC ....................................................... A61B 5/682
 (Continued)

(56) References Cited

U.S. PATENT DOCUMENTS 1,500,107 A   7/1924   Chandler
3,379,192 A   4/1968   Warren, Jr.
(Continued)

FOREIGN PATENT DOCUMENTS

CN   2356653 A   1/2000
CN   1476314 A   2/2004
(Continued)

*Primary Examiner* — May Abouelela

(57) ABSTRACT

Devices for collecting a fluid sample from the oral cavity, the device including a mouthpiece that includes a chamber, the chamber including front and rear inner walls; and means for collecting the fluid sample from the oral cavity; and methods of collecting and analyzing samples of fluid from the oral cavity, including the steps of placing the device in the oral cavity, collecting the fluid sample and conducting an analysis of the fluid sample.

17 Claims, 21 Drawing Sheets

Related U.S. Application Data

(60) Provisional application No. 61/367,594, filed on Jul. 26, 2010.

(51) Int. Cl.
*A61B 10/00* (2006.01)
*A61B 5/097* (2006.01)
*A61C 17/02* (2006.01)
*A61C 17/06* (2006.01)
*A61B 5/15* (2006.01)
*A61B 5/157* (2006.01)

(52) U.S. Cl.
CPC ........ *A61B 5/150045* (2013.01); *A61B 5/682* (2013.01); *A61C 17/0205* (2013.01); *A61C 17/0208* (2013.01); *A61C 17/0211* (2013.01); *A61C 17/04* (2013.01); *A61C 17/046* (2013.01); *A61B 2010/0087* (2013.01); *A61B 2560/0456* (2013.01)

(58) Field of Classification Search
USPC ........................................ 600/529, 532, 573
See application file for complete search history.

(56) References Cited

U.S. PATENT DOCUMENTS

| | | | |
|---|---|---|---|
| 3,489,141 A | 1/1970 | Warren, Jr. | |
| 3,516,402 A * | 6/1970 | Toth .................. | A61C 17/0211 601/164 |
| 3,566,869 A | 3/1971 | Crowson | |
| 3,731,675 A * | 5/1973 | Kelly ................. | A61C 17/0211 601/164 |
| 3,840,992 A * | 10/1974 | English .............. | A61C 17/0211 433/89 |
| 4,017,373 A * | 4/1977 | Shaw ................. | G01N 33/0027 204/432 |
| 4,071,956 A * | 2/1978 | Andress ............. | A61C 17/20 433/119 |
| 4,106,501 A | 8/1978 | Ozbey et al. | |
| 4,148,309 A | 4/1979 | Reibel | |
| 4,164,940 A | 8/1979 | Quinby | |
| 4,170,230 A * | 10/1979 | Nelson .............. | A61M 16/0488 128/848 |
| 4,237,574 A | 12/1980 | Kelly et al. | |
| 4,291,017 A * | 9/1981 | Beierle ............... | A61Q 11/00 424/52 |
| 5,029,576 A | 7/1991 | Evans, Sr. | |
| 5,030,098 A | 7/1991 | Branford | |
| 5,046,491 A * | 9/1991 | Derrick .............. | A61B 5/097 128/200.24 |
| 5,104,315 A * | 4/1992 | McKinley .......... | A61C 17/0211 433/216 |
| 5,137,039 A | 11/1992 | Klinkhammer | |
| 5,177,827 A | 1/1993 | Ellison | |
| 5,355,893 A * | 10/1994 | Mick ................... | A61B 5/091 600/532 |
| 5,365,624 A | 11/1994 | Berns | |
| 5,443,386 A | 8/1995 | Viskup | |
| 5,458,487 A * | 10/1995 | Komatsu ............ | A61C 19/05 433/71 |
| 5,465,728 A * | 11/1995 | Phillips ............. | A61B 5/097 128/204.17 |
| 5,509,801 A * | 4/1996 | Nicholson .......... | A61C 19/06 433/35 |
| 5,570,709 A | 11/1996 | Haddad et al. | |
| 5,616,028 A | 4/1997 | Hafele et al. | |
| 5,950,624 A * | 9/1999 | Hart ................... | A61F 5/566 128/200.26 |
| 5,980,498 A * | 11/1999 | Brown ................ | A61J 19/00 600/573 |
| 6,022,326 A * | 2/2000 | Tatum ................. | A61B 10/0051 433/91 |
| 6,126,444 A | 10/2000 | Horiguchi | |
| 6,152,733 A * | 11/2000 | Hegemann ........... | A61C 17/22 433/216 |
| 6,155,824 A | 12/2000 | Kamen et al. | |
| 6,174,164 B1 * | 1/2001 | Masjedi ............. | A61C 17/00 433/215 |
| 6,203,320 B1 | 3/2001 | Williams et al. | |
| 6,224,376 B1 * | 5/2001 | Cloonan ............. | A46B 11/066 424/49 |
| 6,353,956 B1 * | 3/2002 | Berge .................. | A46B 9/026 15/167.2 |
| 6,375,459 B1 | 4/2002 | Kamen et al. | |
| 6,468,222 B1 * | 10/2002 | Mault ................. | A61B 5/0833 600/529 |
| 6,599,253 B1 * | 7/2003 | Baum ................. | A61B 5/0813 356/303 |
| 6,602,071 B1 | 8/2003 | Ellion et al. | |
| 6,893,259 B1 * | 5/2005 | Reizenson ......... | A61C 17/0211 433/29 |
| 6,899,684 B2 * | 5/2005 | Mault ................. | A61B 5/0833 600/529 |
| 6,935,857 B1 * | 8/2005 | Farrell ................ | A61C 7/08 128/861 |
| 7,118,377 B2 * | 10/2006 | Inoue .................. | A61C 19/063 433/80 |
| 7,364,551 B2 * | 4/2008 | Allen .................. | A61B 5/411 600/531 |
| 7,837,939 B2 * | 11/2010 | Tung .................. | A61B 10/0045 422/410 |
| 7,935,065 B2 * | 5/2011 | Martin ............... | A61B 5/4205 600/587 |
| 7,972,277 B2 * | 7/2011 | Oki .................... | A61B 5/097 600/529 |
| 2002/0082544 A1 | 6/2002 | Thrash et al. | |
| 2003/0143511 A1 * | 7/2003 | Trichas .............. | A61C 5/064 433/37 |
| 2003/0153844 A1 * | 8/2003 | Smith ................. | A61B 10/0051 600/573 |
| 2003/0233086 A1 * | 12/2003 | Burns, Jr. ........... | A61K 31/06 604/512 |
| 2004/0045107 A1 | 3/2004 | Egeresi | |
| 2004/0082878 A1 * | 4/2004 | Baldwin ............ | A61B 10/0051 600/573 |
| 2004/0087874 A1 * | 5/2004 | Schneider .......... | A61B 10/0051 600/573 |
| 2004/0106081 A1 | 6/2004 | Karazivan et al. | |
| 2004/0146836 A1 * | 7/2004 | Andersen ............ | A61O 5/00 433/215 |
| 2004/0193235 A1 * | 9/2004 | Altshuler ........... | A46B 15/0002 607/88 |
| 2004/0236244 A1 * | 11/2004 | Allen .................. | A61B 5/411 600/532 |
| 2005/0037315 A1 * | 2/2005 | Inoue .................. | A61C 19/063 433/80 |
| 2005/0096563 A1 * | 5/2005 | Liang ................. | A61B 10/0051 600/573 |
| 2005/0136376 A1 | 6/2005 | Yeh | |
| 2005/0196725 A1 * | 9/2005 | Fu ....................... | A61C 17/20 433/216 |
| 2005/0272002 A1 | 12/2005 | Chenvainu et al. | |
| 2006/0078844 A1 * | 4/2006 | Goldman ............ | A61C 1/0084 433/80 |
| 2006/0188841 A1 | 8/2006 | Edel et al. | |
| 2006/0278238 A1 * | 12/2006 | Borody ............... | A61B 1/24 128/848 |
| 2006/0292521 A1 | 12/2006 | Hegemann | |
| 2007/0039614 A1 | 2/2007 | Djupesland | |
| 2007/0106138 A1 * | 5/2007 | Beiski ................ | A61B 5/682 600/349 |
| 2007/0140777 A1 | 6/2007 | Brunson | |
| 2007/0184404 A1 * | 8/2007 | Johnki ................ | A61C 17/0211 433/80 |
| 2007/0254260 A1 * | 11/2007 | Alden, IV .......... | A46B 15/0055 433/85 |
| 2008/0131844 A1 | 6/2008 | Taylor | |

(56) References Cited

U.S. PATENT DOCUMENTS

| | | |
|---|---|---|
| 2008/0182218 A1* | 7/2008 | Chen ................. A61C 7/00 433/6 |
| 2008/0199831 A1 | 8/2008 | Teichert et al. |
| 2008/0216843 A1 | 9/2008 | Jiang |
| 2008/0280251 A1 | 11/2008 | Gallagher |
| 2009/0024058 A1* | 1/2009 | Blowick ........... A61B 10/0051 600/582 |
| 2009/0038615 A1* | 2/2009 | Bradley .............. A61B 5/097 128/204.17 |
| 2009/0123886 A1* | 5/2009 | Vaska ................. A61F 5/566 433/27 |
| 2009/0136893 A1* | 5/2009 | Zegarelli ........... A61C 19/063 433/80 |
| 2009/0208898 A1* | 8/2009 | Kaplan ............... A46B 9/045 433/80 |
| 2010/0004555 A1* | 1/2010 | Bazemore ......... A61B 10/0051 600/532 |
| 2010/0016908 A1* | 1/2010 | Martin ............... A61M 11/00 607/3 |
| 2010/0081954 A1* | 4/2010 | Hyde ................. A61M 15/02 600/529 |
| 2010/0242193 A1 | 9/2010 | Harrison et al. |
| 2010/0311007 A1* | 12/2010 | Eliyahov ............. A61H 13/00 433/80 |
| 2010/0312133 A1* | 12/2010 | Bazemore ........... A61B 5/097 600/532 |
| 2010/0330538 A1* | 12/2010 | Salazar ............... A46B 9/028 433/216 |
| 2011/0015543 A1* | 1/2011 | Butlin .............. A61B 10/0051 600/573 |
| 2011/0021942 A1* | 1/2011 | Choe .................. A61B 5/097 600/532 |
| 2011/0027746 A1 | 2/2011 | McDonough et al. |
| 2011/0027747 A1 | 2/2011 | Fougere et al. |
| 2011/0027748 A1 | 2/2011 | Fusi, II |
| 2011/0027758 A1 | 2/2011 | Ochs |
| 2011/0213228 A1* | 9/2011 | Martin ................. A61B 5/4205 600/339 |
| 2011/0213328 A1 | 9/2011 | Martin |
| 2011/0294096 A1* | 12/2011 | deCastro ........... A46B 15/0002 433/216 |
| 2011/0318705 A1* | 12/2011 | Sullivan ............ A61C 17/0211 433/80 |
| 2012/0021375 A1 | 1/2012 | Binner |
| 2012/0021376 A1 | 1/2012 | Iwamoto |
| 2012/0123225 A1* | 5/2012 | Al-Tawil ............. A61B 5/228 600/301 |
| 2012/0219926 A1* | 8/2012 | Sullivan ............ A61C 17/0211 433/80 |
| 2013/0023797 A1* | 1/2013 | Hanewinkel ......... A61B 5/1121 600/590 |
| 2013/0211270 A1* | 8/2013 | St. Laurent ............ A61B 5/682 600/508 |

FOREIGN PATENT DOCUMENTS

| | | |
|---|---|---|
| CN | 101035485 A | 9/2007 |
| CN | 101076298 A | 11/2007 |
| EP | 101618 A | 2/1984 |
| EP | 688542 A | 12/1995 |
| EP | 761181 A | 3/1997 |
| EP | 1525857 A | 4/2005 |
| FR | 2455456 A | 11/1980 |
| JP | 59125556 A | 7/1984 |
| JP | 2299651 A | 12/1990 |
| JP | 6217996 A | 8/1994 |
| JP | 7047088 A | 2/1995 |
| JP | 7-15004 | 3/1995 |
| JP | 11035435 A | 2/1999 |
| JP | 11309160 A | 11/1999 |
| JP | 2001-008736 A | 1/2001 |
| JP | 2001-120579 A | 5/2001 |
| JP | 2001-120627 A | 5/2001 |
| JP | 2002-045378 A | 2/2002 |
| JP | 2004-057315 A | 2/2004 |
| JP | 2004-230118 A | 8/2004 |
| JP | 2005-319254 A | 11/2005 |
| JP | 2005-334104 A | 12/2005 |
| JP | 2006-020887 A | 1/2006 |
| JP | 2006-101941 A | 4/2006 |
| JP | 2006-239368 A | 9/2006 |
| JP | 2008-501412 A | 1/2008 |
| KR | 20100138680 A | 12/2010 |
| SU | 1024079 A | 6/1983 |
| WO | WO 96/07906 A1 | 3/1996 |
| WO | WO 2001/097709 A | 12/2001 |
| WO | WO 2003/039392 A | 5/2003 |
| WO | WO 2004/064666 A | 8/2004 |
| WO | WO 2004/108008 A | 12/2004 |
| WO | WO 2005/087133 A | 9/2005 |
| WO | WO 2005/107636 A | 11/2005 |
| WO | WO 2005/120387 A | 12/2005 |
| WO | WO 2006/040018 A | 4/2006 |
| WO | WO 2006/100452 A | 9/2006 |
| WO | WO 2006/119855 A | 11/2006 |
| WO | WO 2006/128021 A | 11/2006 |
| WO | WO 2007/071031 A | 6/2007 |
| WO | WO 2007/121760 A | 11/2007 |
| WO | WO 2008/016342 A | 2/2008 |

* cited by examiner

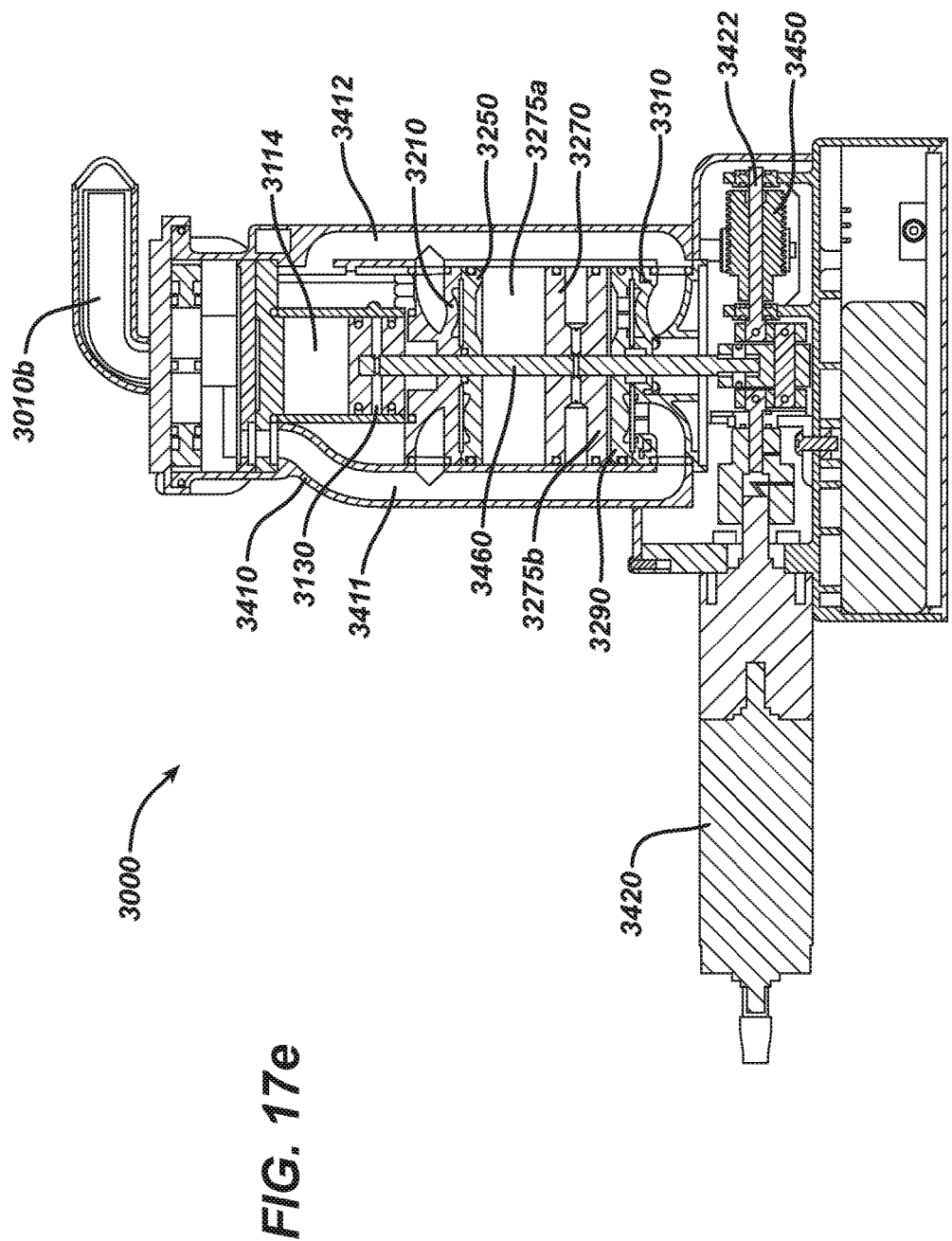

DEVICES AND METHODS FOR COLLECTING AND ANALYZING FLUID SAMPLES FROM THE ORAL CAVITY The present application is a divisional application claiming the benefit of U.S. patent application Ser. No. 13/188,018 filed Jul. 21, 2011, which also claims the benefit of U.S. provisional application 61/367,594 filed on Jul. 26, 2010, the entirety of which application is hereby incorporated by reference herein as if fully set forth herein.

FIELD OF THE INVENTION

The present invention relates to devices and methods suitable for in-home use to collect fluid samples from the oral cavity for analysis.

BACKGROUND OF THE INVENTION

In addition to regular professional dental checkups, daily oral hygiene is generally recognized as an effective preventative measure against the onset, development, and/or exacerbation of periodontal disease, gingivitis and/or tooth decay. Unfortunately, however, even the most meticulous individuals dedicated to thorough brushing and flossing practices often fail to reach, loosen and remove deep-gum and/or deep inter-dental food particulate, plaque or biofilm. Most individuals have professional dental cleanings biannually to remove tarter deposits.

For many years products have been devised to facilitate the simple home cleaning of teeth, although as yet a single device which is simple to use and cleans all surfaces of a tooth and/or the gingival or sub-gingival areas simultaneously is not available. The conventional toothbrush is widely utilized, although it requires a significant input of energy to be effective and, furthermore, a conventional toothbrush cannot adequately clean the inter-proximal areas of the teeth. Cleaning of the areas between teeth currently requires the use of floss, pick, or some such other additional device apart from a toothbrush.

Electric toothbrushes have achieved significant popularity and, although these reduce the energy input required to utilize a toothbrush, they are still inadequate to ensure proper inter-proximal tooth cleaning. Oral irrigators are known to clean the inter-proximal area between teeth. However, such devices have a single jet which must be directed at the precise inter-proximal area involved in order to remove debris. These water pump type cleaners are therefore typically only of significant value in connection with teeth having braces thereupon which often trap large particles of food. It will be appreciated that if both debris and plaque are to be removed from teeth, at present a combination of a number of devices must be used, which is extremely time consuming and inconvenient.

In addition, in order for such practices and devices to be effective, a high level of consumer compliance with techniques and/or instructions is required. The user-to-user variation in time, cleaning/treating formula, technique, etc., will affect the cleaning of the teeth.

The present invention may ameliorate one or more of the above mentioned disadvantages with existing oral hygiene apparatus and methods, or at least provides the market with an alternative technology that is advantageous over known technology, and also may be used to ameliorate a detrimental condition or to improve cosmetic appearance of the oral cavity. In addition, the invention provides diagnostic capabilities whereby devices according to the present invention collect samples of fluid from the oral cavity for analysis with respect to certain aspects as described herein below.

SUMMARY OF THE INVENTION

The present invention is directed to devices suitable for collecting samples of a fluid from the oral cavity of a mammal, the device including a mouthpiece and means for collecting the fluid sample from the oral cavity. The mouthpiece includes a chamber defined by front and rear inner walls and a base inner wall of the mouthpiece, the base wall extending between the front and rear inner walls. The invention is further directed to methods of collecting and analyzing samples of fluid from the oral cavity, including the steps of placing the device in the oral cavity, collecting the fluid samples and conducting an analysis of the fluid samples thus collected.

BRIEF DESCRIPTION OF THE DRAWINGS

FIG. 4b is an exploded view of the reciprocating flow controller of FIG. 4a;

FIG. 17b is an exploded view of the pumping section of the hand piece of FIG. 17a;

FIG. 17c is an exploded view of the vacuum section of the hand piece of FIG. 17a;

FIG. 17d is a side view of the drive system of the pumping and driving sections of the hand piece of FIG. 17a;

FIG. 17e is a cut-away view of the hand piece of FIG. 17a;

FIG. 18i is a cut-away view of the base station of the system of FIG. 18a;

DETAILED DESCRIPTION OF THE INVENTION

Figure 1:
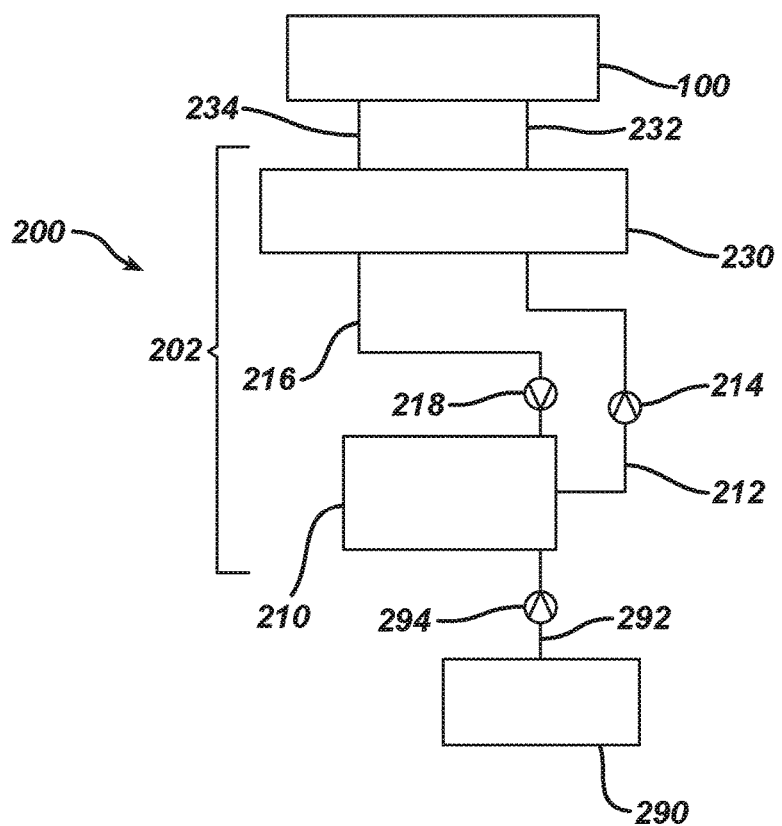
FIG. 1 is a schematic drawing of one embodiment of an apparatus that may be utilized in the present invention.

The present invention is directed to devices suitable for collecting samples of a fluid from the oral cavity of a mammal. The device includes a mouthpiece comprising a chamber for fitting around the teeth of the user and means for collecting the fluid sample from the oral cavity. In certain embodiments, the mouthpiece is suitable for directing a liquid onto a plurality of surfaces of the oral cavity. In such embodiments, the chamber maintains the liquid proximate the plurality of surfaces of the oral cavity and the front and rear inner walls include a plurality of openings. The mouthpiece includes a first manifold for containing a first portion of the liquid and providing the first portion to the chamber through the openings of the front inner wall, a second manifold for containing a second portion of the liquid and providing the second portion to the chamber through the openings of the rear inner wall, a first port for conveying the first portion of liquid to and from the first manifold, a second port for conveying the second portion of liquid to and from the second manifold. The mouthpiece further includes means for providing an effective seal of the mouthpiece within the oral cavity. The invention is further directed to methods of collecting and analyzing samples of fluid from the oral cavity, including the steps of placing the device in the oral cavity, collecting the fluid samples and conducting an analysis of the fluid samples.

The terms "reciprocating movement of liquid(s)" and "reciprocation of liquid(s)" are used interchangeably herein. As used herein, both terms mean alternating the direction of flow of the liquid(s) back and forth over surfaces of the oral cavity of a mammal from a first flow direction to a second flow direction that is opposite the first flow direction.

By "effective fit or seal", it is meant that the level of sealing between the means for directing liquid onto and about the plurality of surfaces in the oral cavity, e.g. an application tray, is such that the amount of leakage of liquid from the tray into the oral cavity during use is sufficiently low so as to reduce or minimize the amount of liquid used and to maintain comfort of the user, e.g. to avoid choking or gagging. Without intending to be limited, gagging is understood to be a reflex (i.e. not an intentional movement) muscular contraction of the back of the throat caused by stimulation of the back of the soft palate, the pharyngeal wall, the tonsillar area or base of tongue, meant to be a protective movement that prevents foreign objects from entering the pharynx and into the airway. There is variability in the gag reflex among individuals, e.g. what areas of the mouth stimulate it. In addition to the physical causes of gagging, there may be a psychological element to gagging, e.g. people who have a fear of choking may easily gag when something is placed in the mouth.

As used herein, "means for conveying liquid" includes structures through which liquid may travel or be transported throughout the systems and devices according to the invention and includes, without limitation passages, conduits, tubes, ports, portals, channels, lumens, pipes and manifolds. Such means for conveying liquids may be utilized in devices for providing reciprocation of liquids and means for directing liquids onto and about surfaces of the oral cavity. Such conveying means also provide liquid to the directing means and provide liquid to the reciprocation means from a reservoir for containing liquid, whether the reservoir is contained within a hand-held device containing the reciprocation means or a base unit. The conveying means also provides liquid from a base unit to a liquid reservoir contained within the hand-held device.

Inventions described herein include methods and devices useful in collecting fluid samples from the oral cavity of a mammal, e.g. a human, for analysis and diagnostic purposes. Devices of the invention not only provide for collection of fluid, but also may provide a beneficial effect to the oral cavity, e.g. cleaning or treatment.

Use of a mouthpiece according to the invention provides the ability to sample consistently over a wider area of the oral cavity for a higher quality and more uniform diagnostic fluid sample, as well as providing consistent sample collection at specific sites in the oral cavity, as is described in more detail herein below. Devices and methods of the invention provide the advantage of preparing the fluid sample in-vivo, prior to, during, or after sampling. In certain embodiments, fluid sample stimulating agents and/or conglomeration agents that can provide a more consistent, higher quality fluid sample may be introduced prior to, during, or after collection of the fluid sample. For example, coagulation agents for the collection and sampling of blood from the oral cavity may be introduced, for example, into the mouthpiece or means for collecting the fluid sample.

Certain methods entail collecting a fluid sample from the oral cavity for analysis and contacting a plurality of surfaces of the oral cavity with a liquid that is effective for providing the desired beneficial effect to the oral cavity. In such methods, reciprocation of the liquid(s) over the plurality of surfaces of the oral cavity is provided under conditions effective to provide the desired beneficial effect to the oral cavity. Contact of the plurality of surfaces by the liquid may be conducted substantially simultaneous. By substantially simultaneous, it is meant that, while not all of the plurality of surfaces of the oral cavity are necessarily contacted by the fluid at the same time, the majority of the surfaces are contacted simultaneously, or within a short period of time to provide an overall effect similar to that as if all surfaces are contacted at the same time. Collection of the fluid samples may be conducted prior to, or simultaneously with, or subsequent to contacting the surfaces of the oral cavity with liquid. In certain embodiments, collection may be conducted prior to, simultaneously with and subsequent to contacting the surfaces of the oral cavity with liquid.

The conditions for providing the desired beneficial effect in the oral cavity may vary depending on the particular environment, circumstances and effect being sought. The different variables are interdependent in that they create a specific velocity of the liquid. The velocity requirement may be a function of the formulation in some embodiments. For example, with change in the viscosity, additives, e.g. abrasives, shear thinning agents, etc., and general flow properties of the formulation, velocity requirements of the jets may change to produce the same level of efficacy. Factors which may be considered in order to provide the appropriate conditions for achieving the particular beneficial effect sought include, without limitation, the velocity and/or flow rate and/or pressure of the liquid stream, pulsation of the liquid, the spray geometry or spray pattern of the liquid, the temperature of the liquid and the frequency of the reciprocating cycle of the liquid.

The liquid pressures, i.e. manifold pressure just prior to exit through the jets, may be from about 0.5 psi to about 30 psi, or from about 3 to about 15 psi, or about 5 psi. Flow rate of liquid may be from about 10 ml/s to about 60 ml/s, or about 20 ml/s to about 40 ml/s. It should be noted that the larger and higher quantity of the jets, the greater flow rate required at a given pressure/velocity. Pulse frequency (linked to pulse length and delivery (ml/pulse), may be from about 0.5 Hz to about 50 Hz, or from about 5 Hz to about 25 Hz. Delivery pulse duty cycle may be from about 10% to 100%, or from about 40% to about 60%. It is noted that at 100% there is no pulse, but instead a continuous flow of liquid. Delivery pulse volume (total volume through all jets/nozzles) may be from about 0.2 ml to about 120 ml, or from about 0.5 ml to about 15 ml. Velocity of jetted pulse may be from about 4 cm/s to about 400 cm/s, or from about 20 cm/s to about 160 in/s. Vacuum duty cycle may be from about 10% to 100%, or from about 50% to 100%. It is noted that vacuum is always on at 100%. Volumetric delivery to vacuum ratio may be from about 2:1 to about 1:20, or from about 1:1 to 1:10.

The liquid(s) may include at least one ingredient, or agent, effective for providing the beneficial effect sought, in an amount effective to provide the beneficial effect when contacted with the surfaces of the oral cavity. For example, the liquid may include, without limitation, an ingredient selected from the group consisting of a cleaning agent, an antimicrobial agent, a mineralization agent, a desensitizing agent, surfactant and a whitening agent. In certain embodiments, more than one liquid may be used in a single session. For example, a cleaning solution may be applied to the oral cavity, followed by a second solution containing, for example, a whitening agent or an antimicrobial agent. Solutions also may include a plurality of agents to accomplish more than one benefit with a single application. For example, the solution may include both a cleansing agent and an agent for ameliorating a detrimental condition, as further discussed below. In addition, a single solution may be effective to provide more than one beneficial effect to the oral cavity. For example, the solution may include a single agent that both cleans the oral cavity and acts as an antimicrobial, or that both cleans the oral cavity and whitens teeth.

Liquids useful for improving the cosmetic appearance of the oral cavity may include a whitening agent to whiten teeth in the cavity. Such whitening agents may include, without limitation, hydrogen peroxide and carbamide peroxide, or other agents capable of generating hydrogen peroxide when applied to the teeth. Other whitening agents may include abrasives such as silica, sodium bicarbonate, alumina, apatites and bioglass.

It is noted that, while abrasives may serve to clean and/or whiten the teeth, certain of the abrasives also may serve to ameliorate hypersensitivity of the teeth caused by loss of enamel and exposure of the tubules in the teeth.

In some embodiments, the liquid may comprise an antimicrobial composition containing an alcohol having 3 to 6 carbon atoms. The liquid may be an antimicrobial mouthwash composition, particularly one having reduced ethanol content or being substantially free of ethanol, providing a high level of efficacy in the prevention of plaque, gum disease and bad breath. Noted alcohols having 3 to 6 carbon atoms are aliphatic alcohols. A particularly aliphatic alcohol having 3 carbons is 1-propanol.

In one embodiment the liquid may comprise an antimicrobial composition comprising (a) an antimicrobial effective amount of thymol and one or more other essential oils, (b) from about 0.01% to about 70.0% v/v, or about 0.1% to about 30% v/v, or about 0.1% to about 10% v/v, or about 0.2% to about 8% v/v, of an alcohol having 3 to 6 carbon atoms and (c) a vehicle. The alcohol may be 1-propanol. The liquid vehicle can be aqueous or non-aqueous, and may include thickening agents or gelling agents to provide the compositions with a particular consistency. Water and water/ethanol mixtures are the preferred vehicle.

Another embodiment of the liquid is an antimicrobial composition comprising (a) an antimicrobial effective amount of an antimicrobial agent, (b) from about 0.01% to about 70% v/v, or about 0.1% to about 30% v/v, or about 0.2% to about 8% v/v, of propanol and (c) a vehicle. The antimicrobial composition of this embodiment exhibits unexpectedly superior delivery system kinetics compared to prior art ethanolic systems. Exemplary antimicrobial agents which may be employed include, without limitation, essential oils, cetyl pyidium chloride (CPC), chlorhexidine, hexetidine, chitosan, triclosan, domiphen bromide, stannous fluoride, soluble pyrophosphates, metal oxides including but not limited to zinc oxide, peppermint oil, sage oil, sanguinaria, dicalcium dihydrate, aloe vera, polyols, protease, lipase, amylase, and metal salts including but not limited to zinc citrate, and the like. A particularly preferred aspect of this embodiment is directed to an antimicrobial oral composition, e.g. a mouthwash having about 30% v/v or less, or about 10% v/v or less, or about 3% v/v or less, of 1-propanol.

Yet another embodiment of the liquid is a reduced ethanol, antimicrobial mouthwash composition which comprises (a) an antimicrobial effective amount of thymol and one or more other essential oils; (b) from about 0.01 to about 30.0% v/v, or about 0.1% to about 10% v/v, or about 0.2% to about 8% v/v, of an alcohol having 3 to 6 carbon atoms; (c) ethanol in an amount of about 25% v/v or less; (d) at least one surfactant; and (e) water. Preferably the total concentration of ethanol and alcohol having 3 to 6 carbon atoms is no greater than 30% v/v, or no greater than 25% v/v, or no greater than 22% v/v.

In still another embodiment, the liquid is an ethanol-free antimicrobial mouthwash composition which comprises (a)

an antimicrobial effective amount of thymol and one or more other essential oils; (b) from about 0.01% to about 30.0% v/v, or about 0.1% to about 10% v/v, or about 0.2% to about 8%, of an alcohol having 3 to 6 carbon atoms; (c) at least one surfactant; and (d) water.

The alcohol having 3 to 6 carbon atoms is preferably selected from the group consisting of 1-propanol, 2-propanol, 1-butanol, 2-butanol, tert-butanol and corresponding diols. 1-Propanol and 2-propanol are preferred, with 1-propanol being most preferred.

In addition to generally improving the oral hygiene of the oral cavity by cleaning, for example, removal or disruption of plaque build-up, food particles, biofilm, etc., the inventions are useful to diagnose and ameliorate detrimental conditions within the oral cavity and to improve the cosmetic appearance of the oral cavity. Detrimental conditions may include, without limitation, caries, gingivitis, inflammation, symptoms associated with periodontal disease, halitosis, sensitivity of the teeth and fungal infection. The liquids themselves may be in various forms, provided that they have the flow characteristics suitable for use in devices and methods of the present invention. For example, the liquids may be selected from the group consisting of solutions, emulsions and dispersions. In certain embodiments, the liquid may comprise a particulate, e.g. an abrasive, dispersed in a liquid phase, e.g. an aqueous phase. In such cases, the abrasive would be substantially homogeneously dispersed in the aqueous phase in order to be applied to the surfaces of the oral cavity. In other embodiments, an oil-in-water or water-in-oil emulsion may be used. In such cases, the liquid will comprise a discontinuous oil phase substantially homogeneously dispersed within a continuous aqueous phase, or a discontinuous aqueous phase substantially homogenously dispersed in a continuous oil phase, as the case may be. In still other embodiments, the liquid may be a solution whereby the agent is dissolved in a carrier, or where the carrier itself may be considered as the agent for providing the desired beneficial effect, e.g., an alcohol or alcohol/water mixture, usually having other agents dissolved therein.

The present invention includes devices, e.g. an oral hygiene device, for example a dental cleaning apparatus, suitable for in-home use and adapted to collect fluid samples from the oral cavity and to direct liquid onto a plurality of surfaces of a tooth and/or the gingival area. In certain embodiments the surfaces of the oral cavity are contacted by the liquid substantially simultaneously. As used herein, reference to the gingival area includes, without limitation, reference to the sub-gingival pocket. The appropriate liquid is directed onto a plurality of surfaces of teeth and/or gingival area substantially simultaneously in a reciprocating action under conditions effective to provide cleaning, and/or general improvement of the cosmetic appearance of the oral cavity and/or amelioration of a detrimental condition of the teeth and/or gingival area, thereby providing generally improved oral hygiene of teeth and/or gingival area. For example, one such device cleans teeth and/or the gingival area and removes plaque using an appropriate cleaning liquid by reciprocating the liquid back and forth over the front and back surfaces and inter-proximal areas of the teeth, thereby creating a cleaning cycle while minimizing the amount of cleaning liquid used.

Devices of the invention that provide reciprocation of the liquid comprise a means for controlling reciprocation of the liquid. The controlling means include means for conveying the liquid to and from a means for directing the liquid onto the plurality of surfaces of the oral cavity. In certain embodiments, the means for providing reciprocation of the liquid comprises a plurality of portals for receiving and discharging the liquid, a plurality of passages, or conduits, through which the liquid is conveyed, and means for changing the direction of flow of the liquid to provide reciprocation of the liquid, as described in more detail herein below. The controlling means may be controlled by a logic circuit and/or a mechanically controlled circuit.

In certain embodiments, devices for providing reciprocation may include a means for attaching or connecting the device to a reservoir for containing the liquid. The reservoir may be removably attached to the device. In this case, the reservoir and the device may comprise means for attaching one to the other. After completion of the process, the reservoir may be discarded and replaced with a different reservoir, or may be refilled and used again. In other embodiments, the reciprocating device will include a reservoir integral with the device. In embodiments where the device may be attached to a base unit, as described herein, the reservoir, whether integral with the device or removably attached to the device, may be refilled from a supply reservoir which forms a part of the base unit. Where a base unit is utilized, the device and the base unit will comprise means for attaching one to the other.

The device will comprise a power source for driving the means for reciprocating liquids. The power source may be contained within the device, e.g. in the handle of the device, for example, batteries, whether rechargeable or disposable. Where a base unit is employed, the base may include means for providing power to the device. In other embodiments, the base unit may include means for recharging the rechargeable batteries contained within the device.

Devices for providing reciprocation of liquids will include means for attaching the device to means for directing the liquid onto the plurality of surfaces of the oral cavity, e.g. an application tray or mouthpiece. In certain embodiments, the directing means provides substantially simultaneous contact of the plurality of surfaces of the oral cavity by the liquid. The attachment means may provide removable attachment of the mouthpiece to the device. In such embodiments, multiple users may use their own mouthpiece with the single device comprising the reciprocating means. In other embodiments, the attachment means may provide a non-removable attachment to the mouthpiece, whereby the mouthpiece is an integral part of the device. Devices for providing reciprocation as described above may be contained within a housing with other device components so as to provide a hand-held device suitable for providing liquid to the directing means, as described herein below.

The means for directing the liquid onto the surfaces of the oral cavity, e.g. an application tray or mouthpiece, is comprised of multiple components. The directing means comprises a chamber for maintaining the liquid proximate the plurality of surfaces, i.e. liquid-contacting-chamber (LCC). By "proximate", it is meant that the liquid is maintained in contact with the surfaces. The LCC is defined by the space bounded by the front inner wall and rear inner wall of the mouthpiece, and a wall, or membrane, extending between and integral with the front and rear inner walls of the mouthpiece, and in certain embodiments, a rear gum-sealing membrane. Together, the front and rear inner walls, the wall extending there between and rear gum-sealing membrane form the liquid-contacting-chamber membrane (LCCM). The general shape of the LCCM is that of a "U" or an "n", depending on the orientation of the mouthpiece, which follows the alignment of the teeth to provide uniform and optimized contact by the liquid. The LCCM may be flexible or rigid depending on the particular directing means. The membrane may be located as a base membrane of the LCCM. The front and rear inner walls of the LCCM each include a plurality of openings, or slots, through which the liquid is directed to contact the plurality of surfaces of the oral cavity.

The LCCM design may be optimized for maximum effectiveness as it relates to the size, shape, thickness, materials and volume created around the teeth/gingiva, nozzle design and placement as it relates to the oral cavity and the teeth in conjunction with the manifold and gingival margin seal to provide comfort and minimize the gagging reflex of the user. The combination of the above provides effective contact of the teeth and gingival area by the liquid.

The LCCM provides a controlled and isolated environment with known volume, i.e. the LCC, to contact teeth and/or gingival area with liquids, and then to remove spent liquids, as well as debris, plaque, etc., from the LCC without exposing the whole oral cavity to liquid, debris, etc. This decreases the potential for ingestion of the liquids. The LCCM also allows increased flow rates and pressure of liquids without drowning the individual nozzles when significant flow rates are required to provide adequate cleaning, for example. The LCCM also allows reduced liquid quantities and flow rates when required, as only the area within the LCC is being contacted with liquid, not the entire oral cavity. The LCCM also allows controlled delivery and duration of contact of liquid on, through and around teeth and the gingival area, allowing increased concentrations of liquids on the area being contacted by the liquid, thereby providing more effective control and delivery of liquid.

The LCCM may also allow controlled sampling of the oral cavity due to precise positioning of the mouthpiece in the oral care cavity for use in detection or diagnostics. It can also provide capability to image and/or diagnose gum health through a variety of methods. The system also provides the ability to expand functionality for cleaning and/or treating other oral cavity areas such as, but not limited to, the tongue, cheeks, gingival, etc.

In some embodiments, samples are collected from the oral cavity for diagnostic analysis. Advantages of controlled sampling of the oral cavity may include real-time analysis and feedback to the user, consistent sampling due to the mouthpiece, and the ability to create a baseline of oral cavity conditions for the user and automatically analyze trends over time for personalized analysis. The mouthpiece provides an excellent opportunity for consistent collection of samples of various fluids in the oral cavity. By "consistent collection", it is meant that the collection of fluids, and thus the fluid samples, are unaffected by compliance or the technique employed by the user. The mouthpiece may be secured in the user's mouth in the same fashion every time, thus placing the means for collecting the fluid sample in the same location for every sample collection. In addition, the collection environment may be consistent and controlled every time. In certain embodiments, the sampling environment and/or location may be confirmed via feedback from sensor(s) placed in the mouthpiece.

The user may benefit from routine and regular tests to understand their personal baseline, as many diagnostic tests vary from one individual to another. The user's baseline may be determined over time, allowing a thorough and proper analysis through each use of the system.

Several types of fluid may be collected from the oral cavity for analysis. They may include, but are not limited to, gas, gingival crevicular fluid (GCF), blood, saliva, and any combination thereof.

For example, a variety of beneficial diagnostic analyses may be performed using the gas in the oral cavity. This invention allows for consistent collection of oral cavity gases for repeatable analysis. A baseline may be determined and tracked over time, integrating trend analysis and providing feedback to the user.

When positioned in the mouth, the mouthpiece may create a vacuum in the oral cavity with one or more nozzles, drawing air from the oral cavity into the device for storage and/or analysis. The collection may be done in a variety of ways, such as running the system in vacuum mode after the appliance is inserted into the mouth, but before the liquid delivery cycle begins. In this case, the same nozzles used for delivery and vacuum of the cleaning and treatment liquids may be used to collect the oral cavity gas, with no extra manifolds, isolated chambers, or similar structures.

The mouthpiece may also have a dedicated manifold for collecting oral cavity air that is separate from the cleaning and treatment liquid delivery system of the mouthpiece. The manifold may be connected to one or more nozzles in the appliance, similar to that of the delivery system. It may also be connected to any other nozzles or ports in the mouthpiece, appropriately placed for oral cavity gas collection. In some embodiments, the mouthpiece may have an orifice which collects gas just above the tongue in the center of the oral cavity.

The oral cavity gas sample may be collected before cleaning/treatment, during cleaning and treatment (depending on the collection port location), after cleaning/treatment, or any combination thereof. A variety of diagnostics may be performed using the oral cavity gas, benefiting from consistent collection techniques to yield the best and most consistent results possible.

Oral malodor, or halitosis, is a common condition in which the source of the odor typically originates in the oral cavity, usually at the dorsum of the tongue. Certain oral bacteria produce malodorous volatile sulfur compounds (VSCs), including hydrogen sulfide, methyl mercaptan and dimethyl sulfide. A number of methods to detect levels of VSCs in the air in the oral cavity exist in the art. Collectively these methods are sufficiently sensitive to detect these odorous compounds, but consistency of results is highly user-dependent. All of these collection methods could benefit from consistent collection or sampling technique to ensure consistent, robust measurements. Such controlled sampling may be achieved through sample collection via the appliance.

The device may collect a sample of gas from the oral cavity, and measure the levels of VSCs present (ppb) via a zinc oxide semiconductor sensor as known in the art. The measurement may be recorded whenever the device is used by the user, such as twice daily, daily or weekly and tracked over time. As an example, data from an initial 30-day period may be used to establish a baseline against which all subsequent measurements may be compared. Any deviations from normal trends may trigger a feedback alert to the user for monitoring development of and/or treatment progress of halitosis. Alternatively, the device may collect a gas sample over the tongue and detect VSCs via gas chromatography in the base station. An additional alternative may include sample collection in the device, storage of the sample in an appropriate detachable compartment, and shipment of the sample to an outside laboratory for analysis. In each case, the user may receive the added benefit of consistent, compliance-free monitoring of VSC levels in the oral cavity, which they would not receive through available oral hygiene measures. In addition, users may benefit from tracking this information over time, which may allow for immediate alerts for any adverse changes in VSC levels and may enable the individual to take immediate corrective actions.

Alternatively, a variety of beneficial diagnostic analyses may be performed using the Gingival Crevicular Fluid (GCF) in the oral cavity. GCF is a fluid found in the gingival pocket of the oral cavity, and is very useful in various types of diagnostics. Several methods of collecting the GCF exist in the art. These include inserting a probe in the gingival pocket to extract the fluid, and swabbing the fluid from the pocket. While these methods effectively retrieve the fluid, sample to sample inconsistencies are possible. The mouthpiece discussed here allows for consistent GCF collection.

Each time the mouthpiece is inserted into the mouth, it is located in the same position. For GCF sampling, a plurality of nozzles, or micropipettes, are placed at regularly or randomly spaced intervals about the mouthpiece near and/or directed at the gum line between the teeth and gums and/or within the gingival pocket. The nozzles or micropipettes may be located along the outer, inner, or both walls of the chamber of the mouthpiece. A suitable buffer solution is directed into the gum pocket from one or more nozzles, extracting and mixing with the GCF. A vacuum is then created at the nozzles to collect the mixed solution and move it into the device for analysis. This may be done before, during, or after the cleaning/treatment process, or any combination thereof. Alternatively, the micropipettes and or nozzles can be utilized to collect the sample without introduction of a buffering solution, or pretreatment means, utilizing vacuum and/or capillary action to promote sample collection.

Gingivitis, or inflammation of the gum tissue, is a common, non-destructive form of gum disease. It is most commonly caused by biofilm (plaque) accumulation on the teeth. If left untreated, gingivitis may progress to irreversible periodontal disease and lead to loss of tissue, bone and tooth attachment. Gingivitis is reversible and may be easily treated with an oral hygiene routine to remove plaque biofilm on a daily basis. Despite this, most adults will have occurrences of gingivitis at multiple sites in the mouth over their lifetime and could benefit from routine monitoring of gum health. GCF is an inflammatory exudate that contains a number of biomarkers including bacterial antigens, inflammatory markers, and bacterial and host metabolites. Many of these markers are specific to gingivitis and periodontitis and could be used as target analytes to monitor gingival health. However, since conventional GCF collection is difficult, time consuming and requires a trained professional, it is usually reserved as a research methodology and is not routinely utilized in dental offices. Most adults would therefore never receive the benefit of such an analysis.

In some embodiments, the device may use microfluidic immunoassays to analyze GCF samples to detect antigens specific to bacteria associated with gingivitis, or periodontitis, inflammatory markers and/or metabolites associated with gingivitis and/or periodontitis. The analysis may be performed in the device itself, or in the base station on a daily, weekly or monthly basis. The results may be tracked over time to monitor signs of development and/or progression of gum disease, and status of treatment. An initial specified period may be used to establish a baseline against which all subsequent measurements could be compared. A warning appropriate to the level of disease detected may be issued to the user through the device and results may also be forwarded to a dental professional for further evaluation.

In another embodiment, a variety of beneficial diagnostic analyses may be performed using saliva from the oral cavity. Though many collection methods for saliva exist in the art, these often require professional training with proper technique to collect the correct quantity of the desired fluid. The sample must then be analyzed in a secondary process. The mouthpiece discussed here allows for consistent collection of saliva for repeatable analysis.

Each time the mouthpiece is inserted into the mouth, it is located in the same position. For saliva sampling, a plurality of nozzles are located throughout the oral cavity. As the system operates, cleaning/treating liquid may move through the appliance, into the oral cavity, and out of the oral cavity. As the fluid is moving through the oral cavity, it may mix with saliva and therefore move saliva through the system. The mixed solution may be analyzed in the device as it is functioning or stored for later analysis. If desired, several means may be used to increase saliva production and increase the percentage of saliva in the overall system fluid mixture. Methods include, but are not limited to, use of a salivation-inducing fluid during system operation, user exposure to specific saliva-inducing smells, electrical stimulation, ultrasonic stimulation, or mechanical stimulation.

Alternatively, a saliva mixture may be collected through a separate and/or specific manifold in the mouthpiece. Through any means of collection, the saliva may be collected before, during, or after the cleaning/treatment process, or any combination thereof.

The mouthpiece may also have a collection means that contacts the tongue to suck or absorb saliva from it. The probe or pad contacting the tongue may have one or more nozzles that pull a vacuum on the tongue to collect the saliva. Alternatively, the pad may absorb saliva and automatically extract the saliva in a secondary process, or otherwise analyze the saliva directly on the pad. As in the above techniques, this method is technique- and compliance-free for the user.

Saliva samples may be utilized as diagnostic samples for a number of oral health conditions and analyzed via a variety of diagnostic methods.

The device may diagnose caries risk through microfluidic immunoassays performed on saliva samples to detect proteinaceous antigens specific to *S. mutans* and/or *Lactobacillus* bacteria with fluorescence detection of output. The assay may be performed weekly or monthly, and a warning registered to the user if the levels of bacteria were to surpass the threshold for high caries risk. Alternatively, the device may measure the buffering capacity of the saliva using a series of absorbent pads embedded with pH indicators, as known in the art. An alert to the user may be triggered by low buffering capacity results, indicating a high risk for caries. As an additional alternative, the device may directly measure the concentration of fluoride ions in the saliva using a fluoride ion specific electrode. A baseline may be established by monitoring the fluoride ion concentration on a daily or weekly basis for a specified period of time. Any significant deviations from baseline concentration trends would trigger an alert to the user.

The device may use microfluidic immunoassays to analyze saliva samples for the presence of antigens specific to bacteria associated with gingivitis and periodontitis. The assay may be performed daily, weekly or monthly, with the data being recorded over time. Any adverse deviations from normal trends would alert the user to consult a dental professional for further evaluation.

Alternatively, the device may analyze saliva samples using a lateral flow technology (LFT) test. After collection, the sample may be mixed with a bacterial cell lysing agent and the resulting mixture applied to a lateral flow devise in the base station which may detect antigens specific to *S. mutans* for assessing carries risk as known in the art. The lateral flow device may also detect antigens specific to bacteria associated with gingivitis and/or periodontisis either alone or in combination with *S. mutans* antigens. It may also react with thiols in volatile sulfur compounds (VSCs), or detect antigens specific to VSC-producing bacteria to produce a detectable color change with the intensity of the color correlating with the concentration of VSCs present. The lateral flow test may be performed in the base station with refillable LFT strips either specific for a single condition, or strips that will detect a combination of antigens and/or chemistries for multiple oral conditions. Results may be assessed in the base station. Alternatively, the test may be performed externally, with the user applying the sample collected and prepared by the device to the LFT strip with test results read visually by the user as the appearance of a colored indicator or color change on the strip. Conversely, analysis of the strip can occur automatically through digital image analysis.

Alternatively, the device may analyze saliva samples to determine the prevalence of disease-associated bacteria within the entire population in the sample using quantitative Polymerase Chain Reaction (qPCR) analysis. The analysis may be performed within the device or base station using microfluidic techniques or, alternatively, the sample may be collected and contained within the device and sent to an outside laboratory for analysis. The analysis may be performed daily, weekly or monthly and a high number of *S. mutans* or Lactobacilli would trigger a warning to the user that they may be at risk for developing caries, whereas high counts of organisms associated with periodontitis would alert the user to a possible prevalence for gum disease. In each case the analysis could be performed daily, weekly or monthly and tracked over time to identify significant deviations from normal trends.

Alternatively, the device may analyze saliva samples using DNA-DNA hybridization techniques to determine the bacterial population profile of the sample. This information may be recorded daily, weekly or monthly and tracked over time to monitor changes in relative amounts of different bacteria in the entire population. Significant adverse population shifts would trigger a warning to the user for increased risk of disease onset or progression (such as high risk for caries or periodontal disease). The information may also be used to track the progress of disease treatment.

In each of these cases, the user would be highly unlikely or unable to perform the diagnostic test described, and most are not routinely practiced in dental offices. The mouthpiece may provide the added benefit of acquiring this information in a consistent manner on a regular basis, and may enable the user to closely monitor their oral health status and take any required corrective measures in a timely fashion.

The collection methods and diagnostic analysis discussed above may used in conjunction with one another, in any combination. Due to the flexibility of the system, collection of each sample only needs to occur when determined or pre-established, rather than during every use. For example, some samples may need to be taken only once a week, while others ideally may be taken one or more times a day. The system may automatically adjust the sampling plan as needed for each individual, based on results and predetermined criteria.

In addition, much information and analysis can be derived from color metrics obtained from various parts of the oral cavity. The color, texture, and opacity of the gums, cheeks, and/or tongue is an excellent indicator of health conditions when analyzed as a single data point or as a trend over time. The color, texture, and opacity of teeth may also be analyzed and tracked to understand benefits of whitening efforts or to monitor degradation from lifestyle behavior or health deficiencies. Methods known in the art for analyzing color, textures and opacity include light sources with detectors to look for specific wavelengths/colors, CCD (charge coupled device) and CMOS (complementary metal oxide semiconductor) image sensors to compare a live image against reference data/images, and others. The appropriate sensors, detectors, and light sources may be embedded in the appliance so that color, texture, and/or opacity analysis may be performed before, during, or after the cleaning/treatment cycle. The mouthpiece of this invention, as well as the incorporated sensors, will be placed in the same position every time with consistent environmental conditions, creating repeatable and robust data. There may be no special interaction for this function by the user, and they may be provided with feedback over time as the device is regularly used. This data would not normally be collected by the user without extra effort involving separate devices requiring correct technique and interpretation.

The device may analyze tooth shade using methods photoimaging techniques known in the art that employ a CCD camera, spectrophotometer and imaging software to map a tooth and record the L, a, b color scale value for the area. This data could be collected on a daily or weekly basis and alert the user to development of staining, plaque and/or tartar development.

The device may utilize quantitative light fluorescence (QLF) to diagnose early carious lesions. The device may employ two-way optics to illuminate the tooth surface with 488 or 655 nm light and detect the resulting fluorescence. Healthy tooth surfaces would fluorescence green, while areas of demineralization would appear gray. These demineralized lesions are reversible with topical fluoride treatment but are generally undetectable using traditional methods such as dental probes. The appliance may acquire this data on a daily, weekly or monthly basis and alert the user to the need for such treatment before the formation of irreversible damage to the tooth surface.

In addition to the oral health diagnostics as described above, the device can also be utilized and expanded to diagnose general health conditions and biomarkers related to systemic health, including but not limited to cancers, hypertension, diabetes, etc.

Combinations of different biomarkers and samples can be combined to provide a more robust analysis and diagnosis for specific conditions and provide improved results, such as using GCG and saliva samples, and/or checking multiple biomarkers that are linked to a specific condition. The presence of one biomarker might also automatically trigger sampling and analysis of other biomarkers to improve diagnostic results.

Diagnostic results can also be used to provide automated treatment for the condition, and/or direct the user to purchase a specific product to address a potential condition. The treatment could also be customized by adding appropriate additives to the cleaning formulation for a specific user depending on their diagnostic result. As an example, adding a antibacterial, halitosis reducing agent, sensitivity agent, whitening agent, fluoride, and/or any combination of these or other additives to treat an oral and/or systemic condition.

The thickness of the walls of the LCCM may be within a range of 0.2 mm to 1.5 mm, to provide necessary physical performance properties, while minimizing material content, and optimizing performance. The distance between the inner walls of the LCCM to the teeth may be from about 0.1 mm to about 5 mm, and more typically an average distance of about 2.5 mm to provide maximum comfort, while minimizing customization and LCC volume requirements.

The size and shape of the mouthpiece preferably utilizes three basic universal sizes (small, medium and large) for both the top and bottom teeth, but the design provides mechanisms to allow different levels of customization as required to ensure comfort and functionality to the individual user. The device may incorporate a switching mechanism, which would allow it to be operable only when in the correct position in the mouth. The mouthpiece may include both upper and lower sections to provide substantially simultaneous contact of the plurality of surfaces of the oral cavity by liquid. In an alternate embodiment the upper and lower sections may be cleaned utilizing a single bridge that could be used on the upper or lower teeth and gums of the user (first placed on one portion for cleaning, then subsequently placed over the other portion for cleaning).

The number and location of openings, also referred to herein as slots, jets or nozzles, contained within the inner walls of the mouthpiece through which the liquid is directed will vary and be determined based upon the circumstances and environment of use, the particular user and the beneficial effect being sought. The cross-sectional geometry of the openings may be circular, elliptical, trapezoidal, or any other geometry that provides effective contact of the surfaces of the oral cavity by the liquid. The location and number of openings may be designed to direct jets of liquid in a variety of spray patterns effective for providing the desired beneficial effect. Opening diameters may be from about 0.1 to about 3 mm, or from about 0.2 mm to about 0.8 mm, or about 0.5 mm, to provide effective cleaning and average jet velocities and coverage.

Optimal opening placement and direction/angles allows coverage of substantially all teeth surfaces in the area if the oral cavity to be contacted by liquid, including but not limited to interdental, top, side, back, and gingival pocket surfaces. In alternate embodiments, the openings could be of different sizes and different shapes to provide different cleaning, coverage and spray patterns, to adjust velocities, density and fan patterns (full cone, fan, partial, cone, jet), or due to formulation consideration. Nozzles could also be designed to be tubular and or extend from the LCCM to provide directed spray, or act as sprinkler like mechanism to provide extended coverage across the teeth, similar to a hose sprinkler system. The nozzles are preferably integral to the inner walls of the LCCM and can be incorporated into the inner walls through any number of assembly or forming techniques known in the art (insert molded, formed in membrane through machining, injection molding, etc.).

The LCCM may be an elastomeric material such as ethylene vinyl acetate (EVA), thermoplastic elastomer (TPE), or silicone, to allow motion of the inner walls and provide a greater jet coverage area with minimal mechanics, reducing the volumetric flow requirements to achieve optimized performance, while providing a softer and more flexible material to protect the teeth if direct contact with the teeth is made. A flexible membrane may also provide acceptable fitment over a large range of users, due to its ability to conform to the teeth. Alternatively, the LCCM could be made of a rigid or semi-rigid material, such as but not limited to a thermoplastic.

It may be desirable, although not required, to have motion of the LCCM relative to the teeth. Movement of the LCCM, and subsequently the nozzle direction during the cleaning and/or treatment operation, provides increased coverage of the teeth/gums, while minimizing the number of nozzles/fluidic jets required to provide this coverage for cleaning and/or treatment. It also reduces the required overall fluid flow requirement, which reduces the total liquid fluid requirement and overall device overhead as it relates to provide the appropriate flow, resulting in a smaller, lighter, and useable device. This motion also allows the device to provide a more universal fit for the user (same sized LCCM can be used for different users), while also allowing compensation for minor misplacement/orientation of the LCCM over the users teeth/gums.

In some embodiments, motion of the LCCM is provided through pressurization, pulsation, and movement of liquid through the manifolds. In alternate embodiments, this motion can be achieved through vibration, sonic, or ultrasonic mechanism. This motion can also be provided through a separate network of tubes and/manifolds constructed within or attached to the LCC, which can be charged or discharged with liquid and/or air to create a desired motion of the membrane. In addition, motion of the LCCM may be the result of the motion of the user's jaw or teeth. In an alternate embodiment, the LCCM motion system can also include mechanically moving the LCCM via a track-like guided reciprocating motion, the track being created by the teeth. In another alternate embodiment, the desired LCCM motion can be created by using one or a multiple of linear motor systems, which allow sequential motion via multiple permanent magnet/coil pairs located in strategic locations on the mouthpiece to provide optimized cleaning and treatment sequences for directing jets and cleaning elements. In yet another alternative embodiment, motion may be created by shape memory materials or piezoelectrics.

In the preferred embodiment, the system provides pulsation through a variety of elements, including through the delivery manifold, channels, and nozzles, the vacuum manifolds, channels and nozzles, and through the reciprocation/reversal of flow, where the delivery channels become the vacuum channels, and the vacuum channels the delivery channels. Pulsation of the fluid results in a varying pressure of the fluid within the elements described creating the desired motion of the LCCM as described. The LCCM is designed to work with the fluid pulsation means provided to create the necessary motion and movement/direction of the nozzles in the X, Y and Z directions, through the combination of materials and design of the LCCM, while still providing the necessary performance required to minimize leakage into the oral cavity and without compromising structural integrity of the mouthpiece, including the LCCM.

The movement/pulsation of the elements can be coordinated or random. The pulsation can be provided at a fixed frequency, multiple frequencies, and/or out of phase for the individual elements to create the desired motion. It is not necessary to pulsate all of the elements at once. As an example, in some cases only the delivery elements may be required to be pulsated, while the vacuum is not pulsated.

In addition, the LCCM could include cleaning elements and/or spacers that would move relative to the LCCM to provide some effect to the teeth and/or gums. These cleaning elements and/or spacers can also be used to constrain the motion of the LCCM if required to maintain a minimum distance between the LCCM and teeth/and/or gums during motion and fitment of the device to the user. This provides a minimum distance between the nozzle located within the LCCM and the surface to be treated and cleaned, preventing a nozzle from being blocked, and preventing fluid delivery and/or removal. As the spacer is moving with the movement of the LCCM during cleaning and/or treatment, it does not prevent or inhibit cleaning and/or treatment of surfaces that are in direct contact with the spacer, as this engagement location on the surface is constantly changing. In addition, the motion of the spacer relative to the surface being cleaned/treated may have additional beneficial effect through cleaning and/or stimulation of the contact surface during the cleaning/treatment process, similar to a tooth brushing or gum massaging like action.

In an alternate embodiment, the LCCM could also include abrasive elements such as filaments, textures, polishing elements, additives (silica, etc.), and other geometric elements that could be used for other cleaning and/or treatment requirements as well as ensuring minimal distance between the teeth and LCCM for, but not limited to, treatment, cleaning, and positioning.

In some embodiments, the LCCM may contain a sensing means device and/or switch, which determines if the mouthpiece is in the correct position over the teeth in the oral cavity and which will not allow the device to activate unless this position is verified through the switch/sensor. Also, if the mouthpiece is moved or dislodged from this position during use, it will immediately stop functioning. An override switch can be incorporated during application tray cleaning.

The sensing means can be manual, as in a manual switch(s) such as a membrane switch, or other switches known in the art. Other contact and non-contact sensing means can also be used, such as ultrasonic, Hall (magnetic), frequency, pressure, capacitance, inductance, laser, optical and other sensing means and devices know in the art.

The sensing means would be located in the appliance in such a way that it would measure change or provide a signal when the user positioned the mouthpiece in an acceptable position within the oral cavity, and enabling the device to operate the appropriate cycle.

An alternate and potentially redundant means of determining if the position and orientation of the mouthpiece is correct is to monitor the current and/or power required by the drive motor(s). If the current is above the acceptable range, it is an indication that the mouthpiece may be positioned incorrectly, either blocking delivery of the fluid or the removal/vacuum of fluid from the LCCM. If the current it too low, it is an indication that there is no restriction to vacuum or delivery flow, and again can be indicative of the mouthpiece not being in the correct position within the user's mouth, such as if the user accidently removed the device before the cleaning/treatment cycle was complete, or started the cycle when not positioned correctly within the oral cavity.

The LCCM could be created via a variety of methods such as, but not limited to, machining, injection molding, blow molding, extrusion, compression molding, and/or vacuum forming. It can also be created in conjunction with the manifold, but incorporating the manifold circuitry within the LCC, and/or over-molded onto the manifold to provide a unitary construction with minimal assembly.

In one embodiment, the LCCM may be fabricated separately and then assembled to the manifolds, utilizing any number of assembling and sealing techniques, including adhesives, epoxies, silicones, heat sealing, ultrasonic welding, and hot glue. The LCCM is designed in a way that, when assembled with the manifold, it effectively and efficiently creates the preferred dual manifold design without any additional components.

In certain embodiments, the LCCM can also be designed or used to create the gingival sealing area. In certain embodiments, a vacuum is applied within the LCC, which improves the engagement of the mouthpiece to form a positive seal with the gingival in the oral cavity. In other embodiments, a pressure is applied outside the LCCM, within the oral cavity, which improves the engagement of the mouthpiece to form a positive seal with the gingival in the oral cavity. In yet other embodiments, a denture-like adhesive may be applied around the mouthpiece during the initial use to provide a custom reusable resilient seal when inserted into the oral cavity for a particular user. It would then become resiliently rigid to both conform and provide a positive seal with the guns and on subsequent applications. In another embodiment, the seal could be applied and/or replaced or disposed of after each use.

The directing means also comprises a first manifold for containing the liquid and for providing the liquid to the LCC through the openings of the front inner wall, and a second manifold for containing the liquid and for providing the liquid to the chamber through the openings of the rear inner wall. This design provides a number of different options, depending on what operation is being conducted. For instance, in a cleaning operation, it may be preferable to deliver jets of liquid into the LCC directly onto the teeth from one side of the LCC from the first manifold and then evacuate/pull the liquid around the teeth from the other side of the LCC into the second manifold to provide controlled interdental, gumline and surface cleaning. This flow from the one side of the LCC could be repeated a number of times in a pulsing action before reversing the flow to deliver jets of liquid from the second manifold and evacuating/pulling the liquid through the back side of the teeth into the first manifold for a period of time and/or number of cycles. Such liquid action creates a turbulent, repeatable and reversible flow, thus providing reciprocation of the liquid about the surfaces of the oral cavity.

In a treatment, pre-treatment, or post-treatment operation it may be preferable to deliver the liquid through one or both manifolds simultaneously, flooding the chamber and submerging the teeth for a period of time and then evacuating the chamber after a set period of time through one or both manifolds.

In alternate embodiments, the manifold can be of single manifold design providing pushing and pulling of the liquid through the same sets of jets simultaneously, or can be any number of manifold divisions to provide even greater control of the liquid delivery and removal of the cleaning and liquid treatment. In the multi-manifold also can be designed to have dedicated delivery and removal manifolds. The manifolds can also be designed to be integral to and/or within the LCCM.

The material for the manifold would be a semi-rigid thermoplastic, which would provide the rigidity necessary not to collapse or burst during the controlled flow of the liquids, but to provide some flexibility when fitting within the user's mouth for mouthpiece insertion, sealing/position and removal. To minimize fabrication complexity, number of components and tooling cost, the dual manifold is created when assembled with the LCCM. The manifold could also be multi-component to provide a softer external "feel" to the teeth/gums utilizing a lower durometer elastomeric material, such as, but not limited to, a compatible thermoplastic elastomer (TPE). The manifold could be created via a variety of methods such as, but not limited to machining, injection molding, blow molding, compression molding, or vacuum forming.

The directing means also comprises a first port for conveying the liquid to and from the first manifold and a second port for conveying the liquid to and from the second manifold, and means for providing an effective seal of the directing means within the oral cavity, i.e. a gingival seal. In certain embodiments, the first and second ports may serve both to convey liquid to and from the first and second manifolds and to attach the mouthpiece to the means for providing liquid to the mouthpiece. In other embodiments, the directing means may further include means for attaching the directing means to means for providing liquid to the directing means.

FIG. 1 is a schematic drawing of an embodiment of a method and system according to the present invention. The figure shows system 200, with components including: means for providing reciprocation of liquid in the oral cavity 202, means for directing the liquid onto the plurality of surfaces of the oral cavity, in this instance shown as application tray 100, and liquid supply reservoir 290. Means for providing reciprocation of liquids may include, in this embodiment, delivery/collection device 210, optional reciprocating flow controller 230, tubes 212, 216, and 292 for conveying the liquid throughout the system, and liquid one-way flow valves 214, 218 and 294. Tubes 232 and 234 provide for conveyance of the liquid from reciprocating flow controller 230 to application tray 100.

In some embodiments, delivery/collection device 210 may be a piston pump. Liquid supply reservoir 290 may be made of glass, plastic or metal. Liquid supply reservoir 290 may be integral to system 200 and refillable. In some embodiments, liquid supply reservoir 290 may be a replaceable liquid supply, such as a single or multi-use cartridge, detachably connected to system 200.

In some embodiments, liquid supply reservoir 290 and/or tubes 212, 292, may include a heat source to pre-warm the liquid prior to direction into application tray 100 for application to the surfaces of the oral cavity. The temperature should be maintained within a range effective to provide efficacy and comfort to the user during use.

Application tray 100, discussed in detail herein below, could be integral with, or detachably connected to reciprocating means 202 by way of tubes 232, 234 and further attachment means (not shown). It could be one or two sided with internally, easily cleanable filters for trapping food particles. When positioned within the oral cavity, e.g. about the teeth and gums, tray 100 forms an effective fit or seal against the gums, and includes means to direct liquid against surfaces of the oral cavity, e.g. surfaces of the teeth.

Liquid in liquid supply reservoir 290 flows through tube 292 to delivery/collection device 210. Liquid flow through tube 292 is controlled by one-way flow valve 294. From delivery/collection device 210, liquid flows through tube 212 to reciprocating flow controller 230. One-way flow valve 214 controls the liquid flow through tube 212. Liquid flows from reciprocating flow controller 230 to application tray 100 either through tube 232 or 234, depending on the flow direction setting of flow controller 230. Liquid flows from application tray 100, through either tube 234 or 232 back to reciprocating flow controller 230, and from reciprocating flow controller 230 to delivery/collection device 210, through tube 216. One-way flow valve 218 controls the liquid flow through tube 216.

The actions of delivery/collection device 210 may be controlled by a logic circuit, which may include a program to start the reciprocation cycle, a program to execute the reciprocation cycle, i.e. to cause liquid to be reciprocated about the teeth, thereby providing the beneficial effect to the oral cavity, e.g. cleaning the teeth, a program to empty application tray 100 at the end of the reciprocation cycle, and a self-cleaning cycle to clean the system between uses, or at pre-set or automatic cleaning times.

Though not shown, a face panel with a series of switches and indicator lights may also be incorporated into system 200. Switches may include, but are not limited to, on/off, fill application tray 100, run the reciprocation program, empty system 200, and clean system 200. Indicator, or display, lights include, but are not limited to, power on, charging, reciprocation program running, system emptying, cleaning results or feedback, and self-cleaning cycle in operation. In embodiments where liquid is pre-warmed prior to direction into application tray 100, a display light could be used to indicate that the liquid is at the proper temperature for use.

One method of using system 200 to clean teeth is as follows. In the first step, the user positions application tray 100 in the oral cavity about the teeth and gingival area. The user closes down on tray 100, thereby achieving an effective fit or seal between gums, teeth and tray 100. In use of the system according to the invention, the user pushes a start button initiating the cleaning process. The cleaning process is as follows:

1. Delivery/collection device 210 is activated to begin drawing cleaning liquid from liquid supply reservoir 290 through tube 292 and one-way valve 294.
2. Once delivery/collection device 210 is sufficiently filled, delivery/collection device 210 is activated to begin dispensing cleaning liquid to application tray 100 via tube 212, one-way valve 214, reciprocating flow controller 230, and tube 232. Cleaning liquid will be prevented from flowing through tubes 216 and 292 by one-way flow valves 218 and 294, respectively.
3. Delivery/collection device 210 is activated to begin drawing cleaning liquid from application tray 100 through tube 234, then through reciprocation flow controller 230, then through tube 216 and one-way valve 218. Cleaning liquid will be prevented from flowing through tube 212 by one-way flow valve 214. If there is insufficient cleaning liquid to adequately fill delivery/collection device 210, additional cleaning liquid may be drawn from liquid supply reservoir 290 through tube 292 and one-way valve 294.
4. The direction of the liquid flow is then reversed.
5. To reciprocate the cleaning liquid, steps 2 and 3 are repeated after the flow direction is reversed, cycling cleaning liquid between delivery/collection device 210 and application tray 100, using tubes 234 and 232, respectively.
6. The reciprocation cycle described continues until the time required for cleaning has expired, or the desired numbers of cycles are complete.

It is noted that there may be a delay between steps 2 and 3 (in either or both, directions), allowing a dwell time where the liquid is allowed to contact the teeth without flow.

Figure 2:
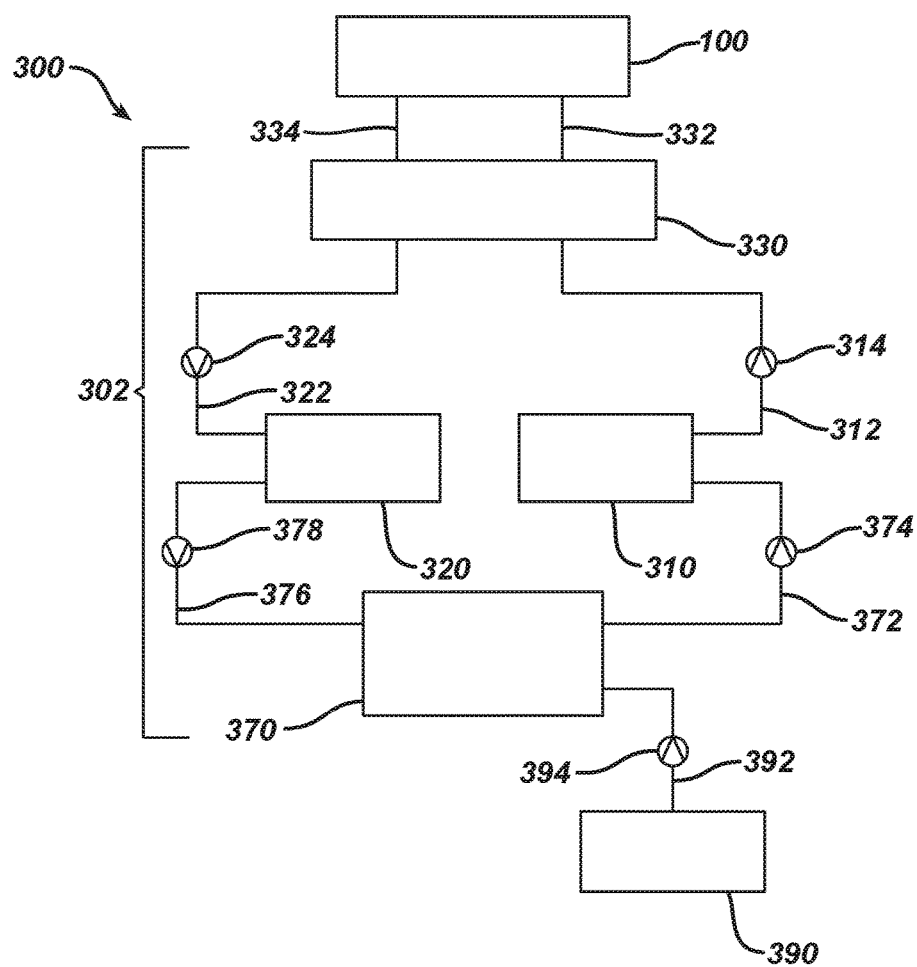
FIG. 2 is a schematic drawing of an alternative embodiment of an apparatus that may be utilized in the present invention.

FIG. 2 is a schematic drawing of a first alternative embodiment of a system and method according to the present invention. The figure shows system 300, with components including: means for providing reciprocation of liquid in the oral cavity 302, liquid reservoir 370, liquid supply reservoir 390, and means for directing liquid onto and about the plurality of surfaces in the oral cavity, in this instance shown as application tray 100. Means for providing reciprocation of fluids may include delivery device 310, collection device 320, optional reciprocating flow controller 330, tubes 312, 322, 372, 376, and 392, and solution one-way flow valves 314, 324, 374, 378, and 394. Tubes 332 and 334 provide for conveyance of the liquid from reciprocating flow controller 330 to application tray 100.

In some embodiments, delivery device 310 and collection device 320 may be individual, single action piston pump. In other embodiments, delivery device 310 and collection device 320 may be housed together as a duel action piston pump. Liquid supply reservoir 390 and liquid reservoir 370 may be made of glass, plastic or metal. Liquid supply reservoir 390 may be integral to system 300 and refillable. In some embodiments, liquid supply reservoir 390 may be a replaceable liquid supply, detachably connected to system 300.

In some embodiments, any of liquid supply reservoir 390, liquid reservoir 370, or tubes 312, 372, 392, may include a heat source to pre-warm liquid prior to direction into application tray 100 for application to the plurality of surfaces in the oral cavity. The temperature should be maintained within a range effective to provide comfort to the user during use.

Application tray 100, could be integral with, or detachably connected to cleaning reciprocating means 302 by way of tubes 332, 334, and other attachment means (not shown).

Liquid in liquid supply reservoir 390 flows through tube 392 to liquid reservoir 370. Liquid in reservoir 370 flows through tube 372 to delivery device 310. Liquid flow through tube 372 may be controlled by one-way flow valve 374. From delivery device 310, liquid flows through tube 312 to reciprocating flow controller 330. One-way flow valve 314 controls the liquid flow through tube 312. Liquid flows from reciprocating flow controller 330 to application tray 100 through tube 332 or 334, depending on the flow direction setting of flow controller 330. Liquid flows from application tray 100, through tube 334 or 332 back to reciprocating flow controller 330, and from reciprocating flow controller 330 to collection device 320, through tube 322. One-way flow valve 324 controls the liquid flow through tube 322. Finally, cleaning liquid flows from collection device 320 to liquid reservoir 370 through tube 376. One-way flow valve 378 controls the liquid flow through tube 376.

The actions of delivery device 310 and collection device 320 are controlled by a logic circuit, which may include a program to the start of the reciprocation cycle, a program to execute the reciprocation cycle, i.e. to cause solution to be reciprocated about the plurality of surfaces of the oral cavity, thereby providing the beneficial effect, a program to empty application tray 100 at the end of the reciprocation cycle, and a self-cleaning cycle to clean the system between uses, or at pre-set or automatic cleaning times.

System 300 may also include switches such as on/off, fill application tray 100, run the cleaning program, empty system 300, and clean system 300, and indicator, or display, lights including, but are not limited to, power on, charging, cycle program running, device emptying, results or feedback, and self-cleaning cycle in operation. In embodiments where liquid is pre-warmed prior to direction into application tray 100, a display light could be used to indicate that the liquid is at the proper temperature for use.

One method of using system 300 to clean teeth is as follows. Prior to use, cleaning liquid in liquid supply chamber 390 flows through tube 392 and one-way valve 394 to cleaning liquid reservoir 370. In some embodiments, liquid supply reservoir 390 is now disconnected from system 300.

In the first step, the user positions application tray 100 in the oral cavity about the teeth and gingival area. The user closes down on tray 100, thereby achieving an effective fit or seal between gums, teeth and tray 100. The user pushes a start button initiating the cleaning process. The cleaning process is as follows:

1. Delivery device 310 is activated to begin drawing cleaning liquid from cleaning liquid reservoir 370 through tube 372 and one-way flow valve 374.
2. Once delivery device 310 is sufficiently filled, delivery device 310 is activated to begin dispensing cleaning liquid to application tray 100 via tube 312, one-way valve 314, reciprocating flow controller 330, and tube 332.
3. Collection device 320 is activated sequentially to or simultaneously with activation of delivery device 310 to begin drawing cleaning liquid from application tray 100 via tube 334, reciprocating flow controller 330, tube 322, and one-way valve 324. Cleaning solution will be prevented from flowing through tube 372 by one-way flow valve 374. In some embodiments, delivery device 310 and collection device 320 are controlled by a logic circuit to work in concert so that an equal volumetric flow of cleaning liquid is dispensed from delivery device 310 and drawn into collection device 320.
4. Collection device 320 is activated to begin dispensing cleaning solution to cleaning liquid reservoir 370 via tube 376 and one-way valve 378. Cleaning liquid will be prevented from flowing through tube 322 by one-way flow valve 324. Delivery device 310 is also activated to begin drawing cleaning liquid from cleaning liquid reservoir 370 through tube 372 and one-way flow valve 374.
5. To reciprocate the cleaning liquid, steps 2 and 3 are repeated after the flow direction is reversed, cycling cleaning liquid between delivery/collection device 320 and application tray 100, using tubes 334 and 332, respectively.
6. To cycle cleaning liquid, steps 2 through 4 are repeated, cycling cleaning liquid between cleaning liquid reservoir 370 and application tray 100
7. The process continues to run until the time required for cleaning has expired, or the desired numbers of cycles are complete.

Figure 3:
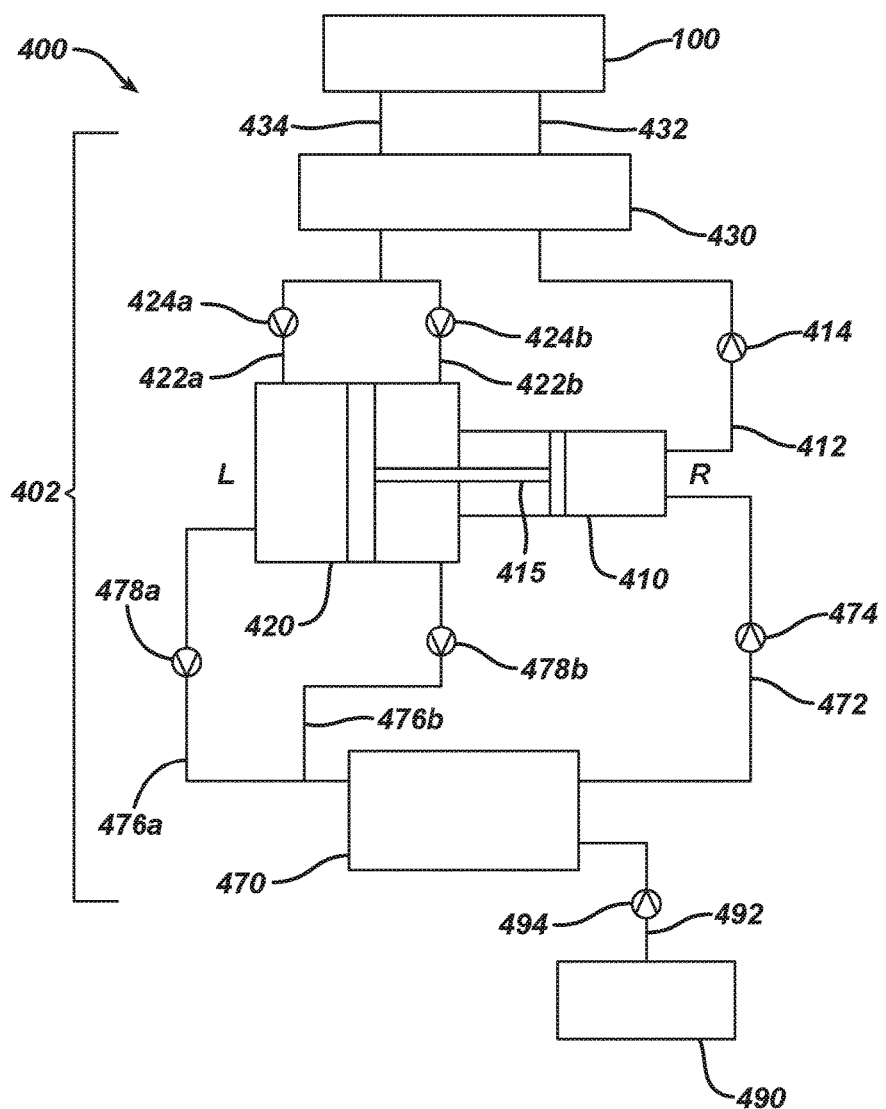
FIG. 3 is a schematic drawing of another alternative embodiment of an apparatus that may be utilized in the present invention.

FIG. 3 is a schematic drawing of a second alternative embodiment of a system according to the present invention. The figure shows system 400, with components including: means for providing reciprocation of liquids in the oral cavity 402, liquid reservoir 470, liquid supply reservoir 490, and means for directing the liquid onto the plurality of surfaces of the oral cavity, in this instance shown as application tray 100. Means for providing reciprocation 402 may include delivery device 410, collection device 420, optional reciprocating flow controller 430, tubes 412, 422a, 422b, 472, 476, and 492, and solution one-way flow valves 414, 424a, 424b, 474, 478, and 494. Tubes 432 and 434 provide for conveyance of the liquid from reciprocating flow controller 430 to application tray 100.

In the present embodiment, delivery device 410 and collection device 420 are housed together as a duel action piston pump, with common piston 415. Liquid supply reservoir 490 and liquid reservoir 470, may be made of glass, plastic, or metal. Liquid supply reservoir 490 may be integral to system 400 and refillable. In some embodiments, liquid supply chamber 490 may be a replaceable liquid supply, detachably connected to system 400.

In some embodiments, any of liquid supply chamber 490, liquid reservoir 470, or tubes 412, 472, 492, may include a heat source to pre-warm cleaning solution prior to direction into application tray 100 for application to the teeth. The temperature should be maintained within a range effective to provide comfort to the user during use.

Application tray 100 could be integral with, or detachably connected to reciprocating means 402 by way of tubes 432, 434 and other attachment means (not shown).

Liquid in liquid supply chamber 490 flows through tube 492 to liquid reservoir 470. Liquid in reservoir 470 flows through tube 472 to delivery device 410. Liquid flow through tube 472 is controlled by one-way flow valve 474. From delivery device 410, liquid flows through tube 412 to reciprocating flow controller 430. One-way flow valve 414 controls the liquid flow through tube 412. Liquid flows from reciprocating flow controller 430 to application tray 100 through tube 432 or tube 434, depending on the flow direction. Liquid flows from application tray 100, through tube 434 or tube 432, again depending on the flow direction, back to reciprocating flow controller 430, and from reciprocating flow controller 430 to collection device 420, through tubes 422a and 422b. One-way flow valves 424a and 424b control the liquid flow through the tubes. Finally, liquid flows from collection device 420 to liquid reservoir 470 through tubes 476a and 476b. One-way flow valves 478a and 478b control the liquid flow through the tubes.

The actions of delivery device 410 and collection device 420 are controlled by a logic circuit, which may include a program to the start reciprocation cycle, a program to execute the reciprocation cycle, i.e. to cause solution to be reciprocated about the plurality of the surfaces of the oral cavity, thereby providing the beneficial effect, a program to empty application tray 100 at the end of the cycle, and a self-cleaning cycle to clean the system between uses, or at pre-set or automatic cleaning times.

System 400 may also include switches such as on/off, fill application tray 100, execute cleaning process, empty system 400, and clean system 400, and indicator, or display, lights including, but are not limited to, power on, charging, reciprocation program running, device emptying, and self-cleaning cycle in operation. In embodiments where liquid is pre-warmed prior to direction into application tray 100, a display light could be used to indicate that the liquid is at the proper temperature for use.

One method of using system 400 to clean teeth is as follows. Prior to use, cleaning liquid in liquid supply reservoir 490 flows through tube 492 and one-way valve 494 to cleaning liquid reservoir 470. In some embodiments, liquid supply reservoir 490 is now disconnected from system 400.

In the first step, the user positions application tray 100 in the oral cavity about the teeth and gingival area. The user bites down on tray 100, thereby achieving an effective fit or seal between gums, teeth and tray 100. The user pushes a start button initiating the cleaning process. The cleaning process is as follows:
1. Piston 415 is activated to begin drawing cleaning liquid to delivery device 410 from cleaning liquid reservoir 470 through tube 472 and one-way flow valve 474. To accomplish this, piston 415 translates from right to left ("R" to "L" on FIG. 3).
2. Once delivery device 410 is sufficiently filled, delivery device 410 is activated to begin dispensing cleaning liquid to application tray 100 via tube 412, one-way valve 414, reciprocating flow controller 430, and tube 432. To accomplish this, piston 415 translates from left to right ("L" to "R" on FIG. 3). The "L" to "R" motion of piston 415 causes collection device 420 to begin drawing cleaning liquid from application tray 100 via tube 434, reciprocating flow controller 430, tube 422a, and one-way valve 424a. Cleaning liquid will be prevented from flowing through tubes 472 and 422a, by one-way flow valves 474 and 424b. Any excess cleaning liquid in collection device 420 will begin dispensing to cleaning liquid reservoir 470 via tube 476b and one-way valve 478b. Cleaning liquid will be prevented from flowing through tube 422b by one-way flow valve 424b.
3. To cycle cleaning solution, steps 1 and 2 are repeated, cycling cleaning liquid between cleaning solution reservoir 470 and application tray 100
4. The process continues to run until the time required for cleaning has expired, or the desired numbers of cycles are complete.

Each embodiment described in FIG. 1, FIG. 2, and FIG. 3 may include reciprocating flow controller (230, 330, 430 in FIG. 1, FIG. 2, FIG. 3, respectively). A perspective drawing and an exploded view of an embodiment of a reciprocating flow controller according to the present invention is shown in FIG. 6a and FIG. 6b, respectively. The figures show reciprocating flow controller 500 with housing 510 and flow diverter 520. Housing 510 has ports 514, 515, 516, and 517. Flow diverter 520 occupies the space defined by the inner walls of housing 510, and has panel 522 for diverting liquid flow, and position adjuster 524.

Figure 4A:
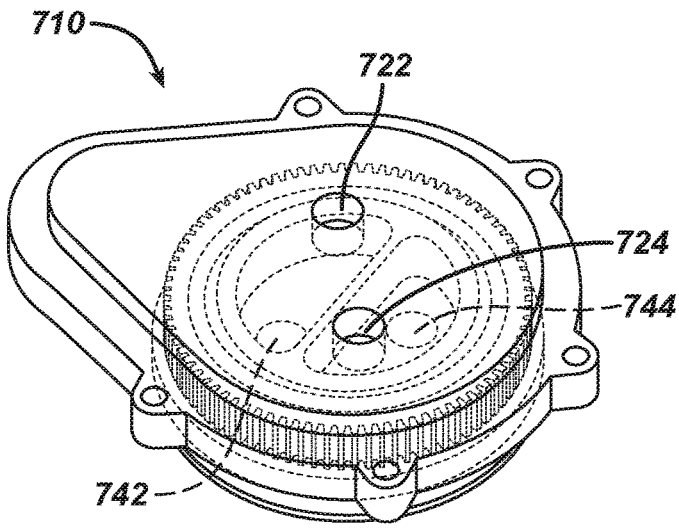
FIG. 4a is a perspective drawing of an embodiment of a reciprocating flow controller that may be utilized in the present invention.
Figure 4B:
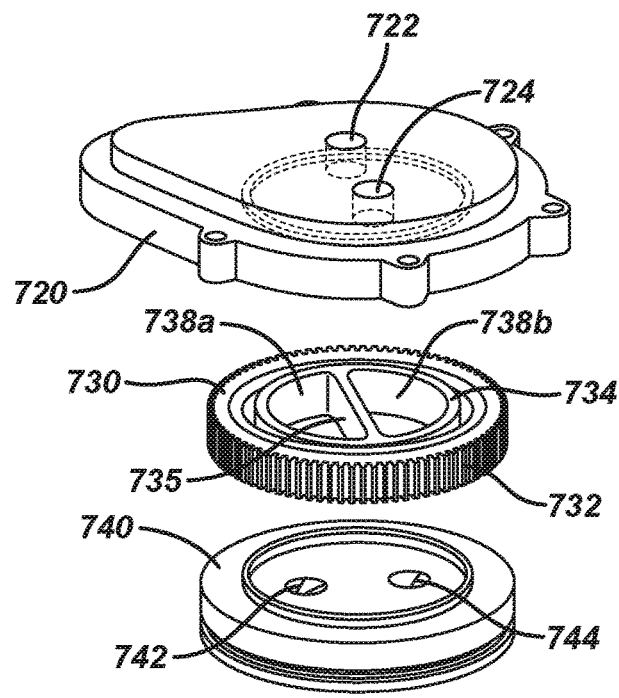

A perspective drawing and an exploded view of an alternate embodiment of a reciprocating flow controller according to the present invention is shown in FIG. 4a and FIG. 4b, respectively. The figures show reciprocating flow controller 710 with cap 720, flow diverter disk 730, and base 740. Cap 720 has cap ports 722 and 724. Base 740 has base ports 742 and 744. Flow diverter disk 730 is disposed between cap 720 and base 740, and has panel 735 for diverting liquid flow, and position adjuster 732 in the form of a gear.

Figure 4C:
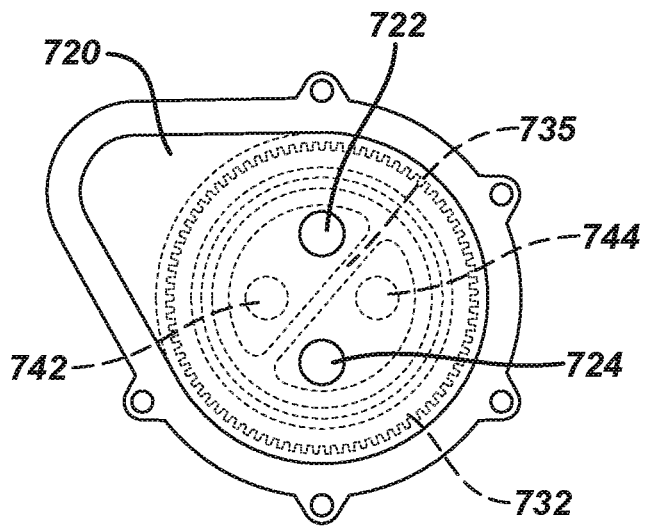
FIG. 4c is a top view of the reciprocating flow controller of FIG. 4a in its first position.

FIG. 4c is a top view of reciprocating flow controller 710 in its first position. In this position, incoming liquid, such as liquid in tube 212 of FIG. 1, enters reciprocating flow controller 710 through base port 742. The liquid exits reciprocating flow controller 710 through cap port 722, such as liquid in tube 232 of FIG. 1. Returning liquid, such as liquid in tube 234 of FIG. 1, reenters reciprocating flow controller 710 through cap port 724. The liquid exits reciprocating flow controller 710 through base port 744, such as liquid in tube 216 of FIG. 1.

Figure 4D:
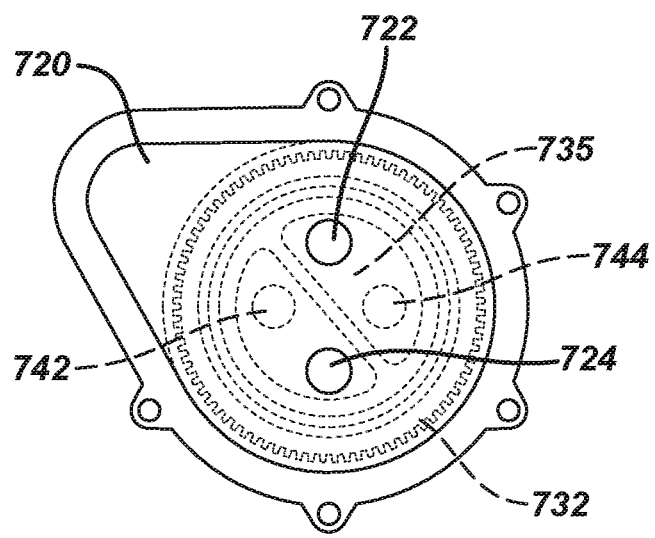
FIG. 4d is a top view of the reciprocating flow controller of FIG. 4a in its second position.

FIG. 4d is a top view of reciprocating flow controller 710 in its second position. In this position, incoming liquid, such as liquid in tube 212 of FIG. 1, enters reciprocating flow controller 710 through base port 742. The liquid exits reciprocating flow controller 710 through cap port 724 such as liquid in tube 234 of FIG. 1. Returning liquid, such as liquid in tube 232 of FIG. 1, reenters reciprocating flow controller 710 through cap port 722. The liquid exits reciprocating flow controller 710 through base port 744, such as liquid in tube 216 of FIG. 1.

Reciprocation of liquid in application tray 100 of FIG. 1 is achieved by switching reciprocating flow controller 710 between its first and second positions. It has been found that the width of panel 735 relative to the diameters of cap ports 722 and 724 and base ports 742 and 744 is critical to the performance of reciprocating flow controller 710. If the width of panel 735 is equal to or greater than any of the diameters, then one or more of cap ports 722 and 724 or base ports 742 and 744 may be blocked, or isolated, during part of the reciprocation, resulting in suboptimal performance or device failure. A channel may be located in panel 735 to avoid this condition.

The oral hygiene system may be comprised of several major components including, but not limited to, a base station, a hand piece for containing means for providing reciprocation of liquid about the plurality of surfaces within the oral cavity, and the application tray, or mouthpiece. The system is suitable for in-home use and adapted to direct liquid onto a plurality of surfaces of a tooth simultaneously. The device cleans teeth and removes plaque using cleaning solution that is reciprocated back and forth creating a cleaning cycle and minimizing cleaning solution used. The device could be hand held, or may be in the form of a table or counter-top device.

The base station will charge a rechargeable battery in the hand piece, hold liquid reservoirs, house diagnostic components, provide feedback to the user, and potentially clean the mouthpiece.

The hand piece will have a powered pump that will deliver liquid from the reservoir to the mouthpiece. The direction of flow may be reciprocated with liquid control valving, by a specialized pump (reversing its direction, etc), reversible check valves, or other similar means. The cycle time and flow velocity for each stage of the cycle will be variable and in some embodiments, be customized to each individual user. The hand piece will perform a filling process, and a cleaning and/or purging process. The hand piece and/or base station may provide feedback to the user for each stage of the process and potentially report diagnostic information.

The hand piece will be aesthetically pleasing and have a grip/feel comfortable for the user's hand. The weight and balance will be well suited to comfortable and efficient use while giving a high quality feel. Finger grips and/or touch points will be appropriately located for comfort, grip, feel, and assistance in proper orientation and grip location of the hand piece. The base station will also be aesthetically pleasing and allow the hand piece to easily and securely dock into position. The base station may or may not lock the hand piece into position once it's docked.

Figure 5:
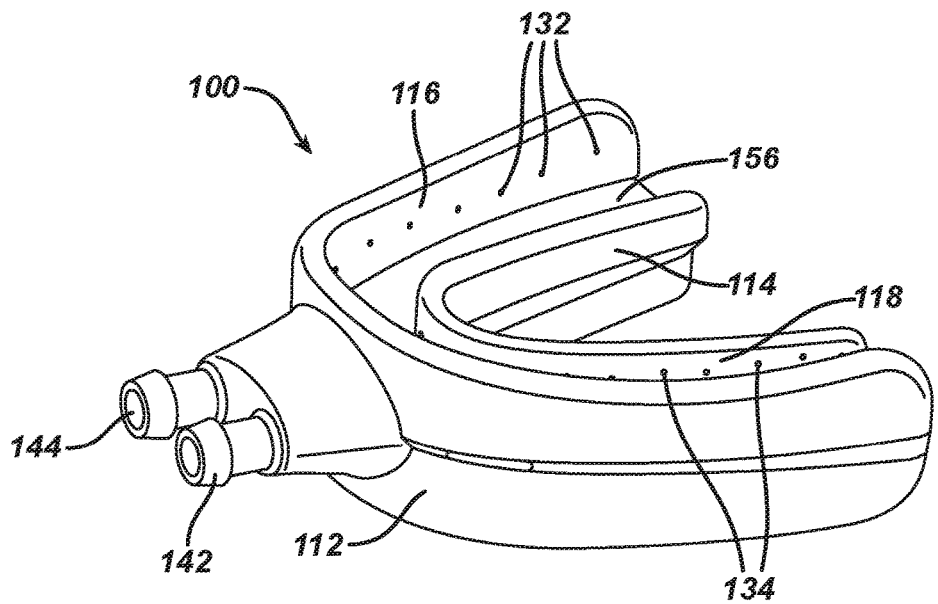
FIG. 5 is a top front perspective view of a first embodiment of an application tray that may be utilized in the present invention.
Figure 6:
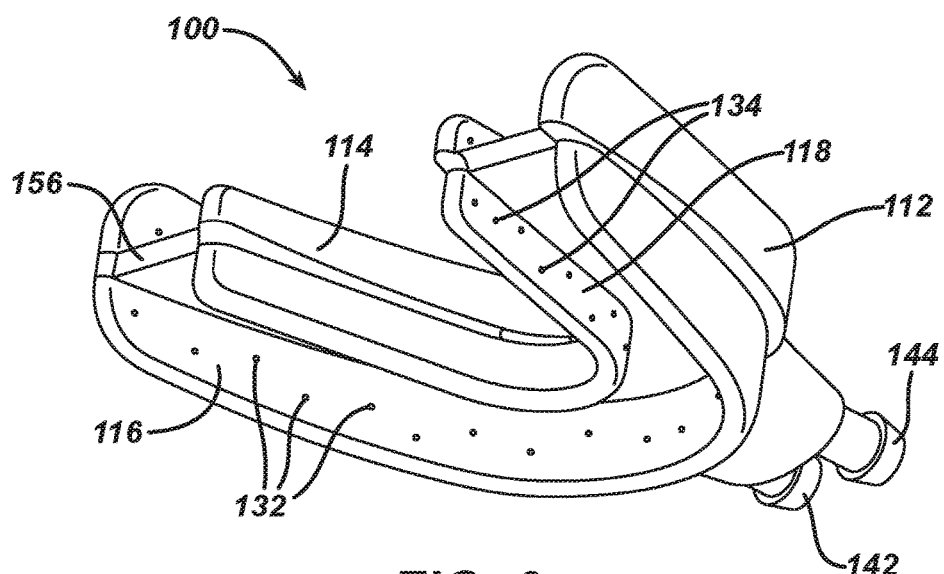
FIG. 6 is a bottom rear perspective view of the embodiment of the application tray of FIG. 5.

FIG. 5 is a top perspective view of a first embodiment of means for directing liquid onto a plurality of surfaces in the oral cavity, e.g. an application tray 100, according to the present invention. FIG. 6 is a bottom perspective view of the application tray 100 of FIG. 5. The figures show application tray 100 with outer front wall 112, outer back wall 114, inner front wall 116, inner back wall 118, and base membrane, e.g. bite plate, 156. Inner front wall jet slots 132 are located on inner front wall 116, while inner back wall jet slots 134 are located on inner back wall 118. The inner front wall jet slots 132 and inner back wall jet slots 134 shown in FIGS. 5 and 6 are only one embodiment of jet slot configuration. First port 142 and second port 144 enter application tray 100 through outer front wall 112.

FIGS. 5 and 6 depict an embodiment of an application tray 100 in which the user's top and bottom teeth and/or gingival area are substantially simultaneously contacted with liquid to provide the desired beneficial effect. It should be understood that in other embodiments, application tray 100 may be designed to clean and/or treat only the top or bottom teeth and/or gingival area of the user.

Figure 7:
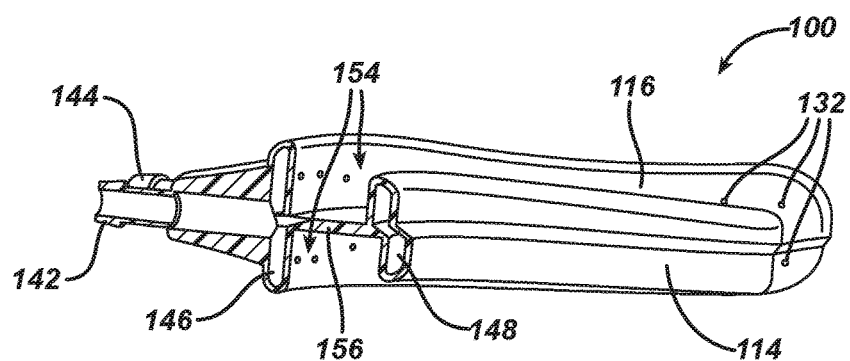
FIG. 7 is a vertical sectional view of the application tray of FIG. 5.
Figure 8:
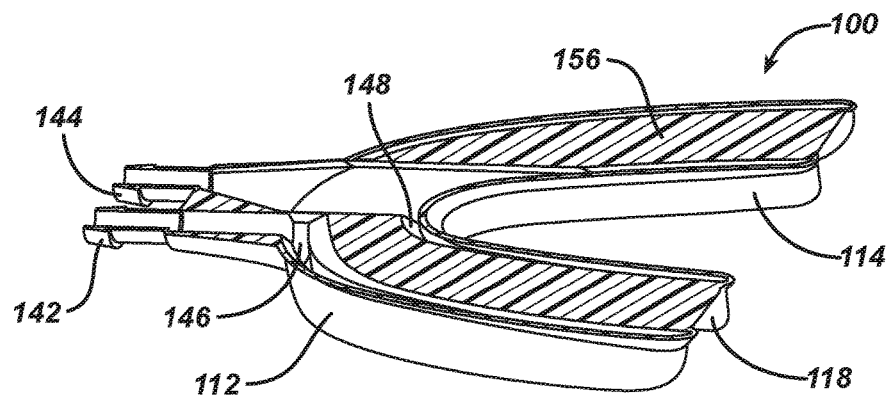
FIG. 8 is a horizontal sectional view of the application tray of FIG. 5.

FIGS. 7 and 8 are vertical and horizontal, respectively, sectional views of the application tray 100 of FIG. 5. The figures show first manifold 146, defined as the space bordered by outer front wall 112 and inner front wall 116. Second manifold 148 is defined as the space bordered by outer back wall 114 and inner back wall 118. The liquid-contacting chamber (LCC) 154 is defined by inner front wall 116, inner back wall 118, and base membrane 156.

In one embodiment of an operation, liquid enters first manifold 146 through first port 142 by pressure and then enters LCC 154 through inner front wall jet slots 132. A vacuum is pulled on second port 144 to pull the liquid through inner back wall jet slots 134, into second manifold 148 and finally into second port 144. In this embodiment, jets of liquid are first directed onto the front surfaces of the teeth and/or gingival area from one side of the LCC 154, directed through, between, and around the surfaces of the teeth and/or gingival area from the other side of LCC 154 into the second manifold to provide controlled interdental, gumline, surface and/or gingival area cleaning or treatment. Next, the flow in the manifolds is reversed. Cleaning liquid enters second manifold 148 through second port 144 by pressure and then enters LCC 154 through inner back wall jet slots 134. A vacuum is pulled on first port 142 to pull the liquid through inner front wall jet slots 132, into first manifold 146 and finally into first port 142. In the second portion of this embodiment, jets of liquid are directed onto the back surfaces of the teeth and/or gingival area, and directed through, between, and around the surfaces of the teeth and/or gingival area. The alternating of pressure/vacuum through a number of cycles creates a turbulent, repeatable and reversible flow to provide reciprocation of liquid about the plurality of surfaces of the oral cavity to substantially simultaneously contact the surfaces of the oral cavity with liquid, thereby providing the desired beneficial effect.

In another embodiment it may be preferable to deliver the liquid through one or both manifolds simultaneously, flooding LCC 154, submerging the teeth for a period of time and then evacuating the LCC 154 after a set period of time through one or both manifolds. Here, cleaning or treating liquid simultaneously enters first manifold 146 through first port 142, and second manifold 148 through second port 144 by pressure and then enters LCC 154 simultaneously through inner front wall jet slots 132 and inner back wall jet slots 134. To evacuate LCC 154, a vacuum is simultaneously pulled on first manifold 146 through first port 142, and second manifold 148 through second port 144. Cleaning or treatment liquid is pulled through inner front wall jet slots 132 and inner back wall jet slots 134, into first manifold 146 and second manifold 148.

It is also possible to deliver different liquid compositions to first manifold 146 and second manifold 148. The different liquid compositions could then combine in the LCC for improved cleaning efficacy or treatment effects.

Figure 9:
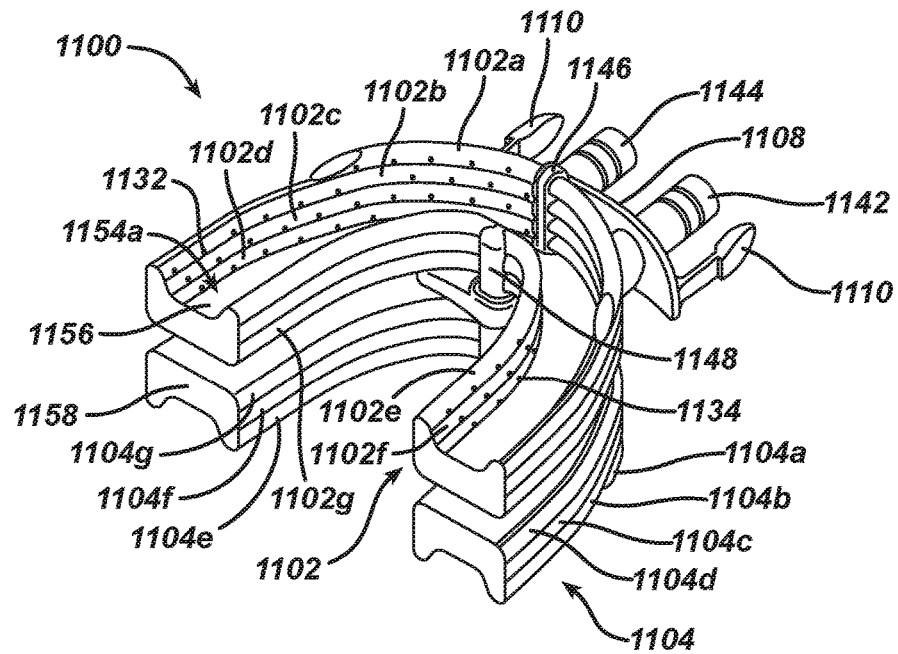
FIG. 9 is a top back perspective view of a second embodiment of an application tray that may be utilized in the present invention.
Figure 10:
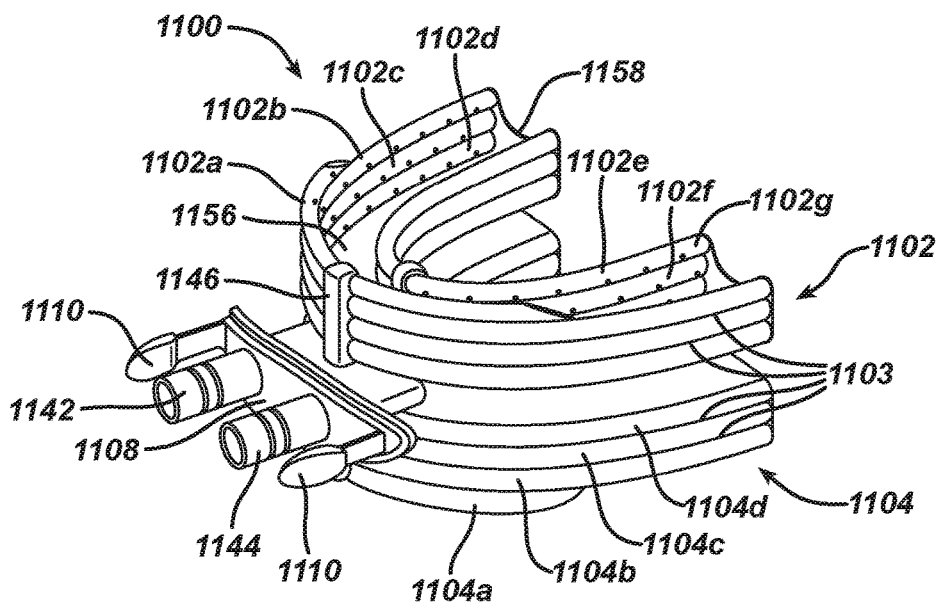
FIG. 10 is a top front perspective view of the embodiment of the application tray of FIG. 9.
Figure 11:
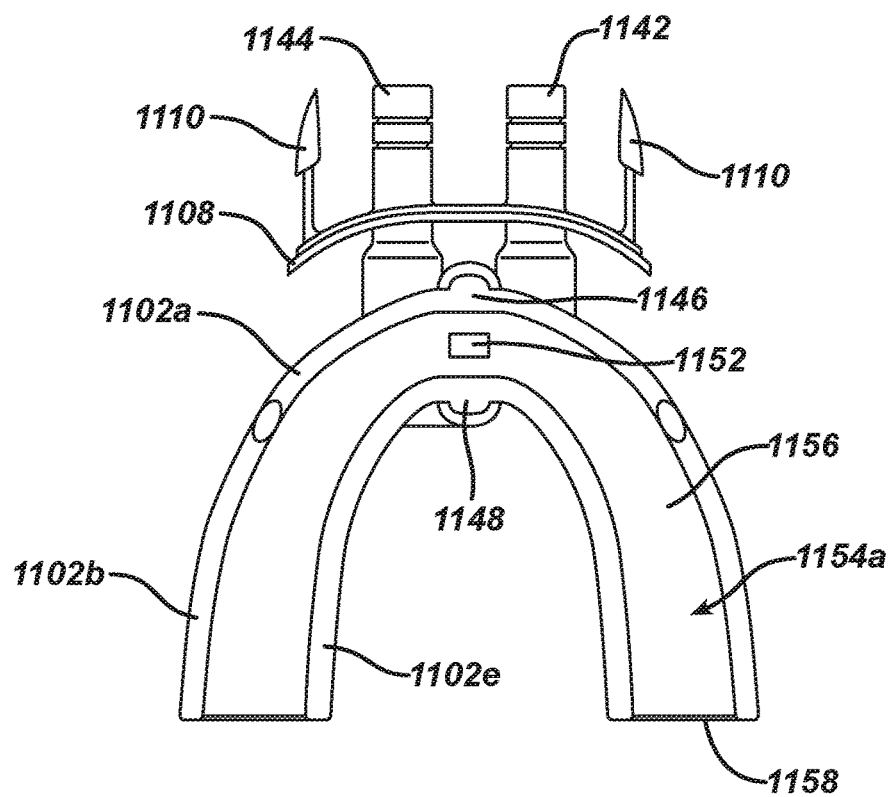
FIG. 11 is a top view of the application tray of FIG. 9.

FIG. 9 is a top, rear perspective view of a second embodiment of an application tray 1100 according to the present invention. FIG. 10 is a top, front perspective view of the application tray 1100 of FIG. 9, while FIG. 11 is a top view of the application tray of FIG. 9. The figures show application tray 1100 with top piece 1102, bottom piece 1104, first port 1142, second port 1144, and support plate 1108 fixedly attached to the front of said application tray. First port 1142 and second port 1144 enter application tray 1100 and extend through support plate 1108. FIG. 11 also shows optional sensing means 1152 which determines if the mouthpiece is in the correct position over the teeth in the oral cavity.

Optional quick disconnect structures, e.g. barbs, 1110 are attached to support plate 1108, allowing application tray 1100 to be quickly and easily attached to and then disconnected from means for providing liquid to the application tray. The housing would include structure effective to receive such quick disconnect barbs, or similar quick disconnect structure, in attachable engagement, to detachably connect the application tray to the housing. The quick disconnect option could be used to replace used or worn application trays, or to change application trays for different users. In some embodiments, a single user may change application trays to change the flow characteristics for different options, such as number of cleaning nozzles, nozzle velocity, spray pattern, and locations, coverage area, etc.

FIGS. 9 to 12 depict an embodiment of an application tray 1100 in which the user's top and bottom teeth and/or gingival area are substantially simultaneously contacted with liquid. It should be understood that in other embodiments, application tray 1100 may be designed to contact only the top or bottom teeth or gingival area of the user with liquid.

Top piece 1102 has front liquid lumens 1102a, 1102b, 1102c, and 1102d, back liquid lumens 1102e, 1102f, and 1102g, first manifold 1146, second manifold 1148, base membrane 1156, and back gum-sealing membrane 1158. Front liquid lumens 1102a, 1102b, 1102c, and 1102d are all connected by first manifold 1146, and optionally (as shown on FIGS. 9 to 12), connected to each other along all, or part of, their length. Likewise, back liquid lumens 1102e, 1102f, and 1102g, are all connected by second manifold 1148, and optionally, connected to each other along all, or part of, their length.

Bottom piece 1104, may be a mirror image of top piece 1102, and has front liquid lumens 1104a, 1104b, 1104c, and 1104d, back liquid lumens 1104e, 1104f, and 1104g, first manifold 1146, second manifold 1148, base membrane 1156, and back gum-sealing membrane 1158. Front liquid lumens 1104a, 1104b, 1104c, and 1104d are all connected by first manifold 1146, and optionally (as shown on FIGS. 9 to 12), connected to each other along all, or part of, their length. Likewise, back liquid lumens 1104e, 1104f, and 1104g, are all connected by second manifold 1148, and optionally, connected to each other along all, or part of, their length.

Figure 12:
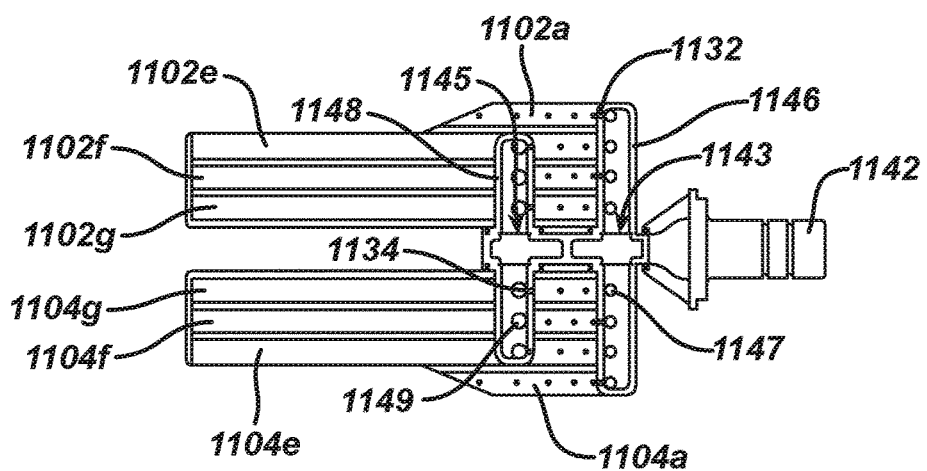
FIG. 12 is a cut-away view of the application tray of FIG. 9.

Though FIGS. 9 and 12 show top piece 1102 with four front liquid lumens (1102a, 1102b, 1102c, and 1102d) and three back liquid lumens (1102e, 1102f, and 1102g), top piece 1102 may also be formed with two, three, five, six, or even seven front or back liquid lumens. Likewise, bottom piece 1104 is shown with four front liquid lumens (1104a, 1104b, 1104c, and 1104d) and three back liquid lumens (1104e, 1104f, and 1104g), bottom piece 1104 may also be formed with two, three, five, six, or even seven front or back liquid lumens.

The liquid-contacting chamber ((LCC) 1154a, mentioned above, is located in top piece 1102, defined by front liquid lumens (1102a, 1102b, 1102c, and 1102d), back liquid lumens (1102e, 1102f, and 1102g), base membrane 1156, and back gum-sealing membrane 1158. Though not shown, bottom piece 1104 also has a LCC 1154b, defined by front liquid lumens (1104a, 1104b, 1104c, and 1104d), back liquid lumens (1104e, 1104f, and 1104g), base membrane 1156, and back gum-sealing membrane 1158.

The multi-lumen design provides bidirectional or dedicated lumens for flow and vacuum that are self-reinforcing and therefore do not collapse under vacuum or rupture under pressure while in use, maximizing the structural integrity, while minimizing the size of the overall application tray 1100 for user comfort during insertion, in-use, and upon removal. This decreased size also serves to provide an enhanced effective seal of the application tray in the oral cavity.

If the multiple lumens (1102a, 1102b, 1102c, 1102d, 1102e, 1102f, 1102g, 1104a, 1104b, 1104c, 1104d, 1104e, 1104f, and 1104g) are connected as described above, they form a lumen hinge sections (1103 on FIG. 10). This may result in the multi-lumen design providing conformance in the X, Y and Z directions, due to the flexibility of lumen hinge sections 1103 between each lumen. This design allows effective and feasible conformance to a variety of different users teeth and gum topography, providing the effective gum sealing without irritating the gums and allowing dynamic positioning of the liquid cleaning jets around each of the teeth to obtain proximal and interdental cleaning action. The multiple lumens are also attached to the first manifold 1146 and second manifold 1148. This creates a secondary flexible joint providing two additional degrees of motion for the adjusting to different bite architectures that may be encountered.

The back gum-sealing membrane 1158 proves a flexible and universal sealing mechanism to minimize leakage into the oral cavity while redirecting flow onto and around teeth, to maximize treatment/cleaning area to get to hard-to-reach-places (HTRP). The membrane can provide an elastic function across the lumen longitudinal axis to form around the teeth and gums.

Base membrane 1156 provides the flexibility required for effective fit or sealing within the oral cavity and allowing redirection and flow of jets back towards the teeth and/or gingival surfaces.

Optionally, application tray 1100 could also include gum-sealing component if required, which could be attached to the front liquid lumens 1102a, 1102b, 1104a, and 1104b, and back liquid lumens 1102e and 1104e (member furthest from teeth).

Optionally, frictional elements, such as filament tufts, could also be placed or secured through any of the lumen hinge sections 1103 without significantly increasing the size of application tray 1100, or impacting user comfort or liquid flow in the application tray 1100.

Inner front wall jet slots 1132 are located on inner front wall of top piece 1102 and bottom piece 1104, while inner back wall jet slots 1134 are located on inner back wall of top piece 1102 and bottom piece 1104. Though only one inner front wall jet slot 1132 and inner back wall jet slot 1134 are shown in FIGS. 9 to 12, the number, shape and size of inner front wall jet slots 1132 and inner back wall jet slots 1134 affect the cleaning of the teeth and gums, and can be designed to direct jets of cleaning liquid in a variety of spray patterns. The inner front wall jet slots 1132 and inner back wall jet slots 1134 shown in FIGS. 9 to 12 are only one embodiment of jet slot configuration.

FIGS. 9 and 10 depict an embodiment of an application tray 1100 in which surfaces of the users top and bottom teeth and/or gingival area are substantially simultaneously contacted by liquid to provide the desired beneficial effect. It should be understood that, in other embodiments, application tray 1100 may be designed to contact only the top or bottom teeth and/or gingival area of the user.

FIG. 12 is a cut-away view of the application tray 1100 of FIG. 9. The figure shows first manifold 1146 and second manifold 1148. In one embodiment of a cleaning operation, cleaning liquid is pumped through first port 1142, and enters first manifold 1146 through first flow diverter 1143. Liquid enters front liquid lumens 1102a, 1102b, 1102c, 1102d, 1104a, 1104b, 1104c and 1104d through front liquid lumen ports 1147. The cleaning liquid then enters LCCs 1154a and 1154b through inner front wall jet slots 1132. A vacuum is pulled on second manifold feeder 1144 to pull the cleaning liquid through inner back wall jet slots 1134, into back liquid lumens 1102e, 1102f, 1102g, 1104e, 1104f, and 1104g. The liquid enters second manifold 1148 through back liquid lumen ports 1149, then through second flow diverter 1145, and finally into second manifold feeder 1144.

In this embodiment, jets of cleaning liquid are first directed from first manifold 1146 to the front surfaces of the teeth and/or gingival area from one side of the LCCs, directed through, between, and around the surfaces of the teeth and/or gingival area from the other side of the LCCs into the second manifold 1148 to provide controlled interdental, gumline, surface and/or gingival area cleaning or treatment.

Next, the flow in the manifolds is reversed. Cleaning liquid is pumped through second port 1144, and enters second manifold 1148 through second flow diverter 1145. Liquid enters back liquid lumens 1102e, 1102f, 1102g, 1104e, 1104f, and 1104g through back liquid lumen ports 1149. The cleaning liquid then enters LCCs 1154a and 1154b through inner back wall jet slots 1134. A vacuum is pulled on first port 1142 to pull the cleaning liquid through inner front wall jet slots 1132, into front liquid lumens 1102a, 1102b, 1102c, 1102d, 1104a, 1104b, 1104c and 1104d. The liquid enters first manifold 1146 through front liquid lumen ports 1147, then through first flow diverter 1143, and finally into first port 1144.

In the second portion of this embodiment, jets of cleaning liquid are directed onto the back surfaces of the teeth and/or gingival area, and directed through, between, and around surfaces of the teeth and/or gingival area. The alternating of pressure/vacuum through a number of cycles creates a turbulent, repeatable and reversible flow to provide reciprocation of liquid about the plurality of surfaces of the oral cavity to substantially simultaneously contact the surfaces of the oral cavity with liquid, thereby providing the desired beneficial effect.

In another embodiment it may be preferable to deliver the liquid through one or both manifolds simultaneously, flooding LLCs 1154a and 1154b, submerging the teeth for a period of time and then evacuating the LCCs after a set period of time through one or both manifolds. Here, cleaning or treating liquid is simultaneously pumped through first port 1142 into first manifold 1146 via first flow diverter 1143, and through second port 1144 into second manifold 1148 via second flow diverter 1145. Liquid then simultaneously enters front liquid lumens 1102a, 1102b, 1102c, 1102d, 1104a, 1104b, 1104c and 1104d through front liquid lumen ports 1147, and back liquid lumens 1102e, 1102f, 1102g, 1104e, 1104f, and 1104g through back liquid lumen ports 1149. The cleaning liquid then enters LCCs 1154a and 1154b through inner front wall jet slots 1132 and inner back wall jet slots 1134. To evacuate the LCCs, a vacuum is simultaneously pulled on first manifold 1146 through first port 1142, and second manifold 1148 through second port 1144. Cleaning or treatment liquid is pulled through inner front wall jet slots 1132 and inner back wall jet slots 1134, into first manifold 146 and second manifold 148.

It is also possible to deliver different liquid compositions to first manifold 1146 and second manifold 1148. The different liquid compositions would then combine in the LCC for improved cleaning efficacy or treatment effects. In the dual manifold design it may be preferable to supply each manifold from a separate liquid supply reservoir, such as in a dual action piston pump configuration, where one supply line connects to supply first manifold 1146 and the other piston supply line provides and removes liquid from second manifold 1148, e.g. when one manifold is being supplied with liquid the second manifold is removing liquid, and vice versa.

In other embodiments, valves can be placed at front liquid lumen ports 1147 of front liquid lumens 1102a, 1102b, 1102c, 1102d, 1104a, 1104b, 1104c and 1104d, or at back liquid lumen ports 1149 of back liquid lumens 1102e, 1102f, 1102g, 1104e, 1104f, and 1104g to provide improved function by allowing lumens to engage at different times (at different points in the cleaning/treatment cycle), at pulsed intervals. As an example, in one embodiment, not all lumens engage in the liquid pumping/vacuum function. Here, front liquid lumens 1102a and 1104a, and back liquid lumens 1102e and 1104e, which primarily engage the gums, only engage in the liquid vacuum function. This would help prevent liquid from leaking into the oral cavity. Valving also allows for variable flow, allowing a decreased resistance to the liquid vacuum function, or allowing increased pumping, and therefore liquid velocity, during liquid delivery.

In still other embodiments, individual inner front wall jet slots 1132 or inner back wall jet slots 1134 may have integrated one-way valves, such as duckbill valves or umbrella valves, to allow flow only in one direction out of those particular jets. This may be effective to increase vacuum relative to pressure/delivery in the LCC.

In some embodiment, the motion of the frictional elements discussed above, relative to the teeth, could be applied by a single or combination of mechanisms including, by not limited to, the liquid (via the jet slots or via turbulence of flow); movement of the membrane via the pulsing of the flexible application tray 1100; an external vibrational mechanism to vibrate the frictional elements; linear and or rotational movement of the application tray 1100 around the teeth through user jaw motion or external driving means.

In other embodiments, a conformable substance, such as gel, may be disposed near the back gum-sealing membrane 1158, allowing application tray 1100 to comfortably fit against the back of the mouth. Alternatively, the end of application tray 1100 may have a mechanism or attachment to extend or decrease the length of the mouthpiece to the proper length for each individual user, providing a semi-custom fit.

Manufacturing of the multi-lumen design is feasible utilizing existing available manufacturing and assembly processes such as extrusion, injection, vacuum, blow, or compression molding. Other feasible techniques include rapid prototyping techniques such as 3D printing and other additive techniques, as well as subtractive techniques.

The application tray may be custom manufactured for each individual user, or customizable by the individual user prior to use. For custom manufacture of the application tray, vacuum form molds can be created directly or indirectly from user teeth and gingival impressions, which create a model of the teeth which can then be modified to create required clearances and flow channels. These vacuum form molds can be created at low cost utilizing CAD and rapid prototyping processes.

One manufacturing method is to create individual component shells through vacuum forming. Low cost methods allow vacuuming forming of very thin wall structures. The component geometry is designed to provide the interlocking features and structural geometry to allow minimization of the size of the application tray. When assembled, the manufactured components form the necessary manifolds and flow structure (bidirectional and/or dedicated manifolds) to provide the required performance characteristics for treating/cleaning the teeth.

Customized mouthpieces are based on the user's teeth geometry, therefore creating a consistent distance between the mouthpiece and teeth may provide a more consistent cleaning/treating experience. The materials for each of the two-piece shell may be different, therefore allowing for softer material (on the inside shell) where it contacts teeth/gums and harder material on the outside shell to maintain rigidity and the overall shape.

For customizable application trays, tray pre-forms (similar to sport mouth guards or teeth grinding appliances) containing pre-manufactured manifolds, nozzles and channels are mass manufactured. The tray pre-forms can be created through a variety of known manufacturing techniques including, but not limited to, blow molding, vacuum forming, injection and/or compression molding. The material used in the pre-form would be a low temperature deformable plastic material. The pre-form would be used in conjunction with required spacers to be applied over the teeth to provide required clearance, cleaning and/or treatment performance. Once the clearance components are applied to the teeth, the pre-form would be heated via microwave or by placing in boiling water so as to be pliable. The pliable pre-form would be applied onto the user's teeth and gingival area to create the customized application tray.

The application tray can be integrated with stressing features to allow elastic conformance to maximize positioning, comfort and performance during application and in use. For example, spring-like elements such as shins, clips and elastic bands may provide fitting over and against gums.

Materials for the MP lumen could range from lower durometer flexible materials (25 shore A) to harder materials more rigid materials (90 shore A), preferably being between 40 and 70 shore A.

Materials could be silicone, thermoplastic elastomer (TPE), polypropylene (PP), polyethylene (PE), polyethylene terephthalate (PET), ethylene vinyl acetate (EVA), polyurethane (PU), or multi-component (combination of materials and hardness) to achieve desired design and performance attributes.

The jet openings or slots could be made through a secondary operation such as drilling or punching, or formed during molding. Alternatively, the jet openings or slots could be inserted into the application tray to provide increased wear and or different jet performance characteristics, and could be combined with frictional cleaning elements or other components to enhance the cleaning and/or treatment affect.

FIGS. 13 to 16 depict an embodiment of an application tray 1200 in which only the user's top or bottom teeth and gingival area are contacted with liquid. It should be understood that in other embodiments, application tray 1200 may be designed to substantially simultaneously contact both the top and bottom teeth and gingival area of the user, as depicted elsewhere herein.

Figure 13:
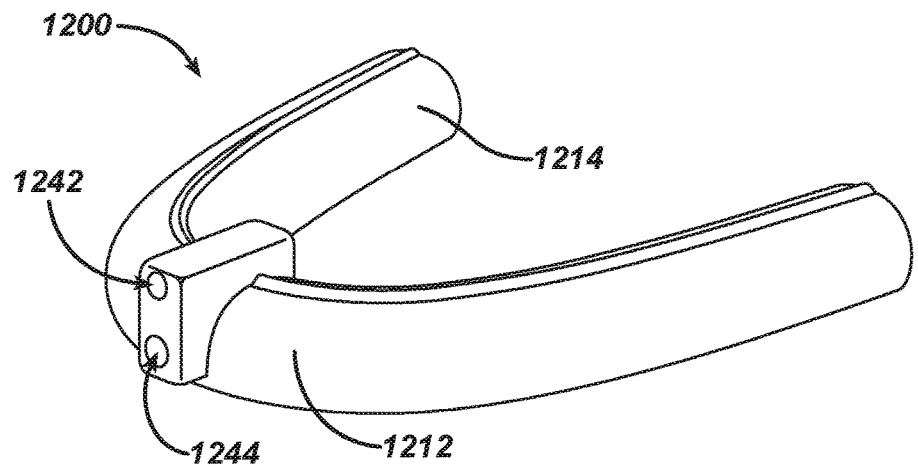
FIG. 13 is a top front perspective view of a third embodiment of an application tray that may be utilized in the present invention.
Figure 14:
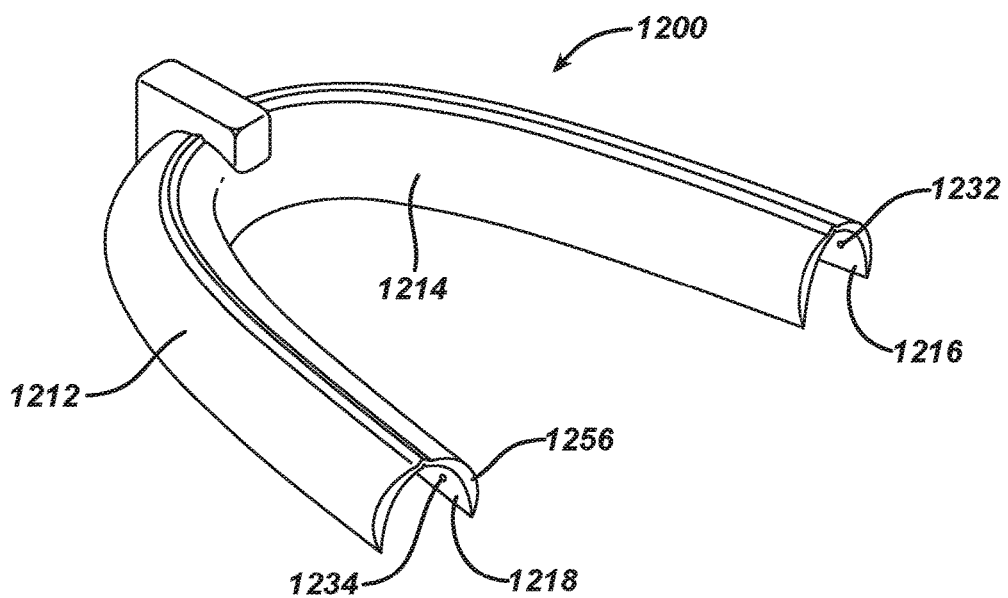
FIG. 14 is a top back view of the embodiment of the application tray of FIG. 13.
Figure 15:
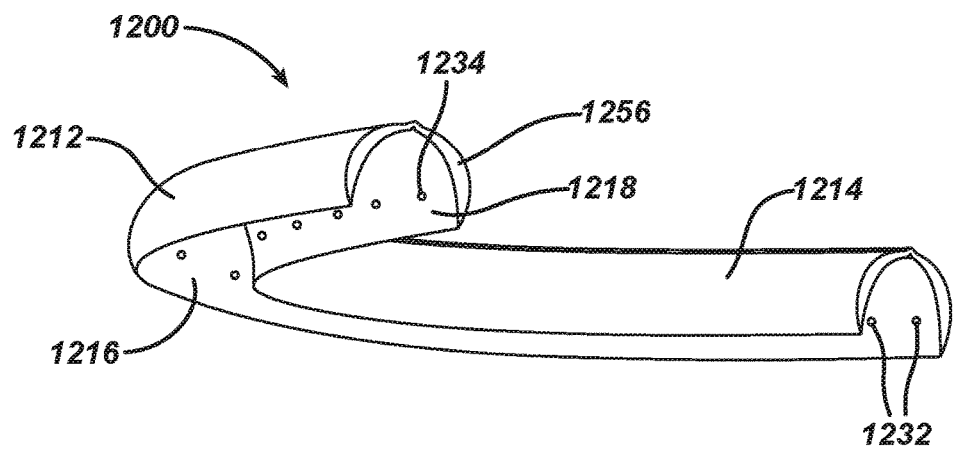
FIG. 15 is a bottom back view of the embodiment of the application tray of FIG. 13.

FIG. 13 is a top front perspective view of a third embodiment of an application tray 1200 according to the present invention. FIG. 14 is a top back view of the embodiment of the application tray 1200 of FIG. 13, while FIG. 15 is a bottom back view of the application tray 1200 of FIG. 13. The figures show application tray 1200 with outer front wall 1212, outer back wall 1214, inner front wall 1216, and inner back wall 1218. Inner front wall jet slots 1232 are located on inner front wall 1216, while inner back wall jet slots 1234 are located on inner back wall 1218. First port 1242 and second port 1244 enter application tray 1200 through outer front wall 1212.

The number and location of inner front wall jet slot 1232 and inner back wall jet slot 1234 as shown in FIGS. 13 to 16 is exemplary and is not intended to limit the scope of the application tray. The actual number, shape and size of inner front wall jet slots 1232 and inner back wall jet slots 1234 affect the cleaning of the teeth and gums, and can be selected or designed to direct jets of cleaning liquid in a variety of spray patterns. The inner front wall jet slots 1232 and inner back wall jet slots 1234 shown in FIGS. 13 to 16 are only one embodiment of jet slot configuration.

Figure 16:
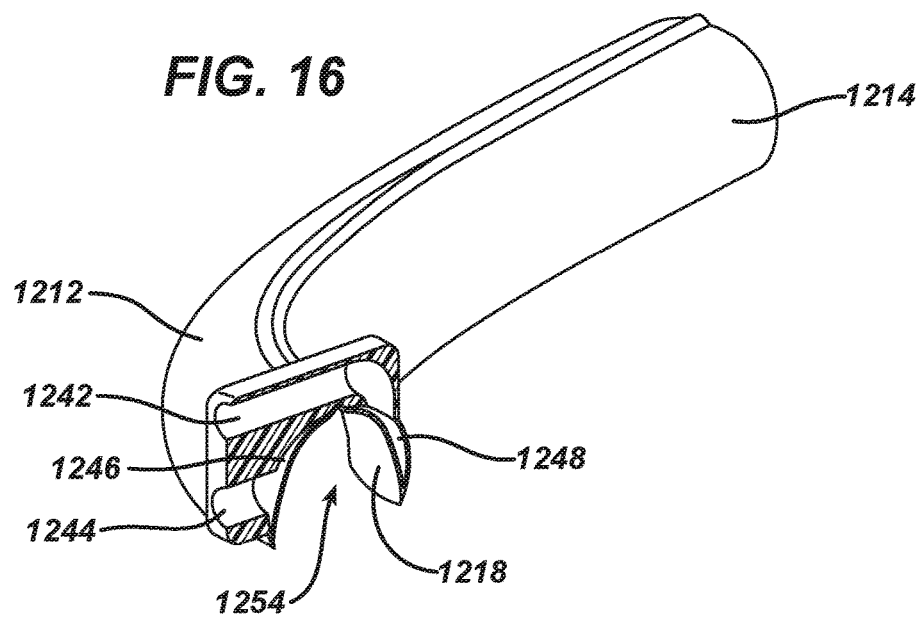
FIG. 16 is a cut-away view of the application tray of FIG. 13.

FIG. 16 is a vertical sectional view of the application tray 1200 of FIG. 13. The figures show first manifold 1246, defined as the space bordered by outer front wall 1212 and inner front wall 1216. Second manifold 1248 is defined as the space bordered by outer back wall 1214 and inner back wall 1218. The liquid contact chamber (LCC) 1254 is defined by inner front wall 1216, inner back wall 1218 and inner base wall 1250.

In one embodiment of a cleaning operation, cleaning liquid enters first manifold 1246 through first port 1244 by pressure and then enters LCC 1254 through inner front wall jet slots 1232. A vacuum is pulled on second port 1242 to pull the cleaning liquid through inner back wall jet slots 1234, into second manifold 1248 and finally into second port 1244. In this embodiment, jets of cleaning liquid are first directed onto the front side of the teeth from one side of the LCC, directed through, between, and around the teeth from the other side of the LCC into the second manifold to provide controlled interdental, gumline, surface and/or gingival area cleaning. Next, the flow in the manifolds is reversed. Cleaning liquid enters second manifold 1248 through second port 1242 by pressure and then enters LCC 1254 through inner back wall jet slots 1234. A vacuum is pulled on first port 1244 to pull the cleaning liquid through inner front wall jet slots 1232, into first manifold 1246 and finally into first port 1244. In the second portion of this embodiment, jets of cleaning liquid are directed onto the back side of the teeth, and directed through, between, and around the teeth and/or gingival area. The alternating of pressure/vacuum through a number of cycles creates a turbulent, repeatable and reversible flow, thereby providing reciprocation of liquid over and about the surfaces of the oral cavity.

In another embodiment of a cleaning, treatment, pre-treat, or post treat operation, it may be preferable to deliver the liquid through one or both manifolds simultaneously, flooding LCC 1254, submerging the teeth for a period of time, and then evacuating the chamber after a set period of time through one or both manifolds. Here, cleaning or treating liquid simultaneously enters first manifold 1246 through first port 1244, and second manifold 1248 through second manifold feeder 1242 by pressure and then enters mouthpiece space 1254 simultaneously through inner front wall jet slots 1232 and inner back wall jet slots 1234. To evacuate the LCC, a vacuum is simultaneously pulled on first manifold 1246 through first port 1244, and second manifold 1248 through second port 1242. Cleaning liquid is pulled through inner front wall jet slots 1232 and inner back wall jet slots 1234, into first manifold 1246 and second manifold 1248. It is also possible to deliver different liquid compositions to first manifold 1246 and second manifold 1248. The different liquid compositions would then combine in the LCC for improved cleaning efficacy. In the dual manifold design it may be preferable to supply each manifold from a separate chamber, such as in a dual action piston pump configuration, where one supply line connects and to supply first manifold 1246 and the other piston supply line provides and removes from second manifold 1248 (when one manifold is being supplied the second manifold is removing and vice versa).

Gingival Seal

The gingival seal forms the bottom portion of the LCCM and contacts with the gingival tissue in such a way as to clean the gingival area, including the sub-gingival pocket. In one embodiment, it provides positioning of the mouthpiece relative to the oral cavity and teeth, and creates a relatively isolated environment with minimal/acceptable leakage during operation, while designed to minimize the gag factor and comfort for the user. In one embodiment, the gingival seal is created by the frictional engagement and compression of an elastomeric material with the gingival. This seal is enhanced during the evacuation of the liquid within and during the cleaning and treatment cycles. The seal also functions as a secondary mechanism for attaching and assembling the manifold and LCCM. The size and shape of the gingival or gum seal preferably utilizes three basic sizes (small, medium and large), but is designed to allow different levels of customization as required by the user for comfort and cleaning/treatment efficacy. These sizes are paired with the three basic sizes of the manifold and LCCM components.

Alternate embodiments for obtaining the gingival seal include the following and may be used in combination with each other or with the embodiment above:

Embodiment #1

The mouthpiece is positioned within the oral cavity and onto the gingival. The seal and position is fixed relative to the teeth and gingival when slight biting pressure is applied against the bite standoffs/locating blocks. The mouthpiece would be made out of a single or combination of materials of different hardness and resilience. In the preferred embodiment, the "H" shaped mouthpiece would have flexible walls (vertical edges of the "H") which would have a soft, resilient gasket-like material (closed cell silicone, gel filled seal, etc.) at the ends of each of the "H" legs. The horizontal pad of the "H" would include biting blocks/standoffs for positioning the mouthpiece in the X, Y, and/or Z locations, relative to the teeth and gingival. Once the mouthpiece is positioned in the oral cavity, closing of the upper and lower jaw to engage the bite blocks would provide positive and rigid positioning of the mouthpiece relative to the oral cavity, while providing interference of the gasket-like material with the gingival material to provide an effective seal and formation of the cleaning, treatment, and/or diagnostic cavity for the duration of the operation.

Embodiment #2

Force applied to the mouthpiece to create inward movement of sidewalls, sealing a soft resilient edge against the gingival tissue. A mouthpiece similar to that described in embodiment #1 would also provide an active locking feature to improve the engagement of the seal. One potential execution of this would require that a hollow section be designed within the horizontal leg and between some or all of the standoffs between the upper and lower sections of the mouthpiece, when the device is not engaged. After the mouthpiece is placed in the oral cavity, the user bites down and compresses the hollow section, which then collapses so that all the bite blocks are in contact. This in turn causes the external walls (the vertical leg portions) to fold inwardly towards the gingival tissue. The resilient gasket attached to these walls engages and compresses against the gingival to create the seal and the cleaning, diagnostic, and/or treatment chamber surrounding the upper and lower teeth.

Embodiment #3

A pneumatic bladder is inflated or pressurized when the mouthpiece is positioned in the oral cavity to create the seal and cavity with the gingival. A mouthpiece similar to that described in embodiment #1 could also provide an active seal through the inflation of a bladder, or bladders, within the mouthpiece. The air could also subsequently be utilized to clean and or dry the teeth/cavity and/or provide treatment (gas and or entrained particle in gas) for treatment, cleaning and/or diagnostics.

Embodiment #4

A hydraulic bladder is inflated or pressurized when the mouthpiece is positioned in the oral cavity to create the seal and cavity with the gingival. A mouthpiece similar to that described in embodiment #1 could also provide an active seal through the pressurization of a bladder(s) within the mouthpiece. The liquid composition could also subsequently be utilized to clean and/or treat the teeth and or gingival tissue with or without gas or entrained particles for cleaning, treatment, or diagnostics.

Embodiment #5

After the mouthpiece is positioned in the oral cavity, the seal is created through a change in compliance of the material engaging the gingival with or without expansion of the material to seal around the gingival due to liquid absorption (utilize a hydrogel, etc.).

Embodiment #6

After the mouthpiece is positioned in the oral cavity, Nitanol wire or other shape-memory materials embedded into the mouthpiece cause the side walls to engage the gingival due to the change of body temperature in the oral cavity, creating a positive seal with the gingival tissue.

Embodiment #10

A foam-like material is extruded into the mouthpiece area initially or alternatively during each use to create the mouthpiece seal and subsequent cleaning, treatment, and diagnostic cavity.

Embodiment #11

A disposable or dissolvable insert is provided to provide the seal to the gingival tissue for multiple or each use of the mouthpiece.

Embodiment #12

An adhesive is contained on the gum seal contact surface, which can be saliva or water activated. Adhesive would provide potential seal improvement and could be single use or multiple use application, depending on the formulation. Sealing system can be used with any combination of other sealing systems discussed.

Embodiment #13

The gingival seal is created through a combination of material on contact area and geometry at the interface that creates a suction-like effect in the seal contact area (suction cup) through creation of a vacuum in this area during the engagement.

Embodiment #14

The gingival seal area can be made and customized to a user's mouth by utilizing a deformable material that can be placed and positioned against the gingival, which then takes on a permanent set for the user. This may be created through boiling and placing in the mouth and pressing against the gingival by closing the jaw and or like method, then removing from the oral cavity (similar to a mouth guard). As the sealing material cools, it takes on a permanent set.

Embodiment #15

The gingival seal area can be created by taking a generic or semi generic bladder and placing into the oral cavity in close proximity to the desired gingival seal contact area. This bladder can then be filled and directionally supported to engage and conform against the gingival. The filling material would be a fast curing material, which would take set to provide the customized sealing form, which would then be reusable by this specific user. The bladder could be a TPE and/or thin silicone based material, and the filling material could be an RTV, epoxy, polyurethane or similar material to provide a rigid, semi rigid or flexible permanent set form when cured or set.

In a preferred embodiment, the gingival effective seal is a contact seal created by the geometry of the LCCM bottom edge engaging the gingiva. The LCCM bottom edge is preferably flexible to allow conformance to different user's gingival surfaces below the gum line and along the points of contact. This portion also needs to be soft enough so as not to cause abrasion or damage to the gingival region to provide comfort to the user, while maintaining an effective seal. In the preferred geometry, the LCCM contact area provides a radial and or curved smooth surface to provide point of contact and a comfortable sealing. The preferred material of this edge would be a low durometer silicone, under 100 Ra, and more preferably between 15 Ra and 70 Ra, due to its durability and inherent performance characteristics, but could also be soft and/or flexible materials, such as TPE's and other materials know in the art.

The effective seal is formed in conjunction with the operation of the vacuum and removal of fluid from the LCC, allowing any residual leakage from the universal appliance to be pulled back into the LCC and the hand held device for subsequent removal.

Components

The entire system will be modular in nature so individual components can be easily replaced by the user. Reasons for replacement include but are not limited to wear, malfunction, and biohazard. Some components may also be disposable and replaceable by nature (refill cartridges, etc), thus modular and easily replaced by the user.

Pump System

In one embodiment, the liquid may be delivered from a reservoir in the mouthpiece handle or base station via powered pump. The pump may be capable of responding to input from a logic system (artificial intelligence, or AI) to vary pressure, cycle time (for each stage and total process), reciprocating motion requirement and/or timing, direction of flow, liquid velocity/pressure, purge specifications, and similar. Though shown in FIG. 3 as a piston pump 420, the pump may be a piston pump, valveless rotary piston pump, diaphragm pump, peristaltic pump, gear pump, rotary pump, double-acting piston pump, vane pump, or similar. A charged pneumatic cylinder or air compressor may also drive the system as an alternative embodiment. The cycle time for the total process, cycle time for each individual stage, and flow velocity for each stage of the cycle may be variable and potentially customized to each individual user/day of the week/oral health conditions. It is also possible to change the volume of liquid delivered per stroke or over a time period in different offerings of the system, depending on the needs of the specific user and specific treatment requirements. The pump system may be in the hand piece or in the base station. The volume of liquid per stroke of the piston pump may be relative large to give the effect of pulses of liquid in the mouthpiece. An alternatively embodiment has a pump that delivers constant flow with low or no pulsations. In the preferred embodiment, the forward stroke will deliver liquid to the mouthpiece through specified nozzles and the back stroke will create a vacuum to suck liquid through specific nozzles in the mouthpiece back to the pump. The direction of the liquid to and from the mouthpiece can be reversed by changing the direction of the motor in a rotary valveless pump, directional valve, or other means. The liquid drive system will not start until the mouthpiece is properly inserted and sealed against the gums. The system will automatically stop dispensing and may remove residual liquid from the mouth once the mouthpiece is removed (effective seal against gums is broken) from the mouth. This will allow the user to safely increase the concentrations of active ingredients in the cleaning/treatment formulation. The system will not start until the mouthpiece has an effective seals against the gums. In one embodiment the pump system is entirely contained in the hand piece, and in another the pump system is housed in the base station.

In a preferred embodiment, the design will have a dual piston arrangement to provide separate vacuum and delivery pumps, to allow simultaneous vacuum and delivery of fluid from/to the LCC. The first piston would be for delivery/pressure, and can be configured for dual action, delivering fluid both on the up and down strokes, but more preferably single action, delivering fluid on the upstroke only. The second piston would be the vacuum piston, which could be configured for dual or single action, but more preferably dual action to maintain a negative pressure in the LCC, and minimize residual leakage into the oral cavity from the LCC. The vacuum piston and total vacuum/volumetric removal of fluid and air from the LCC is preferably greater than the volumetric delivery of fluid to the LCC to ensure and effective seal of the LCC, minimizing residual fluid into the oral cavity. The ratio of the volumetric removal to delivery of fluid/air from the LCC is about 10:1 or less, or about 3:1. The delivery and vacuum pistons can be oriented in a linear arrangement to minimize the cross-sectional area of the handle, or in a side-by-side arrangement to reduce overall length of the handle. They could be driven off the same piston rod to minimize device complexity/cost and be driven off the same drive motor.

It is preferred to utilize a unitary piston design without o-rings (with flared cupped edges), as this design reduces friction of the piston to cylinder by pulling back away from the cylinder in the non-performing direction (down stroke for delivery), while expanding against the cylinder to provide improved efficiency when moving in the performing direction (upstroke for delivery). The design also provides better compensation for wear of the pistons and cylinders due to its flexible nature.

Valving/Liquid Control & Liquid Input/Output

It may be desirable to change the direction of the flow to the mouthpiece if the mouthpiece embodiment is used wherein the mouthpiece has one inlet and one outlet. The direction of liquid flow through the teeth would be reversed by changing the direction of flow of the inlet and outlet to the mouthpiece, therefore increasing the efficacy and sensory affects of the cleaning process. The mouthpiece may have nozzles on opposite sides of the teeth wherein one side of the jets are pressured and the opposite side draws a negative pressure differential. This forces the liquid "through/between" the teeth. The flow is then reversed on each set of nozzles to move the liquid the opposite direction through the teeth. The liquid may then be reciprocated back and forth. The direction of flow may be reversed and/or reciprocated by reversing the direction of a specialized pump, such as a rotary valveless pump. Another embodiment includes but is not limited to reversible check valves, wherein the orientation of the check valves to the pump is reversed, thereby reversing the direction of the flow throughout the system. Another embodiment includes two controlling 3-way valves with the logic (AI) system to reverse the direction of flow when activated. A further embodiment has a logic (AI) system to one controlling 4-way valve with one input from the pump, a return to the pump, and two outlets to the mouthpiece that can reverse flow direction as desired. Another embodiment involves configuring tubing so as to shut off of the flow with pinch valves to specific tubes in order to reverse the flow of the system. Another embodiment includes development of a liquid control switching box that connects two tubes on one side of the box to two tubes on the opposite side of the box. In one orientation the liquid flow moves directly across the box from one collinear tube to the next, while in the other position the liquid flow moves in an "X" direction whereby liquid flow direction is "crossed" in the switching box. In another embodiment, flow is reciprocated by using a double-acting piston pump, wherein the flow is constantly reciprocated back & forth between the two piston pump heads.

In one embodiment the liquid control system is entirely contained in the hand piece, and in another embodiment, the liquid control system is housed in the base station. The tubing used in the system must withstand both pressure and vacuum states.

One or more liquid types from individual reservoirs can be delivered through the mouthpiece individually or combined. Any combination and concentration variation can be used. The reservoirs may reside in the hand piece or in the base station.

The system may include manual and/or automatic air purging, and/or an accumulator to provide system compressibility.

The valving system for directing and controlling fluid to and from the vacuum and delivery pumping systems may be optimized to provide a modular, cost effective, efficient system that allows for simplified manufacturing and assembly. In addition, improved maintenance of the system can be achieved by using a cut sheet of flexible film sandwiched between two injection moldable components.

The switching/fluid reciprocation control system to create the fluid reciprocation can be mechanical (driven via mechanism/gearing or electrical (electrically controlled valving such as multi-way solenoid flow valves, initiated via an electrical signal). In the preferred mechanical embodiment, the switching system is driven off the pump drive motor(s), so as to minimize the size, complexity and cost of the overall system. This is completed via mechanical linkages and gearing as shown below, driving the unique switching mechanism. The switching mechanism can be reciprocative in nature, such as a cam engaging a slide switching member, pushing it back and forth. It can also be a unique, continuous revolving switching disk member as shown in the exploded and cross-sectional views below, switching fluid direction 2 times for every single rotation of the disk, due to the unique D-shaped flow channel. The design provides a built in pressure relief valve like function that allows flow crossover when switching flow directions, without any additional hardware, to minimize strain on the drive motor/system and increasing life of the motor/system.

Interface (Electrical & Liquid)

The hand piece may have an electrical and/or communication system that interfaces with the base station. This includes but is not limited to charging of the rechargeable battery, transferring diagnostic information between the units, transferring custom profile information between the units, and transferring program-related information between the units. Information can be transferred wirelessly (RFID, 802.11, infrared, etc.) or through a hard connection. The electrical system will include logic so as to control the function, start, and stop of the system based on preset criteria. The criteria may include starting only after a seal has been created between the mouthpiece and the gums, ensuring a properly charged liquid system, ensuring a minimum battery charge level, ensuring the liquid level is within a specified range, etc. There may be a logic system that may communicate with various components of the device including, but not limited to, initiating algorithms to control the sequencing of the valves, motion of the piston and therefore motion of the liquid, receive inputs from the consumer, receive inputs from the temperature sensor, receive diagnostic input, detect engagement of the mouthpiece seal against the gums, etc. The logic system must be capable of processing and responding to an input and outputting appropriate data. The system may include redundant circuitry wherein providing a fail-safe design.

The system may include a means to provide feedback to the user such as lights, display, touch screen, recorded messages, vibration, sounds, smell, and similar. It may also have a means to operate the system and select processes/settings, such as switches, touch screens, buttons, voice commands, and similar.

The system may include a means for tracking statistics such as time between uses, length of use/cycle, total uses, regimen details (amount and time of each liquid/treatment), time to replace specific system components, and similar. The system may provide feedback to the user to indicate time to replace or refill, wear, disposable, or replaceable components.

There will be a method of liquid supply, which may be a liquid reservoir, hose supply system, or similar. The liquid supply may be located in the base station and transferred to a reservoir in the hand piece when the hand piece is docked in the base station. The liquid may then be delivered through the mouthpiece during the cleaning process, and purged out of the system delivery and/or after the cleaning process. In another embodiment, the hand piece is connected to the base station with a liquid connection means, and liquid is delivered from a reservoir in the base station, through the hand piece, directly to the mouthpiece.

There may be consumable cartridges that may contain treatment solutions, cleaning solutions, diagnostic solutions, or similar. The cartridges may be modular in design so as to be easily replaceable by the user.

The system may include a means of detecting the level of plaque on the teeth. One such method of detection is by coating the teeth with a fluorescein solution, which has been proven to stick to plaque, and monitoring the light waves emitted from the fluorescein-coated plaque vs. uncoated teeth regions. The light wave is different for each region, therefore it is discernable which areas and how much plaque exists on the teeth. Other similar methods of plaque detection may also be used, such as vision systems.

Cleaning/Purging/Charging

The liquid system may be charged with disposable cartridges, refilling of a chamber, accessing a main reservoir in the base station with tubing, or other means of liquid transfer (gravimetric, hand pump, siphon pump, use of main pump drive or secondary system to fill/charge reservoirs, and similar). The liquid reservoirs may be filled with a combination of different liquids to create a unique combination of different liquid concentrations. In another embodiment, ingredients may initially be in a form other than liquid (gel, powder, tablet, and similar) and may be combined with liquid for added treatment and/or cleaning benefits.

The hand piece will have a purge setting that is simply and easily activated by the user during and/or after the cleaning process. This can be accomplished with a method such as a single button pushed by the user that will purge the hand piece of liquid and waste. In another embodiment, the excess liquid and waste is transferred from the hand piece to a waste reservoir or the sink drain, outside of or docked in the base station. There may be a filtration system to protect the components from contaminants. In a further embodiment, the hand piece houses a disposable waste cartridge. In an alternate embodiment, the mouthpiece is cleaned in the base station between uses. The cleaning method includes, but is not limited to, UV cleaning, alcohol bath, alternate cleaning liquid bath, or other similar method. The liquid cleaning bath may or may not circulate in and/or around the mouthpiece.

Drive System

The liquid system may be driven by a rotary motor with means to translate motion from rotation to linear movement. This may be achieved via eccentric cam, linear sliders, or other known methods. In an alternate embodiment, a linear motor, or series of linear motors, may drive the system. This would possibly reduce the size of the liquid system and gain additional control of liquid delivery through liquid vacuum. The motor(s) may directly drive the pistons up and down in a translational fashion.

In order to optimize the design and minimize the size of the device, the components of the linear drive may be integrated into the pump system. The piston itself may incorporate the magnet and the coil may be imbedded in or around the outer piston chamber walls. Alternatively the piston and/or fixed attachment means to piston can be moving portion and the magnet can be stationary (i.e. surrounding or within the piston walls). In addition, both the vacuum and delivery pistons may have imbedded magnets that act against one another to create or assist with the piston movement.

The motor will also drive the movement of the reciprocating flow controller. A rotary motor may have a worm, bevel, or similar gear assembly to translate the motor rotation to spin the reciprocating flow controller. The outer circumference of the reciprocating flow controller may be comprised of gear teeth, which may be used as a means to rotate the reciprocating flow controller disk from the translated motor rotation. Alternatively, a linear motor may drive the FDM in a ratcheting fashion or geared fashion, such as motion transference like the geneva mechanism.

In some embodiments, the pumping and vacuum sections may be oriented in-line with one another. Alternatively, they may be oriented parallel to each other. Each orientation has different advantages in regard to compactness. The pumping and vacuum sections can be connected together, or alternatively operate independently, being synchronized in frequency and/or some factor of frequency (i.e. vacuum section could have the volumetric displacement of the delivery section, but move at a different speed) or could run asynchronously. If the delivery and vacuum sections are oriented in-line with one another, they may be connected to each other via a rod. This may allow the delivery and vacuum pistons to be driven simultaneously, ensuring synchronization between the pumping and vacuum strokes.

The delivery piston may be driven by the same rod that drives the vacuum piston, but may have also some damping means and or delay one to the other, such as slot where it attaches to the piston. This may allow for extra play in the drive piston, causing the vacuum stroke to start slightly before the delivery stroke and continue slightly after the delivery stroke. This may give the vacuum stroke additional opportunity to remove liquid from the appliance since it is still creating a vacuum while the delivery piston is dwelling, as well as minimizing leakage due to gravity and appliance position into the oral cavity.

The vacuum piston and delivery piston may have means to dump liquid into reservoir as a safety, in case either experiences any sort of partial or full blockage, which could result in premature failure of device components (motors, valves, seals, etc). This allows for safe and controlled operation and prevents over pressurization when the main flow ports are have been compromised and repeatable device performance for efficacy. By dumping into the local reservoir instead of to atmosphere, leakage potential outside of the device is minimized.

Temperature Control

In one embodiment, the liquid temperature may be controlled within a specified range. If the liquid is too cold, it may cause discomfort and sensitivity in the user's mouth. If the liquid temperature is too high, it may cause discomfort, sensitivity, and damage to the user's mouth. The system may be confirmed not to run if the liquid temperature above the specified limit. A heating element may increase the temperature if it is below the minimum specified limit. The system may be confirmed not to run unless the liquid temperature is within the specified range. The temperature feedback may be provided, but is not limited to thermistors, thermocouples, IR or other temperature monitoring means. This information may be fed back to the logic (AI) system.

The drive system may have means to heat the liquid to a specific temperature range. Liquid may be heated in one or more locations of the system. Methods of heating the liquid include, but are not limited to, an inductive element, a radiant element, a ceramic element, a tubular sealed heating element (e.g. a fine coil of Nickel chrome wire in an insulating binder (MgO, alumina powder), sealed inside a tube made of stainless steel or brass), a silicone heater, a mica heater, or an infrared heater.

Figure 17A:
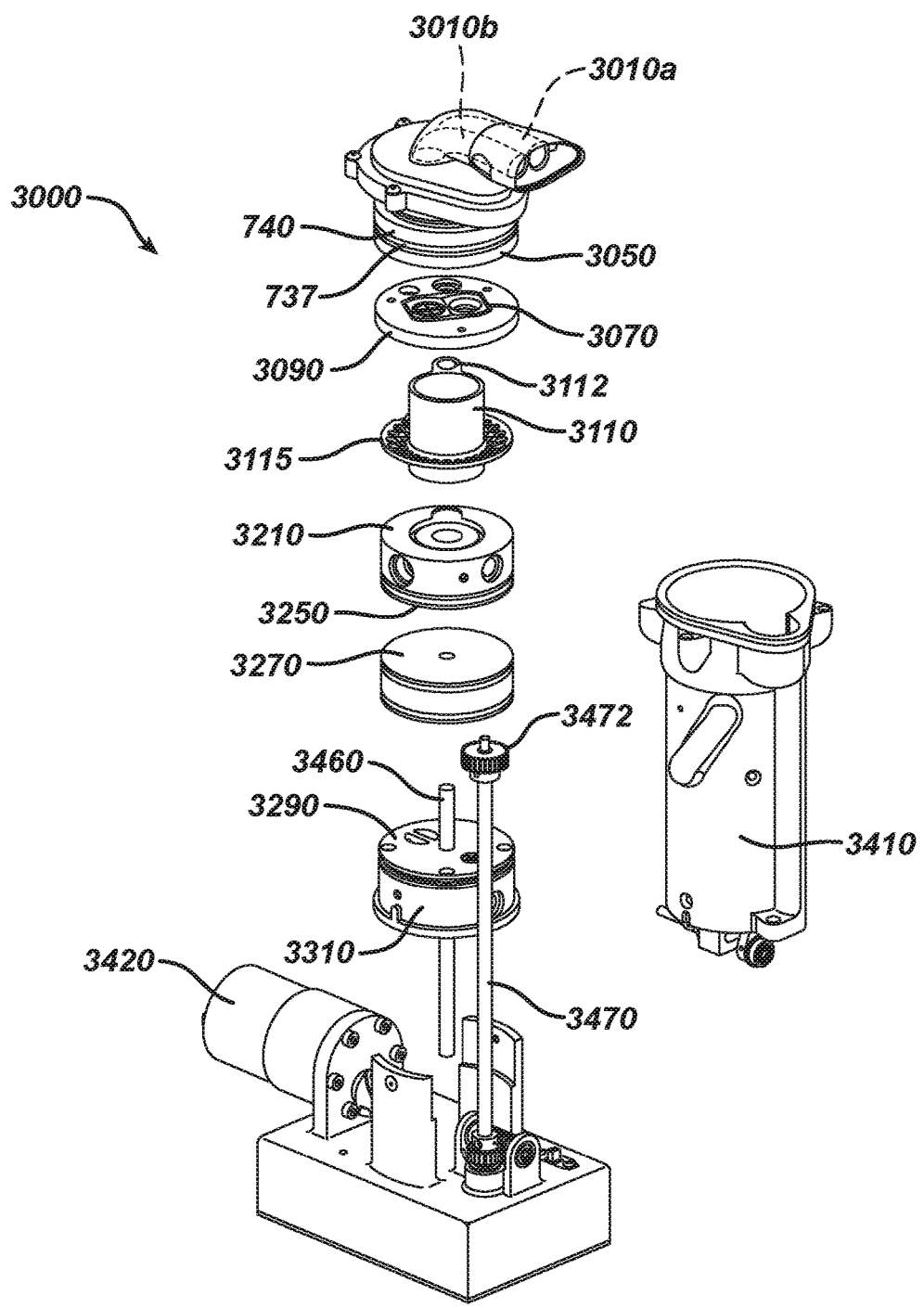
FIG. 17a is an exploded view of an embodiment of a hand piece that may be utilized in the present invention.

An embodiment of a hand piece according to the present invention is shown in FIGS. 17a to 17e. FIG. 17a is an exploded view of a hand piece 3000 that pumps liquid to, and pulls liquid from, the application tray, thus providing reciprocation of the liquid to and from the application tray. In this embodiment, hand piece 3000 is designed in a modular fashion, with a pumping section, a vacuum section, a reciprocating section, and pumping and driving sections. Modular construction allows for easier design for manufacturing (DFM), with easy assembly and repair. The embodiment is also designed to minimize the size of the device as well as the amount of liquid used in operation.

Hand piece 3000 includes outlet pipes 3010a and 3010b, reciprocating flow controller 710, inlet disk top section 3050, inlet disk bottom section 3090, delivery cylinder sleeve 3110 with bubble-break plate 3115 and delivery cylinder filling tube 3112, separator plates 3210, 3310, vacuum end disks 3250, 3290, vacuum piston 3270, vacuum cylinder sleeve 3410, piston rod 3460, indexing shaft 3470, and diverter drive gear 3472.

Figure 17B:
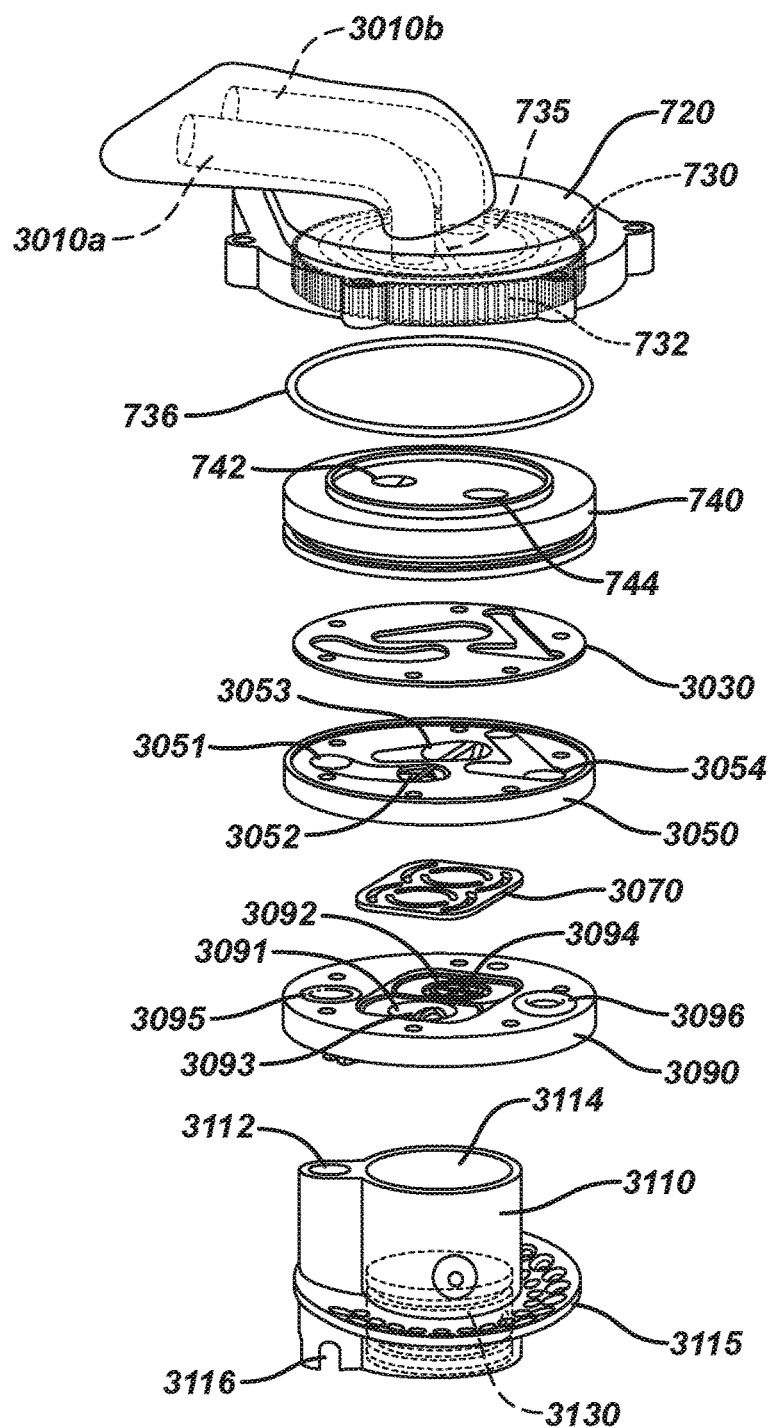

An exploded view of pumping section of hand piece 3000 is shown on FIG. 17b. The figure shows outlet pipes 3010 attached to cap 720 of reciprocating flow controller 710. Flow diverter disk 730, with position adjuster 732 in the form of a gear, is disposed in cap 720 and sits on base 740. O-ring 736 is between flow diverter disk 730 and base 740. Base ports 742 and 744 pass through base 740. Panel 735 for diverting liquid flow is disposed in flow diverter disk 730. Inlet disk top section 3050 has inlet disk top section ports 3051, 3052, 3053, and 3054, and is separated from base 740 by sealing gasket 3030. Inlet disk bottom section 3090 has inlet disk bottom section ports 3091, 3092, 3095, 3096. Duel flap valve 3070 is between inlet disk top section 3050 and inlet disk bottom section 3090, with the two flaps of duel flap valve 3070 above inlet disk bottom section ports 3091 and 3092 and below inlet disk top section ports 3052 and 3053. Inlet disk bottom section port 3091 includes a one-way valve 3093, allowing liquid to flow from inlet disk top section port 3052 to inlet disk bottom section port 3091 through duel flap valve 3070. Inlet disk bottom section port 3092 includes a one-way valve 3094, allowing liquid to flow from inlet disk bottom section port 3092 to inlet disk top section port 3053 through duel flap valve 3070. Inlet disk bottom section 3090 is disposed on top of delivery cylinder sleeve 3110. Delivery is disposed along delivery cylinder sleeve 3110, while delivery piston 3130 is disposed in the volume defined by delivery cylinder sleeve 3110. Bubble-break plate 3115 is disposed about cylinder sleeve 3110. Delivery volume 3114 is the volume defined by delivery cylinder sleeve 3110 minus the volume of delivery piston 3130.

Figure 17C:
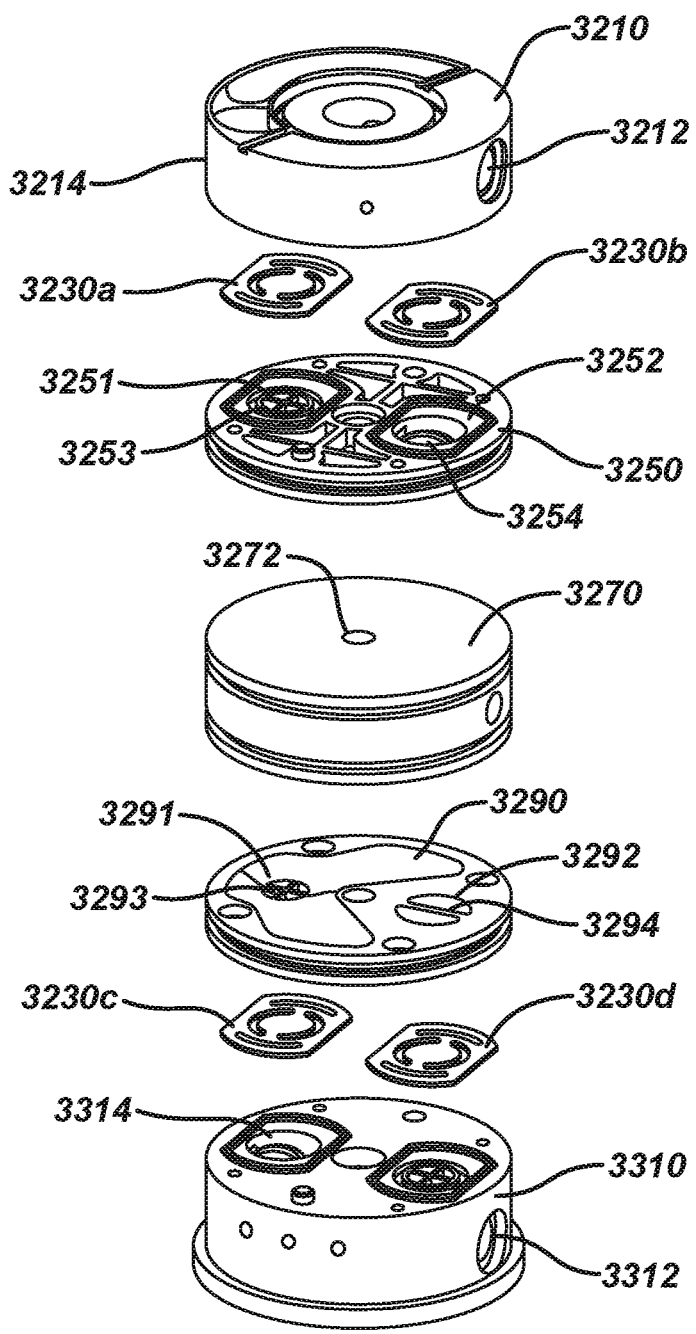

FIG. 17c is an exploded view of vacuum section of hand piece 3000. The figure shows separator plate 3210, with separator plate ports 3212 and 3214, disposed on top of vacuum end disk 3250. Vacuum end disk 3250 has vacuum end disk ports 3251 and 3252. Flap valves 3230a and 3230b are between separator plate 3210 and vacuum end disks 3250. Flap valves 3230a and 3230b are above vacuum end disk ports 3251 and 3252 and below separator plate ports 3212 and 3214. Vacuum end disk port 3251 includes a one-way valve 3253, allowing liquid to flow from vacuum end disk port 3251 to separator plate port 3214 through flap valve 3230a. Vacuum end disk port 3252 includes a one-way valve 3254, allowing liquid to flow from separator plate port 3212 to vacuum end disk port 3251 through from flap valve 3230b. Vacuum piston 3270, disposed under vacuum end disks 3250, has piston rod hole 3272 through which piston 3460 passes. Beneath vacuum piston 3270 is vacuum end disk 3290, disposed on top of separator plate 3310. Vacuum end disk 3290 has vacuum end disk ports 3291 and 3292. Separator plate 3310 has separator plate ports 3312 and 3314. Flap valves 3230c and 3230d are between vacuum end disk 3290 and separator plate 3310, above vacuum end disk ports 3291 and 3292 and below separator plate ports 3312 and 3314. Vacuum end disk port 3291 includes a one-way valve 3293, allowing liquid to flow from vacuum end disk ports 3291 towards separator plate port 3314 through flap valve 3230c. Vacuum end disk port 3292 includes a one-way valve 3294, allowing liquid to flow from separator plate port 3312 to vacuum end disk port 3292 through flap valve 3230d.

Figure 17D:
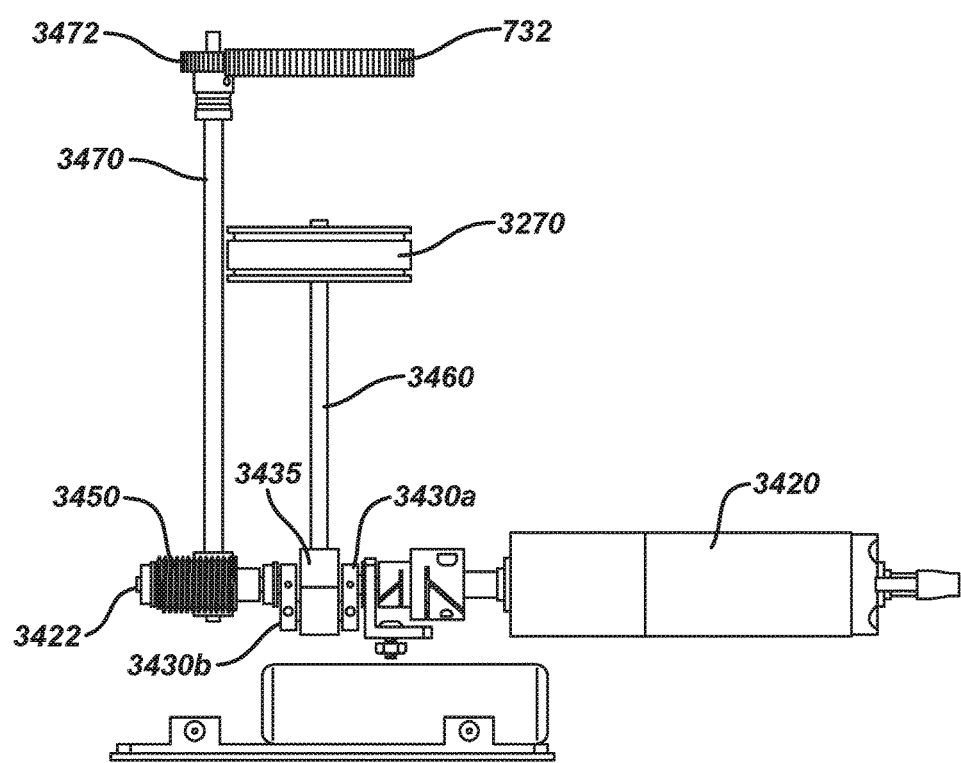

FIG. 17d is a side view of drive system of the pumping and driving sections of hand piece 3000. Motor 3420 drives shaft 3422, which is linked to crankshaft arms 3430a and 3430b, and worm gear 3450. Crankshaft arms 3430a and 3430b are linked to crankshaft link arm 3435, which is linked to piston rod 3460. Piston rod 3460 is attached to vacuum piston 3270 and, though not shown, delivery piston 3130. Indexing shaft 3470 is in contact with worm gear 3450, which is linked to diverter drive gear 3472. When shaft 3412 spins, crankshaft arms 3430a, 3430b and crankshaft link arm 3435 convert the rotary motion of shaft 3422 to a linear, reciprocating motion on piston rod 3460, such that vacuum piston 3270 and delivery piston 3130 move up and down. Simultaneously, worm gear 3450 converts the rotary motion of shaft 3422 to a rotary motion of indexing shaft 3470. Indexing shaft 3470 rotates diverter drive gear 3472, which is linked to position adjuster 732 in reciprocating flow controller 710.

FIG. 17e is a cut-away view of hand piece 3000, showing the spatial relationships between the components in the pumping section, vacuum section, and pumping and driving sections. Cylinder volume 3412 is the volume of vacuum cylinder sleeve 3410 not occupied by the components of the pumping section, vacuum section, and pumping and driving sections, and serves as the liquid reservoir in the embodiment shown.

The general operation of hand piece 3000, is as follows:
1. Hand piece 3000 is sufficiently filled with cleaning liquid. The liquid initially resides in cylinder volume 3412 of vacuum cylinder sleeve 3410.
2. The user inserts any embodiment of an application tray, for example application tray 100 or 1100, into their mouth. The hand piece 3000 may be activated by a sensor (pressure sensor, proximity sensor, etc.) or the device may be activated by the user. The cleaning cycle is initiated.
3. On the "down stroke" of piston rod 3260, delivery piston 3130 pulls liquid from the bottom of cylinder volume 3412. The liquid flows through delivery cylinder filling tube 3112, inlet disk bottom section port 3095, inlet disk top section port 3051, inlet disk top section port 3052, duel flap valve 3070, and one-way valve 3093 in inlet disk bottom section port 3091, and into delivery volume 3114. It is preferred that the entry port 3116 on delivery cylinder filling tube 3112 is located at the bottom of the tube to minimize the total liquid required for cleaning/treatment and to avoid pulling air into delivery volume 3114.
4. On the "upstroke" of piston rod 3260, delivery piston 3130 forces the liquid though inlet disk bottom section port 3092 with one-way valve 3094. The liquid flows through duel flap valve 3070, through inlet disk top section port 3053, and finally through base port 742 of reciprocating flow controller 710.
5. Liquid flow through reciprocating flow controller 710 is described earlier using FIG. 4c and FIG. 4d. In brief, when reciprocating flow controller 710 in its first position (FIG. 9c), incoming liquid from inlet disk top section port 3053 enters reciprocating flow controller 710 through base port 742. The liquid exits reciprocating flow controller 710 through cap port 722, flowing into outlet pipe 3010b. Returning liquid, flowing in through outlet pipe 3010a, reenters reciprocating flow controller 710 through cap port 724. The liquid exits reciprocating flow controller 710 through base port 744. When reciprocating flow controller 710 in its second position (FIG. 4d), incoming liquid from inlet disk top section port 3053 enters reciprocating flow controller 710 through base port 742. The liquid exits reciprocating flow controller 710 through cap port 724, flowing into outlet pipe 3010a. Returning liquid, flowing in through outlet pipe 3010b, reenters reciprocating flow controller 710 through cap port 722. The liquid re-exits reciprocating flow controller 710 through base port 744. Reciprocation of cleaning liquid in application tray 100 of FIG. 1 is achieved by switching reciprocating flow controller 710 between its first and second positions. As shown in FIG. 17d, the switching of reciprocating flow controller 710 between its first and second positions is achieved by worm gear 3450, which converts the rotary motion of shaft 3422 to a rotary motion of indexing shaft 3470. Indexing shaft 3470 rotates diverter drive gear 3472, which is linked to position adjuster 732 in reciprocating flow controller 710. Though shown as continually rotating in this embodiment, it is to be understood that reciprocating flow controller 710 may be driven via separate means, such as another motor. Also, the time interval for switching reciprocating flow controller 710 between its first and second positions may, in some embodiments be between about 1 and about 100 seconds, or between about 2 and about 10 seconds, and may be varied over the course of the cleaning/treatment.

6. In the present embodiment, the vacuum section of hand piece 3000 is effective during both the "upstroke" and "down stroke" of piston rod 3260. Vacuum piston 3270 is dual acting, and draws liquid from application tray 100 on both the upstroke and down stroke of vacuum piston 3270. The liquid flowing through base port 744 of reciprocating flow controller 710 flows through inlet disk top section port 3054 and continues through inlet disk bottom section port 3096, arriving in vacuum return tube 3412. The liquid in cylinder volume 3412 is then drawn to vacuum volumes 3275a or 3275b. Vacuum volume 3275a is the volume between vacuum end disk 3250 and vacuum piston 3270. Vacuum volume 3275b is the volume between vacuum end disk 3290 and vacuum piston 3270. During the "upstroke" of piston rod 3260, the liquid in cylinder volume 3412 is drawn through separator plate port 3312, and flows through flap valve 3230d, one-way valve 3294, and vacuum end disk port 3292, arriving in vacuum volume 3275b. During the "down stroke" of piston rod 3260, the liquid in cylinder volume 3412 is drawn through separator plate port 3212, and flows through flap valve 3230b, one-way valve 3254, and vacuum end disk port 3222, arriving in vacuum volume 3275a. As noted, the vacuum piston 3270 in this embodiment is dual acting, drawing liquid from application tray 100 on both the upstroke and down stroke of vacuum piston 3270. So, while vacuum volume 3275b is drawing in liquid from cylinder volume 3412, the liquid in vacuum volume 3275a is being pumped into cylinder volume 3412. In contrast, while vacuum volume 3275a is drawing in liquid from cylinder volume 3412, the liquid in vacuum volume 3275b is being pumped into cylinder volume 3412. During the "upstroke" of piston rod 3260, the liquid in vacuum volume 3275a is pumped through vacuum end disk port 3251, and flows through one-way valve 3253, flap valve 3230a, and separator plate port 3214, arriving in cylinder volume 3412. During the "down stroke" of piston rod 3260, the liquid in vacuum volume 3275b is pumped through vacuum end disk port 3291, and flows through one-way valve 3293, flap valve 3230c, and separator plate port 3314, arriving in cylinder volume 3412.

7. The cycle continues with cycles comprising both "upstrokes" and "down strokes" of piston rod 3260, with liquid motion through hand piece 3000 as described in steps 3 through 6 above.

The ratio of the total volume of vacuum volumes 3275a and 3275b to delivery volume 3114 may be any range, such as 1:1, optionally about 3:1 or greater, or about 4:1 or greater. Since delivery piston 3130 only delivers liquid on one "half" of the pumping/vacuuming cycle, while vacuum piston 3270 works on both halves of the cycle, the ratio of the volume of liquid delivered to application tray 100 to the volume of liquid drawn from application tray 100 is 8:1 per cycle. The dual acting vacuum piston 3270 also provides vacuum during the half of the stroke where delivery piston 3130 is not delivering liquid, increasing the opportunity to retrieve liquid from application tray 100, as well as clear additional liquid which leaked from application tray 100 into the oral cavity. Testing has shown a minimum 3:1 volumetric ratio of liquid vacuum to liquid delivery per stroke provided the necessary vacuum to minimize leakage into the oral cavity from application tray 100 when the tray has a marginal gingival seal, which may occur in embodiments of a universal (designed to fit a range of people) application tray 100 design.

In some embodiments vacuum piston 3270 is single acting. However, a dual acting vacuum piston 3270 may show some advantages.

In some embodiments, cylinder volume 3412 may have an air separator to reduce the foaming. Also, a breather vent may be required so that the pumping/vacuum system does not over pressurize and lock/fail. The breather vent may be on the opposite side of the cylinder volume 3412 from the outlets of separator plate ports 3214 and 3314 to avoid liquid splashing out of the breather vent. In addition there may be a wall to split the cylinder volume 3412 into two halves, to further reduce the chance of liquid splashing out of the breather vent.

In general, cylinder volume 3412 is vented since more liquid is being delivered to cylinder volume 3412 from the vacuum system than is being drawn from the delivery system. The excess (air) is exhausted from a vent in cylinder volume 3412. The vent could use a valve, such as an umbrella valve, so air can escape but cannot enter the reservoir from the same opening, or a 2-way valve or vent hole. To further reduce loss of liquid through the vent, a wall may be used to divide cylinder volume 3412 in two parts. One side contains the supply line, and the other side contains the vent. To optimize the separation of air from liquid in cylinder volume 3412, an air separator may be placed in the reservoir, below the supply line. As the liquid drops from supply line into cylinder volume 3412, it passes through an air separator, which may be a solid plate with holes. This allows the liquid to pass, while removing entrained air and helping to separate the two liquid states (liquid vs. gas). The air separator may have various designs, such as an angled solid shelf with holes, a spiraling ramp, a spiraling ramp with holes, two or more levels of angled shelves with holes, multiple spiraling ramps, similar to a multiple starting points for threads, (bottle caps, etc), sporadically located bosses that the liquid hits as it drops, assisting in separation.

In one embodiment, the hand piece will be a self-contained, portable unit with a rechargeable battery, have a motor-driven piston pump for liquid delivery, have a mechanism to control the liquid flow, keep the temperature within a specified range, be modular in design, and have ergonomics well-suited to the user's hand. When the hand piece is in the base station, it will recharge the battery, refill the liquid reservoirs in the hand piece from those in the base station, and exchange samples and/or diagnostic information with the base station. It may also go through a cleaning process.

FIGS. 18a-18l show an example of an embodiment of a dental cleaning system 2000 of the present invention. The figures show dental cleaning system 2000, showing hand piece 2220, base station 2250, and base station liquid reservoir 2280. Base station liquid reservoir 2280 is used to refill the liquid reservoirs in hand piece 2220. Application tray 2100 is shown attached to hand piece 2220.

In this embodiment, base station filling tube 2245 is the conduit through which cleaning or treatment liquid passes from base station liquid reservoir 2280 to the liquid reservoirs in hand piece 2220. Liquid leaves base station liquid reservoir 2280 through base station liquid reservoir port 2285, and enters the liquid reservoirs in hand piece 2220 through hand piece port 2225.

When in base station 2250, the internal battery of hand piece 2220 will recharge, and the liquid reservoirs in hand piece 2220 will refill from those in base station 2250. Any diagnostic information in hand piece 2220 will be exchanged with base station 2250. Hand piece 2220 may also go through a cleaning process.

Figure 18A:
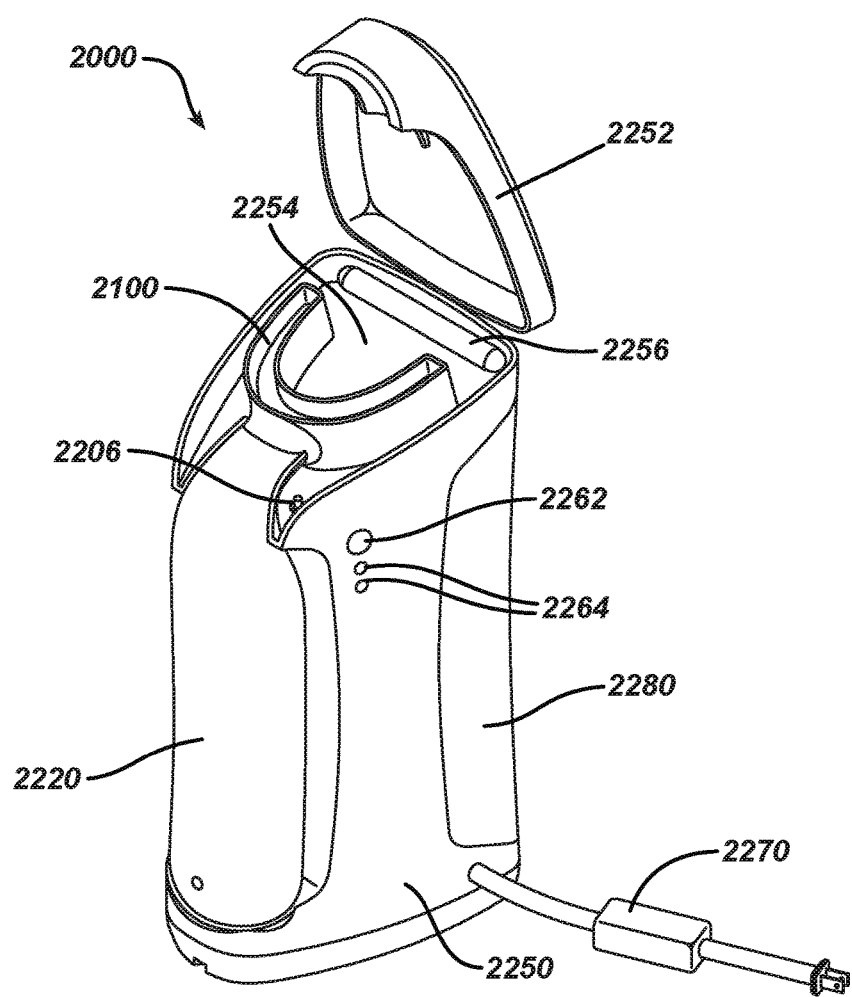
FIG. 18a is a front, top perspective view of an embodiment of a system that may be utilized in the present invention.

FIG. 18a is a front, top perspective view of an embodiment of a dental cleaning system 2000, including hand piece 2220, base station 2250, and base station liquid reservoir 2280. Base station 2250 includes base station lid 2252, sanitation chamber 2254, UV sanitizing light 2256, UV light kill switch 2206, start button 2262, indicator lights 2264, and power cord with AC adapter 2270. UV sanitizing light 2256 in sanitation chamber 2254, is used to sanitize application tray 2100 between uses. UV light kill switch 2206 shuts down UV sanitizing light 2256 when base station lid 2252 is opened or ajar. The UV kill switch can also be utilized to initiate the sanitation process when the lid is closed and the hand piece is docked. Indicator lights 2264 can be used to inform the user of the status of hand piece 2220 charge, position, or sanitation status, or the status of the base station liquid reservoir 2280 (full/empty, for example).

Figure 18B:
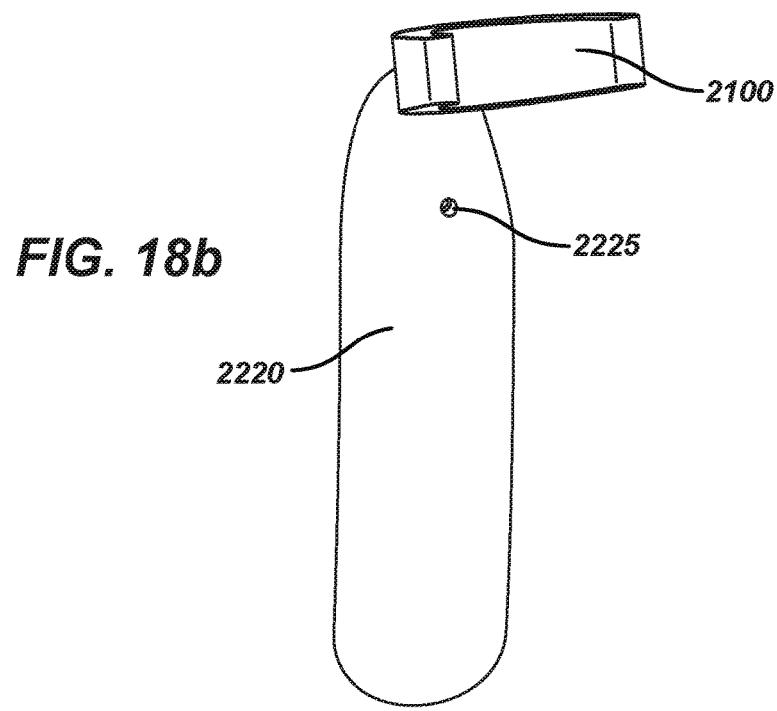
FIG. 18b is a front, top perspective view of the hand piece section of the system.

Hand piece 2220 includes attached application tray 2100, and as shown in FIG. 18b, and hand piece port 2225. Fluid enters and exits hand piece 2220 through hand piece port 2225.

Figure 18C:
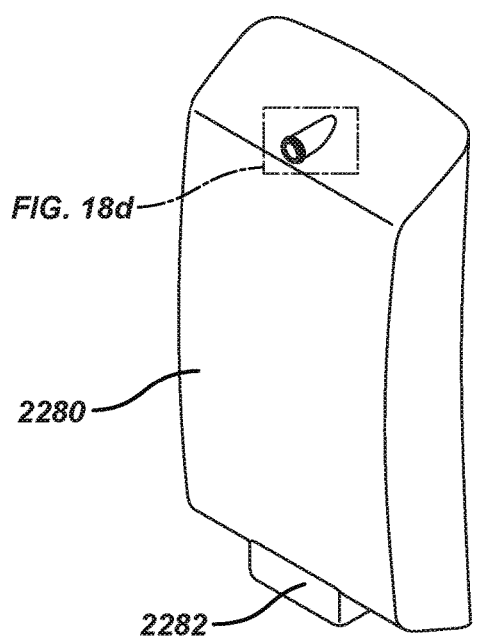
FIG. 18c is a front, top perspective view of the liquid reservoir section of the system.
Figure 18D:
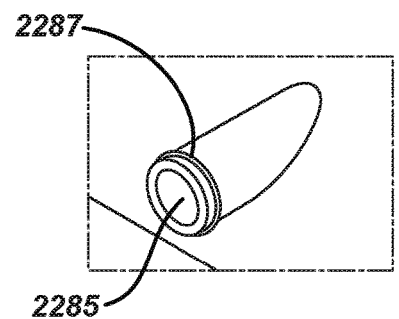
FIG. 18d is an inset view of a region of the liquid reservoir of FIG. 18c.

A front, top perspective view of base station liquid reservoir 2280 is shown in FIG. 18c. As shown in the inset view of base station liquid reservoir 2280 (FIG. 18d), base station liquid reservoir 2280 includes base station liquid reservoir port 2285, from which fresh fluid is used to fill hand piece 2220, and base station liquid reservoir locking feature 2282, used to engage base station liquid reservoir 2280 to base station 2250. Base station liquid reservoir port 2285 includes O-ring 2287 to insure a seal between reservoir port 2285 and base station inlet tube 2245a.

Figure 18E:
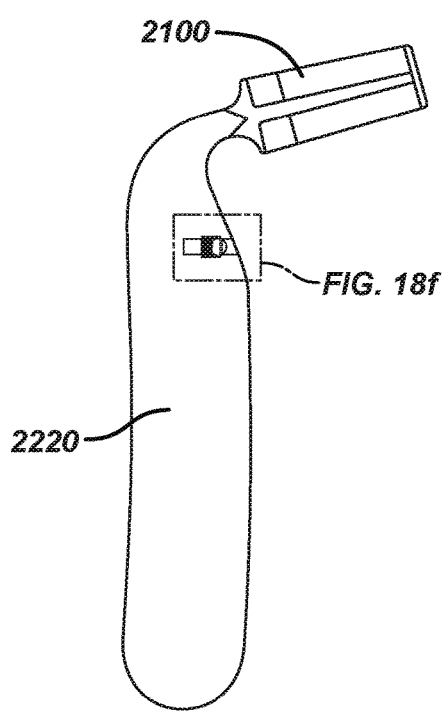
FIG. 18e is cross-sectional view of the hand piece section of the system.
Figure 18F:
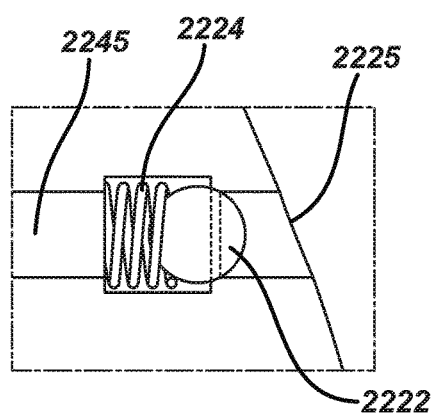
FIG. 18f is an inset view of a region of the hand piece of FIG. 18e.

A partial cross-section of hand piece 2220 is shown in FIG. 18e. As shown in the inset view of hand piece 2220 (FIG. 18f), hand piece port 2225 includes hand piece port 2225, from which fresh fluid is used to fill hand piece 2220. Hand piece port 2225 includes ball bearing 2222 and spring 2224 assembly. Fluid entering hand piece 2220 through hand piece port 2225 passes through ball bearing 2222 and spring 2224 assembly, which act as a sealing means for hand piece 2220, when not engaged in the base station.

Figure 18H:
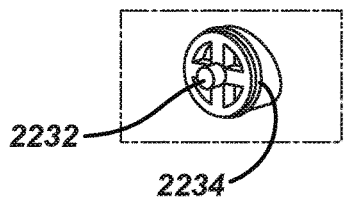
FIG. 18h is an inset view of a region of base station of FIG. 18g.
Figure 18G:
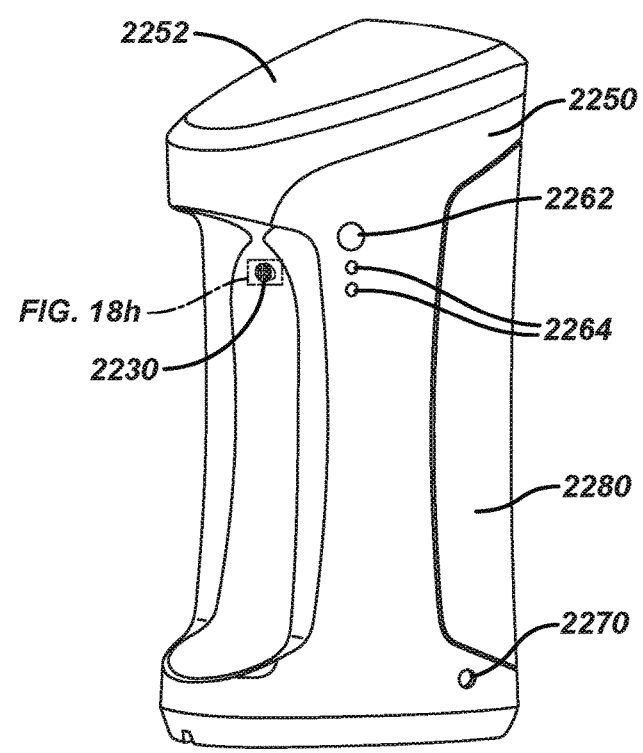
FIG. 18g is a front, top perspective view of the system of FIG. 18a, with the liquid reservoir attached to the base station.

FIG. 18g with inset view FIG. 18h shows the base station-to-hand piece docking feature 2232. Fluid from base station port 2230 passes through docking feature 2232 prior to entering hand piece port 2225. O-ring 2234 insures a seal between base station port 2230 and hand piece port 2225. A switch/sensor may also be located in the base station 2250 hand piece docking area to ensure hand piece 2220 is in the proper docking position for fluid loading from base station 2250 and/or initiation of the appliance tray sanitation process. The hand held position/docking status may also be verified through feedback of the base station to hand held charging circuit.

Figure 18I:
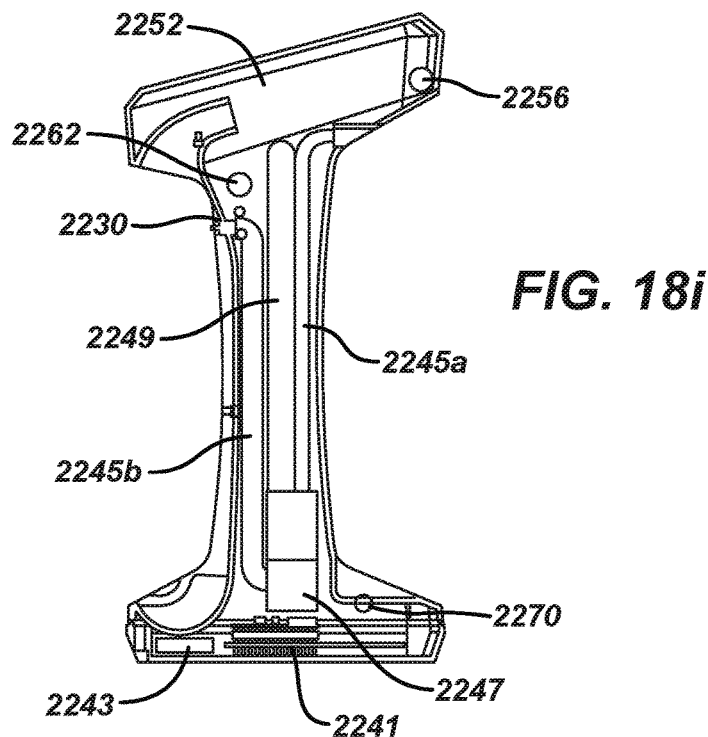

FIG. 18i is a cut-away view of base station 2250 without hand piece 2220 or base station liquid reservoir 2280 attached. The cut-away view shows pump 2247, heating coil 2249, reservoir to pump tube 2245a, base station pump to base station port tube 2245b, as well as the microcontroller and circuit board 2241 and hand piece charging pad 2243 located on base station 2250.

Figure 18J:
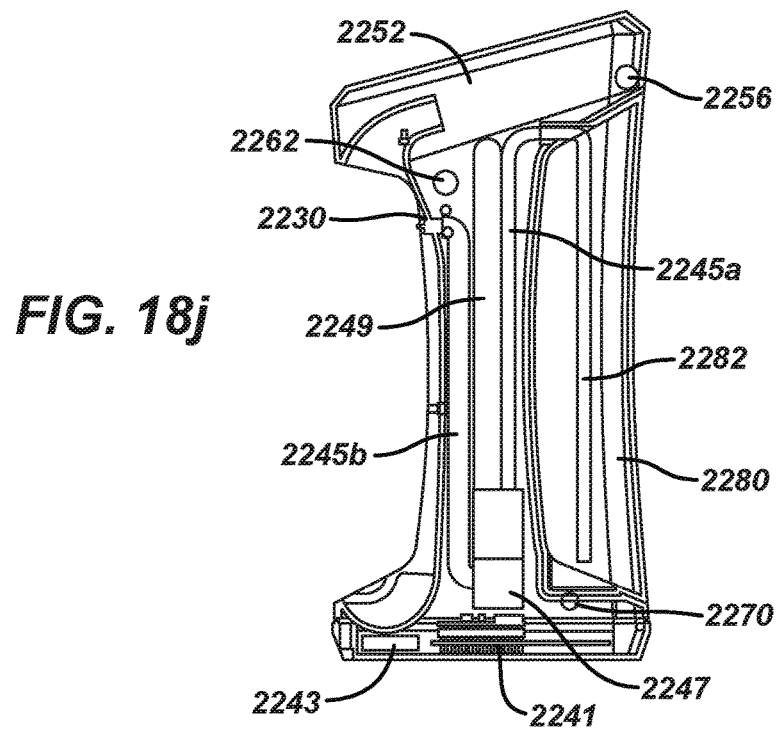
FIG. 18j is a cut-away view of the system of FIG. 18a, with the liquid reservoir attached to the base station.

FIG. 18j is a cut-away view base station 2250 with base station liquid reservoir 2280 attached. Base station liquid reservoir locking feature 2282 is used to engage base station liquid reservoir 2280 to base station 2250. When engaged, fluid in base station liquid reservoir 2280 can pass through base station reservoir tube 2282, exiting base station liquid reservoir 2280 through reservoir port 2285 and entering base station 2250 through base station inlet tube 2245a. Heating coil 2249 is used to warm fluid in tubes 2245a and 2245b prior to the fluid entering hand piece 2220.

Figure 18K:
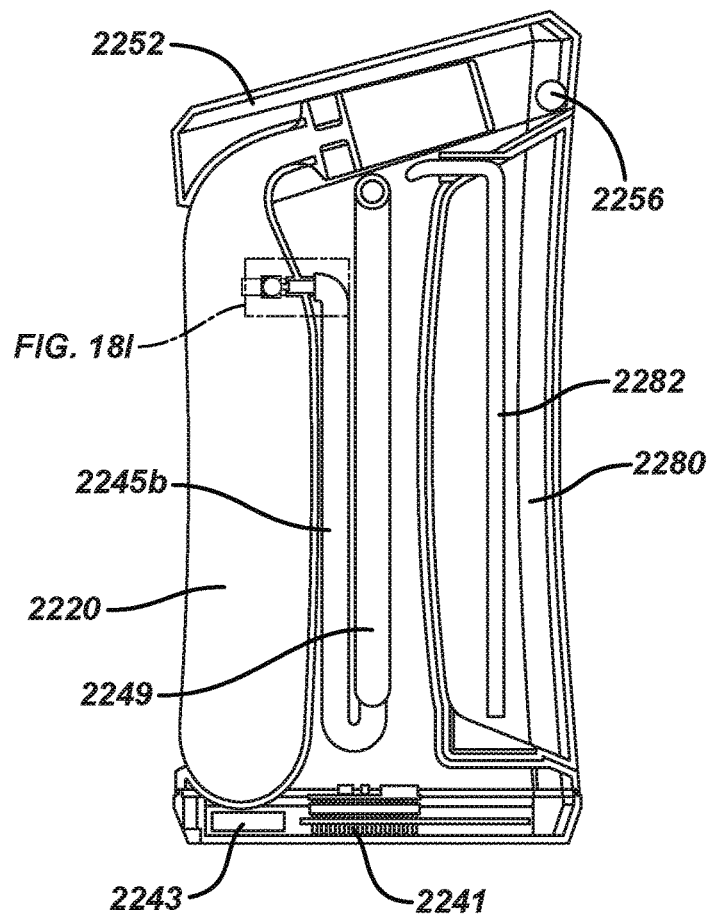
FIG. 18k is a cut-away view of the system of FIG. 18a, with the liquid reservoir and the hand piece attached to the base station.
Figure 18L:
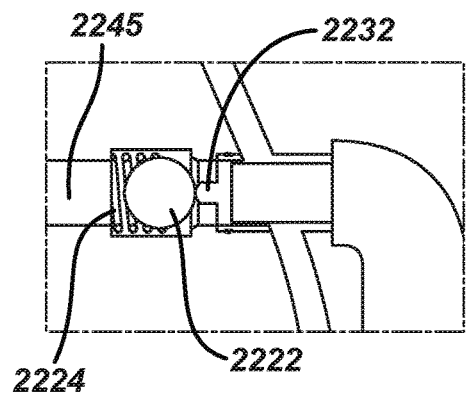
FIG. 18l is an inset view of a region of base station and hand piece of FIG. 18k.

FIG. 18k is a cut-away view of base station 2250 with hand piece 2220 and base station liquid reservoir 2280 attached. As shown in inset view (FIG. 18l), when hand piece 2220 is attached to base station 2250, docking feature 2232 contacts ball bearing 2222 and spring 2224 assembly, displacing ball bearing 2222 and allowing fluid to fill hand piece 2220.

In this embodiment, base station liquid reservoir 2280 would be loaded in base station 2250, containing sufficient fluid quantity to allow reservoir 2280 to be used a number of times before being empty. The removable and replaceable reservoir 2280 would engage with the base station 2250 through liquid reservoir locking feature 2282 to both correctly position and hold reservoir 2280 in base station 2250, and provide a seal for fluid conduit into the base station 2250.

Fluid would be pumped from base station liquid reservoir 2280 past heating coil 2249 where it would be heated to an acceptable temperature to minimize sensitivity when applied into the LCC when applied during the cleaning/treatment process.

Hand piece 2220 is placed into the handle dock in base station 2250 by the user. Hand piece 2220 engages with base station 2250 through docking features to both correctly position and hold hand piece 2220 in the correct position in base station 2250 to allow fluid to be pumped from base station liquid reservoir 2280 and into the local reservoir in hand piece 2220. Hand piece 2220 includes a feature that is opened to provide the conduit for fluid flow from base station 2250 when properly placed in the docking station. When hand piece 2220 is removed from base station 2250, the fluid channel is automatically closed and sealed.

In summary, base station 2250 houses the handle fluid loading system, the fluid heating system, the mouthpiece UV sanitation chamber, the handheld charging station, and control electronics and signal conditioning to control all aspects of the fluid loading, heating, and mouthpiece sanitation, as well as providing a docking station for the hand piece 2220 unit and the consumable reservoir 2280. Base station 2250 may also include user interface to provide feedback to the user on the system status and diagnostic analysis results such as, but not limited to fluid level, charging level, sanitation process status, last time device was used.

In other embodiments, a piston pump with check-valves will be used for liquid delivery.

In yet other embodiments, a rotary piston pump will be used for liquid delivery. This pump is known by those in the art, and the piston rotates as it reciprocates, therefore not needing any valves to operate. Reversing the rotation direction of the drive motor will reverse the liquid flow direction.

In still other embodiments diaphragm pumps, gear pumps, or double-action piston pumps will be used for liquid delivery. In the case of double-action piston pumps, when the liquid system is charged, this pump type has the benefit of reciprocating the direction of the liquid flow to the mouthpiece. Charged pneumatic cylinders, hand pump, or rotary pumps may be used to drive the system.

Example

A test was performed in which 4 subjects used devices according to the present invention to assess efficacy of the devices and methods of the invention from a germ removal and kill perspective. One of the endpoint methods used included bacterial viability determination via adenosine triphosphate (ATP) luminescence and total plate counts. Appropriate dilutions of the baseline samples were made in 0.1% peptone water. Both the rinsate and post-rinse samples were neutralized to stop antimicrobial actions and were diluted $PO_4$ neutralizer. Mouthpieces substantially similar to those depicted in FIGS. 16-19 (universal mouthpiece) and FIGS. 20-23 (custom-fit) were used in the test, one each of which was tested using water and the other with Cool Mint Listerine® mouth rinse (CML).

Total Cell Counts measuring colony forming units (CFU/ml), including total viable bacterial cells and total viable bad breath organisms, were used, respectively. The samples taken from the subjects were incubated under anaerobic conditions for 5 days at 35-37° C. The Relative Light Units (RLU) is a measure of the amount of ATP in a sample. The higher the RLU value, the more ATP is present, and the more live bacteria there are. Total cell counts (CFU/ml) and RLU were determined for each sample taken from the subjects both before (baseline) and post rinsing, as well as on rinsates collected after rinsing.

The subjects rinsed the oral cavity with 5 mL water for 10 seconds. The baseline example was collected by having the subject expectorate the rinse water into a conical tube, and then expectorating an additional 1 ml of saliva into that tube. Each subject then rinsed the oral cavity, 2 with water using the respective mouthpiece designs, and 2 with the Cool Mint Listerine using the respective mouthpiece designs. The rinsate was then collected for each subject and 20 mL was placed in a conical tube. Each subject then repeated the rinse with 5 mL of water for 10 seconds and, as before, the rinse and the post-rinse sample collected in a conical tube. The samples were neutralized, diluted, plated and then incubated for 5 days and the cell counts and ATP measured. Results are presented in Tables 1-3. Subject 1 BL used water as the liquid and the universal mouthpiece. Subject 2 BL used water as the liquid and the custom-fit mouthpiece. Subject 3 BL used CML as the liquid and the universal mouthpiece. Subject 4 BL used CML as the liquid and the custom-fit mouthpiece.

TABLE 1

| Total Organisms | Average Counts | % Reduction from baseline | log reduction |
|---|---|---|---|
| Subject 1 BL | 1.88E+07 | | |
| Subject 2 BL | 2.07E+07 | | |
| Subject 3 BL | 1.13E+08 | | |
| Subject 4 BL | 1.93E+08 | | |
| Subject 1 Rinsate | 7.40E+04 | 99.6% | 2.40 |
| Subject 2 Rinsate | 1.90E+04 | 99.9% | 3.04 |
| Subject 3 Rinsate | 2.00E+03 | 100.0% | 4.75 |
| Subject 4 Rinsate | 3.00E+03 | 100.0% | 4.81 |
| Subject 1 Post | 7.50E+05 | 96.0% | 1.40 |
| Subject 2 Post | 3.02E+06 | 85.4% | 0.84 |
| Subject 3 Post | 8.70E+06 | 92.3% | 1.11 |
| Subject 4 Post | 7.20E+06 | 96.3% | 1.43 |

TABLE 2

| Bad Breath Organisms | Average Counts | % Reduction from baseline | log reduction |
|---|---|---|---|
| Subject 1 BL | 5.30E+06 | | |
| Subject 2 BL | 2.70E+06 | | |
| Subject 3 BL | 2.10E+07 | | |
| Subject 4 BL | 3.50E+07 | | |
| Subject 1 Rinsate | 3.10E+04 | 99.4% | 2.23 |
| Subject 2 Rinsate | 1.00E+03 | 100.0% | 3.43 |
| Subject 3 Rinsate | 1.50E+03 | 100.0% | 4.15 |
| Subject 4 Rinsate | 1.00E+03 | 100.0% | 4.54 |
| Subject 1 Post | 6.50E+05 | 87.7% | 0.91 |
| Subject 2 Post | 4.40E+05 | 83.7% | 0.79 |
| Subject 3 Post | 2.80E+06 | 86.7% | 0.88 |
| Subject 4 Post | 2.10E+06 | 94.0% | 1.22 |

TABLE 3

| ATP | RLU | % Reduction from baseline | log reduction |
|---|---|---|---|
| Subject 1 BL | 7.44E+04 | | |
| Subject 2 BL | 3.93E+04 | | |
| Subject 3 BL | 2.18E+05 | | |
| Subject 4 BL | 3.12E+05 | | |
| Subject 1 Rinsate | 3.14E+04 | 57.7% | 0.37 |
| Subject 2 Rinsate | 2.85E+04 | 27.4% | 0.14 |
| Subject 3 Rinsate | 2.81E+04 | 87.1% | 0.89 |
| Subject 4 Rinsate | 2.61E+04 | 91.6% | 1.08 |
| Subject 1 Post | 3.01E+04 | 59.5% | 0.39 |
| Subject 2 Post | 2.90E+04 | 26.1% | 0.13 |
| Subject 3 Post | 7.04E+04 | 67.7% | 0.49 |
| Subject 4 Post | 3.40E+04 | 89.1% | 0.96 |

CONCLUSIONS

Post-rinse plate count data demonstrates approximate significant reduction for both water rinse and CML rinse. Analysis of the rinsate plate count data also demonstrates a significant reduction from the baseline in the water rinse, and even more significant reduction from the baseline in the CML rinse. The log reductions present in the water rinsate suggests mechanical bacterial removal during treatment in the absence of antimicrobials. The higher log reductions present in the CML rinsate suggests a combination of mechanical and antimicrobial activity during treatment.

Though several embodiments have been described, it should be understood that the scope of the present invention embraces other possible variations, being limited only by the contents of the accompanying claims, which includes the possible equivalents.

What is claimed is:

1. A device suitable for collecting sample of a fluid from the oral cavity of a mammal, comprising:
    a mouthpiece comprising a chamber defined by front and rear inner walls and a base inner wall of said mouthpiece, said base wall extending between said front and rear inner walls, each of said front and rear inner walls of said chamber comprising a plurality of openings, said mouthpiece further comprising a first manifold for containing a first portion of a liquid and providing said first portion to said chamber through said openings of said front inner wall, a second manifold for containing a second portion of said liquid and providing said second portion to said chamber through said openings of said rear inner wall, and a first port for conveying said first portion of said liquid to and from said first manifold, a second port for conveying said second portion of said liquid to and from said second manifold;
    means for providing reciprocation comprising a pump system for alternately: (i) directing fluid into said chamber through said first manifold and out of said chamber through said second manifold, and (ii) directing fluid into said chamber through said second manifold and out of said chamber through said first manifold; and
    means for collecting said fluid sample from said oral cavity.

2. The device of claim 1 wherein said fluid is selected from the group consisting of a gas, gingival crevicular fluid, blood and saliva.

3. The device of claim 1 wherein said means for collecting said fluid sample is selected from the group consisting of a manifold dedicated to collection of said fluid, an orifice and a plurality of nozzles placed at spaced intervals about said mouthpiece.

4. The device of claim 1 wherein said means for collecting fluid samples comprise said openings in at least one of said inner walls, at least one of said first and second manifolds and at least one of said first and second ports.

5. The device of claim 1 comprising a compartment for storage of said fluid sample.

6. The device of claim 5 wherein said compartment is detachable from said device.

7. A method for collecting and analyzing a sample of a fluid from the oral cavity of a mammal, said method comprising:
    placing a device suitable for collecting said sample of said fluid in said oral cavity of said mammal, said device comprising:
    a mouthpiece comprising a chamber defined by front and rear inner walls and a base inner wall of said mouthpiece, said base wall extending between said front and rear inner walls a mouthpiece comprising a chamber defined by front and rear inner walls and a base inner wall of said mouthpiece, said base wall extending between said front and rear inner walls, each of said front and rear inner walls of said chamber comprising a plurality of openings, said mouthpiece further comprising a first manifold for containing a first portion of a liquid and providing said first portion to said chamber through said openings of said front inner wall, a second manifold for containing a second portion of said liquid and providing said second portion to said chamber through said openings of said rear inner wall, and a first port for conveying said first portion of said liquid to and from said first manifold, a second port for conveying said second portion of said liquid to and from said second manifold;
    means for providing reciprocation comprising a pump system for alternately: (i) directing fluid into said chamber through said first manifold and out of said chamber through said second manifold, and (ii) directing fluid into said chamber through said second manifold and out of said chamber through said first manifold; and
    means for collecting said fluid sample from said oral cavity, collecting said fluid sample from said oral cavity; and conducting an analysis of said fluid sample.

8. The method of claim 7 wherein said collection is conducted simultaneously with directing said liquid onto said plurality of surfaces of said oral cavity of said mammal.

9. The method of claim 7 wherein said collection is conducted prior to directing said liquid onto said plurality of surfaces of said oral cavity of said mammal.

10. The method of claim 7 wherein said collection is conducted after directing said liquid onto said plurality of surfaces of said oral cavity of said mammal.

11. The method of claim 7 wherein said collection is conducted prior to and after directing said liquid onto said plurality of surfaces of said oral cavity of said mammal.

12. The method of claim 7 wherein said collection is conducted prior to, simultaneously with and after directing said liquid onto said plurality of surfaces of said oral cavity of said mammal.

13. The method of claim 7 wherein analysis of said fluid sample is conducted by a method selected from the group consisting of lateral flow technology, microfluidic immunoassay, DNA-DNA hybridization, color metrics, photoimaging, gas chromatography, zinc oxide semiconductor sensors, quantitative light fluorescence and quantitative Polymerase Chain Reaction.

14. The method of claim 7 wherein said means for collecting said fluid sample is selected from the group consisting of a manifold dedicated to collection of said fluid, an orifice and a plurality of nozzles placed at spaced intervals about said mouthpiece, said openings in at least one of said inner walls, at least one of said first and second manifolds and at least one of said first and second ports.

15. The method of claim 7 wherein said means for collecting said fluid sample is selected from the group consisting of said openings in at least one of said inner walls, at least one of said first and second manifolds and at least one of said first and second ports.

16. The method of claim 7 wherein said fluid is selected from the group consisting of a gas, gingival crevicular fluid, blood and saliva.

17. The method of claim 7 further comprising introducing an agent selected from the group consisting of a fluid sample stimulating agent, a conglomeration agent and a coagulation agent.

* * * * *